US009072688B2

(12) United States Patent
Boyden et al.

(10) Patent No.: US 9,072,688 B2
(45) Date of Patent: Jul. 7, 2015

(54) COMPOSITIONS AND METHODS FOR THERAPEUTIC DELIVERY WITH FROZEN PARTICLES

(75) Inventors: Edward S. Boyden, Cambridge, MA (US); Roderick A. Hyde, Redmond, WA (US); Eric C. Leuthardt, St. Louis, MO (US); Nathan P. Myhrvold, Medina, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1075 days.

(21) Appl. No.: 12/290,671

(22) Filed: Oct. 31, 2008

(65) Prior Publication Data

US 2010/0111842 A1    May 6, 2010

(51) Int. Cl.
| A61K 9/00 | (2006.01) |
| A61K 9/16 | (2006.01) |
| A61K 9/08 | (2006.01) |
| A61K 31/00 | (2006.01) |
| A61K 51/12 | (2006.01) |
| A61K 33/00 | (2006.01) |
| A61K 9/19 | (2006.01) |
| A61K 31/337 | (2006.01) |
| A61K 31/70 | (2006.01) |
| A61K 31/7088 | (2006.01) |
| A61K 41/00 | (2006.01) |
| A61K 45/06 | (2006.01) |
| A61K 39/00 | (2006.01) |

(52) U.S. Cl.
CPC ............. *A61K 33/00* (2013.01); *A61K 9/0019* (2013.01); *A61K 9/007* (2013.01); *A61K 9/08* (2013.01); *A61K 9/1611* (2013.01); *A61K 9/1641* (2013.01); *A61K 9/1664* (2013.01); *A61K 9/1688* (2013.01); *A61K 9/19* (2013.01); *A61K 31/00* (2013.01); *A61K 31/337* (2013.01); *A61K 31/70* (2013.01); *A61K 31/7088* (2013.01); *A61K 39/00* (2013.01); *A61K 41/0004* (2013.01); *A61K 45/06* (2013.01); *A61K 51/1244* (2013.01)

(58) Field of Classification Search
CPC ......... A61K 9/00; A61K 9/0019; A61K 9/08; A61K 9/1611; A61K 9/167; A61K 31/00; A61K 51/1244
See application file for complete search history.

(56) References Cited

U.S. PATENT DOCUMENTS

| 1,433,628 A | 10/1922 | Knaust |
| 2,182,952 A | 12/1939 | Todd et al. |
| 2,975,603 A | 3/1961 | Barnes et al. |
| 3,086,370 A | 4/1963 | Barnes et al. |
| 3,089,775 A | 5/1963 | Lindall |
| 3,217,503 A | 11/1965 | Mitchell et al. |
| 3,276,880 A | 10/1966 | Torr |
| 3,491,170 A | 1/1970 | Roe, Jr. |
| 3,500,242 A | 3/1970 | Young |
| 3,551,535 A | 12/1970 | Henderson et al. |
| 3,577,516 A | 5/1971 | Gould et al. |
| 3,733,158 A | 5/1973 | Ruekberg |
| 3,787,302 A | 1/1974 | Ijichi et al. |
| 3,808,097 A | 4/1974 | Fowler et al. |
| 3,868,997 A | 3/1975 | Pogers |
| 3,889,002 A | 6/1975 | Clausi et al. |
| 3,911,601 A * | 10/1975 | Maheu .......................... 37/253 |
| 3,914,441 A | 10/1975 | Finney et al. |
| 4,016,264 A | 4/1977 | Clark |
| 4,102,765 A | 7/1978 | Fey et al. |
| 4,146,029 A | 3/1979 | Ellinwood, Jr. |
| 4,152,231 A | 5/1979 | St. Clair et al. |
| 4,207,360 A | 6/1980 | Padovani |
| 4,262,029 A | 4/1981 | Kleiner et al. |
| 4,289,790 A | 9/1981 | Bruelle |
| 4,289,794 A | 9/1981 | Kleiner et al. |
| 4,297,379 A | 10/1981 | Topalian et al. |
| 4,312,850 A | 1/1982 | Dietl et al. |
| 4,394,370 A | 7/1983 | Jefferies |
| 4,394,863 A | 7/1983 | Bartner |
| 4,404,807 A | 9/1983 | Zemelman et al. |
| 4,442,082 A | 4/1984 | Sanjurjo |
| 4,487,023 A | 12/1984 | Hegadorn et al. |
| 4,512,160 A | 4/1985 | Arias Mas |
| 4,590,043 A | 5/1986 | Sanjurjo |
| 4,603,051 A | 7/1986 | Rubenstein et al. |
| 4,617,064 A | 10/1986 | Moore |
| 4,637,905 A | 1/1987 | Gardner |

(Continued)

FOREIGN PATENT DOCUMENTS

| CA | 992756 A | 7/1976 |
| CN | 1698583 A | 4/2005 |
| EP | 0 289 186 A2 | 4/1988 |
| GB | 2439092 A | 12/2007 |
| WO | WO 92/01802 A1 | 2/1992 |
| WO | WO 00/09670 | 2/2000 |
| WO | WO 03/060002 A1 | 7/2003 |
| WO | WO 2004/052334 A2 | 6/2004 |
| WO | WO 2006/069181 A2 | 6/2006 |
| WO | WO 2007/024323 A2 | 3/2007 |
| WO | WO 2007/149868 A2 | 12/2007 |
| WO | WO 2009/113856 A1 | 9/2009 |

OTHER PUBLICATIONS

Clements, H.F., "Life and the Wonders of Water", 1976, Harold L. Lyon Arboretum Lecture Number Seven, pp. 1-34.*

(Continued)

*Primary Examiner* — Michael G Hartley
*Assistant Examiner* — Lance W Rider

(57) ABSTRACT

Certain embodiments disclosed herein relate to compositions, methods, devices, systems, and products regarding frozen particles. In certain embodiments, the frozen particles include materials at low temperatures. In certain embodiments, the frozen particles provide vehicles for delivery of particular agents. In certain embodiments, the frozen particles are administered to at least one biological tissue.

33 Claims, 36 Drawing Sheets

(56) References Cited

U.S. PATENT DOCUMENTS

| | | | |
|---|---|---|---|
| 4,703,590 A | 11/1987 | Westergaard | |
| 4,704,873 A | 11/1987 | Imaike et al. | |
| 4,712,920 A | 12/1987 | Ames et al. | |
| 4,861,714 A | 8/1989 | Dean, Jr. et al. | |
| 4,907,415 A | 3/1990 | Stewart, Jr. et al. | |
| 4,921,720 A | 5/1990 | Davis | |
| 4,945,050 A | 7/1990 | Sanford et al. | |
| 4,951,197 A | 8/1990 | Mellinger | |
| 4,958,014 A | 9/1990 | Shirokaze | |
| 4,962,091 A | 10/1990 | Eppstein et al. | |
| 4,974,679 A | 12/1990 | Reuter | |
| 4,981,625 A | 1/1991 | Rhim et al. | |
| 5,006,338 A | 4/1991 | Luenemann | |
| 5,008,116 A | 4/1991 | Cahn | |
| 5,049,328 A | 9/1991 | Meyer et al. | |
| 5,072,596 A | 12/1991 | Gilbertson et al. | |
| 5,090,208 A | 2/1992 | Aono et al. | |
| 5,102,983 A | 4/1992 | Kennedy | |
| 5,114,957 A | 5/1992 | Hendler et al. | |
| 5,126,156 A | 6/1992 | Jones | |
| 5,132,101 A | 7/1992 | Vogel et al. | |
| 5,158,760 A | 10/1992 | Phillips et al. | |
| 5,183,462 A | 2/1993 | Borodic | |
| 5,216,890 A | 6/1993 | Ban et al. | |
| 5,219,746 A * | 6/1993 | Brinegar et al. | 435/6 |
| 5,231,015 A * | 7/1993 | Cummins et al. | 435/91.2 |
| 5,236,419 A | 8/1993 | Seney | |
| 5,283,985 A | 2/1994 | Browning | |
| 5,283,989 A | 2/1994 | Hisasue et al. | |
| 5,307,640 A | 5/1994 | Fawzy et al. | |
| 5,315,793 A | 5/1994 | Peterson et al. | |
| 5,328,517 A | 7/1994 | Cates et al. | |
| 5,331,046 A | 7/1994 | Chang et al. | |
| 5,341,608 A | 8/1994 | Mains, Jr. | |
| 5,352,673 A * | 10/1994 | Dennis | 514/78 |
| 5,354,284 A | 10/1994 | Haber et al. | |
| 5,365,699 A | 11/1994 | Armstrong et al. | |
| 5,367,838 A | 11/1994 | Visaisouk et al. | |
| 5,375,432 A | 12/1994 | Cur | |
| 5,390,450 A | 2/1995 | Goenka | |
| 5,394,705 A | 3/1995 | Torii et al. | |
| 5,424,073 A * | 6/1995 | Rahman et al. | 424/450 |
| 5,433,654 A | 7/1995 | Clark, Jr. et al. | |
| 5,436,039 A | 7/1995 | Miura et al. | |
| 5,438,071 A | 8/1995 | Clauss et al. | |
| 5,439,698 A | 8/1995 | Ahn et al. | |
| 5,444,986 A | 8/1995 | Hino | |
| 5,520,572 A | 5/1996 | Opel et al. | |
| 5,534,584 A | 7/1996 | Kitamura et al. | |
| 5,599,223 A | 2/1997 | Mains Jr. | |
| 5,620,414 A | 4/1997 | Campbell, Jr. | |
| 5,630,796 A | 5/1997 | Bellhouse et al. | |
| 5,631,023 A | 5/1997 | Kearney et al. | |
| 5,632,150 A | 5/1997 | Henzler | |
| 5,652,058 A | 7/1997 | Nagata et al. | |
| 5,656,317 A | 8/1997 | Smits et al. | |
| 5,666,821 A | 9/1997 | Foster et al. | |
| 5,690,940 A | 11/1997 | Joo | |
| 5,699,880 A | 12/1997 | Hockley | |
| 5,707,667 A | 1/1998 | Galt et al. | |
| 5,725,491 A | 3/1998 | Tipton et al. | |
| 5,725,579 A | 3/1998 | Fages et al. | |
| 5,745,377 A | 4/1998 | Power et al. | |
| 5,753,234 A * | 5/1998 | Lee et al. | 424/204.1 |
| 5,764,493 A | 6/1998 | Liao | |
| 5,779,523 A | 7/1998 | Mesher | |
| 5,785,581 A | 7/1998 | Settles | |
| 5,820,447 A | 10/1998 | Niechcial | |
| 5,855,663 A | 1/1999 | Takano et al. | |
| 5,860,957 A | 1/1999 | Jacobsen et al. | |
| 5,877,819 A | 3/1999 | Branson | |
| 5,883,078 A | 3/1999 | Seelich et al. | |
| 5,910,042 A | 6/1999 | Niechcial | |
| 5,913,711 A | 6/1999 | Visaisouk | |
| 5,931,721 A | 8/1999 | Rose et al. | |
| 5,954,640 A | 9/1999 | Szabo | |
| 5,961,732 A | 10/1999 | Patrin et al. | |
| 5,962,018 A | 10/1999 | Curtis et al. | |
| 5,971,999 A | 10/1999 | Naldoni | |
| 5,976,505 A | 11/1999 | Henderson | |
| 5,977,163 A | 11/1999 | Li et al. | |
| 6,001,385 A | 12/1999 | Van De Wijdeven | |
| 6,080,329 A | 6/2000 | Dobry | |
| 6,092,235 A * | 7/2000 | Santa Cruz et al. | 2/16 |
| 6,099,208 A | 8/2000 | McAlister | |
| 6,129,290 A | 10/2000 | Nikkanen | |
| 6,130,206 A * | 10/2000 | Carter | 514/44 R |
| 6,174,225 B1 | 1/2001 | Becker | |
| 6,192,693 B1 | 2/2001 | Kloppenberg et al. | |
| 6,203,406 B1 | 3/2001 | Rose et al. | |
| 6,241,704 B1 | 6/2001 | Peterson et al. | |
| 6,248,063 B1 | 6/2001 | Barnhill et al. | |
| 6,264,666 B1 | 7/2001 | Coleman et al. | |
| 6,270,723 B1 | 8/2001 | Laugharn, Jr. et al. | |
| 6,284,283 B1 | 9/2001 | Costantino et al. | |
| 6,306,119 B1 | 10/2001 | Weber et al. | |
| 6,311,639 B1 | 11/2001 | Stickney | |
| 6,341,831 B1 | 1/2002 | Weber et al. | |
| 6,349,549 B1 | 2/2002 | Angus et al. | |
| 6,350,185 B1 | 2/2002 | Robins et al. | |
| 6,350,451 B1 | 2/2002 | Horn et al. | |
| 6,366,206 B1 | 4/2002 | Ishikawa et al. | |
| 6,379,324 B1 | 4/2002 | Gartstein et al. | |
| 6,383,329 B1 | 5/2002 | Agarwala et al. | |
| 6,399,144 B2 | 6/2002 | Dinh et al. | |
| 6,407,670 B1 | 6/2002 | Dysarsz et al. | |
| 6,436,422 B1 | 8/2002 | Trogolo et al. | |
| 6,454,811 B1 | 9/2002 | Sherwood et al. | |
| 6,464,570 B1 | 10/2002 | Shaw et al. | |
| 6,464,999 B1 | 10/2002 | Huo et al. | |
| 6,500,187 B1 | 12/2002 | Petersen | |
| 6,505,522 B1 | 1/2003 | Wilssens | |
| 6,569,458 B1 | 5/2003 | Gombotz et al. | |
| 6,623,457 B1 | 9/2003 | Rosenberg | |
| 6,656,114 B1 | 12/2003 | Poulsen et al. | |
| 6,659,844 B2 | 12/2003 | Shaw | |
| 6,678,669 B2 | 1/2004 | Lapointe et al. | |
| 6,695,686 B1 | 2/2004 | Frohlich et al. | |
| 6,705,194 B2 | 3/2004 | Geskin et al. | |
| 6,706,032 B2 | 3/2004 | Weaver et al. | |
| 6,712,237 B2 | 3/2004 | Medina et al. | |
| 6,712,558 B2 | 3/2004 | McAlister | |
| 6,713,083 B1 | 3/2004 | McGregor et al. | |
| 6,726,693 B2 | 4/2004 | Weber et al. | |
| 6,732,424 B2 | 5/2004 | Nadicksbernd | |
| 6,764,493 B1 | 7/2004 | Weber et al. | |
| 6,807,717 B2 | 10/2004 | Daehn | |
| 6,838,089 B1 | 1/2005 | Carlsson et al. | |
| 6,845,631 B1 | 1/2005 | Hallin et al. | |
| 6,875,984 B2 | 4/2005 | Kakibayashi et al. | |
| 6,986,265 B2 | 1/2006 | Johansen | |
| 6,991,515 B2 | 1/2006 | Akedo | |
| 6,997,949 B2 | 2/2006 | Tuch | |
| 7,000,300 B2 | 2/2006 | Daehn | |
| 7,033,249 B2 | 4/2006 | Spalteholz et al. | |
| 7,040,962 B2 | 5/2006 | Makino et al. | |
| 7,075,658 B2 | 7/2006 | Izatt et al. | |
| 7,125,561 B2 | 10/2006 | Sackler | |
| 7,140,954 B2 | 11/2006 | Johnson et al. | |
| 7,143,967 B2 | 12/2006 | Heinrich et al. | |
| 7,284,390 B2 | 10/2007 | Van Meter et al. | |
| 7,306,316 B2 | 12/2007 | Doak | |
| 7,347,851 B1 | 3/2008 | Kriksunov | |
| 7,350,374 B1 | 4/2008 | Tashlitsky | |
| 7,421,872 B2 | 9/2008 | Indlekofer | |
| 7,442,112 B2 | 10/2008 | Yoon | |
| 7,547,292 B2 | 6/2009 | Sheldrake et al. | |
| 7,666,778 B2 | 2/2010 | Young | |
| 7,917,298 B1 | 3/2011 | Scher et al. | |
| 7,922,565 B2 | 4/2011 | Knisel et al. | |
| 8,128,872 B2 | 3/2012 | Lentz et al. | |
| 8,256,233 B2 | 9/2012 | Boyden et al. | |
| 8,292,698 B2 | 10/2012 | Shih et al. | |
| 2001/0025495 A1 | 10/2001 | Newman et al. | |

(56) References Cited

U.S. PATENT DOCUMENTS

| | | |
|---|---|---|
| 2001/0038338 A1 | 11/2001 | Kadwell et al. |
| 2002/0002474 A1 | 1/2002 | Michelson et al. |
| 2002/0058952 A1 | 5/2002 | Weber et al. |
| 2002/0061329 A1 | 5/2002 | Leaderman |
| 2002/0068510 A1 | 6/2002 | Okazawa et al. |
| 2002/0082543 A1 | 6/2002 | Park et al. |
| 2002/0082745 A1 | 6/2002 | Wilmott et al. |
| 2002/0098534 A1 | 7/2002 | McCaskey-Feazel et al. |
| 2002/0107199 A1* | 8/2002 | Walker ............... 514/12 |
| 2002/0111362 A1 | 8/2002 | Rubinfeld |
| 2002/0122771 A1 | 9/2002 | Holland et al. |
| 2002/0132007 A1 | 9/2002 | Randolph et al. |
| 2002/0169411 A1 | 11/2002 | Sherman et al. |
| 2002/0197728 A1 | 12/2002 | Kaufman et al. |
| 2003/0003105 A1 | 1/2003 | Gerber |
| 2003/0012741 A1 | 1/2003 | Furlan et al. |
| 2003/0041602 A1 | 3/2003 | Williams, III et al. |
| 2003/0049320 A1 | 3/2003 | Bhagwatwar et al. |
| 2003/0065535 A1 | 4/2003 | Karlov et al. |
| 2003/0072814 A1 | 4/2003 | Maibach et al. |
| 2003/0104764 A1 | 6/2003 | Preising |
| 2003/0127054 A1 | 7/2003 | Hebrank |
| 2003/0135201 A1 | 7/2003 | Gonnelli |
| 2003/0147995 A1 | 8/2003 | Koss et al. |
| 2003/0166594 A1* | 9/2003 | Blum et al. ............... 514/44 |
| 2003/0181826 A1 | 9/2003 | Smith et al. |
| 2003/0181863 A1 | 9/2003 | Ackley et al. |
| 2003/0186957 A1 | 10/2003 | Blanchflower et al. |
| 2003/0207655 A1 | 11/2003 | Jackson |
| 2003/0216729 A1 | 11/2003 | Marchitto et al. |
| 2003/0229027 A1 | 12/2003 | Eissens et al. |
| 2004/0015115 A1 | 1/2004 | Sinyagin |
| 2004/0026617 A1 | 2/2004 | Gregori et al. |
| 2004/0029774 A1 | 2/2004 | Gamay |
| 2004/0037907 A1 | 2/2004 | Andersson et al. |
| 2004/0049150 A1 | 3/2004 | Dalton et al. |
| 2004/0059282 A1 | 3/2004 | Flock et al. |
| 2004/0076319 A1 | 4/2004 | Fauver et al. |
| 2004/0091543 A1 | 5/2004 | Bell et al. |
| 2004/0092920 A1 | 5/2004 | Rozenshpeer |
| 2004/0093240 A1 | 5/2004 | Shah |
| 2004/0106904 A1 | 6/2004 | Gonnelli et al. |
| 2004/0176732 A1 | 9/2004 | Frazier et al. |
| 2004/0180846 A1 | 9/2004 | Huang et al. |
| 2004/0193019 A1 | 9/2004 | Wei |
| 2004/0215135 A1 | 10/2004 | Sheldrake et al. |
| 2004/0219206 A1 | 11/2004 | Roser et al. |
| 2004/0236269 A1 | 11/2004 | Marchitto et al. |
| 2004/0244508 A1 | 12/2004 | Keskinen et al. |
| 2004/0254525 A1 | 12/2004 | Uber, III et al. |
| 2004/0260234 A1 | 12/2004 | Srinivasan et al. |
| 2005/0019380 A1 | 1/2005 | Hoon et al. |
| 2005/0057366 A1 | 3/2005 | Kadwell et al. |
| 2005/0059940 A1 | 3/2005 | Weber et al. |
| 2005/0086961 A1 | 4/2005 | McKay |
| 2005/0107006 A1 | 5/2005 | Makino et al. |
| 2005/0107832 A1 | 5/2005 | Bernabei |
| 2005/0137584 A1 | 6/2005 | Lemchen |
| 2005/0153690 A1 | 7/2005 | Marchitto et al. |
| 2005/0193451 A1 | 9/2005 | Quistgaard et al. |
| 2005/0215941 A1 | 9/2005 | Bernard et al. |
| 2005/0220887 A1 | 10/2005 | Herbert et al. |
| 2005/0261239 A1 | 11/2005 | Dagnelie et al. |
| 2005/0271733 A1 | 12/2005 | Burkoth et al. |
| 2006/0041241 A1 | 2/2006 | Herndon |
| 2006/0045881 A1 | 3/2006 | Molldrem |
| 2006/0100567 A1 | 5/2006 | Marchitto et al. |
| 2006/0123801 A1 | 6/2006 | Jackson |
| 2006/0123819 A1 | 6/2006 | Choe et al. |
| 2006/0129326 A1 | 6/2006 | Braconnier et al. |
| 2006/0153927 A1 | 7/2006 | Xu |
| 2006/0166233 A1 | 7/2006 | Wu et al. |
| 2006/0177564 A1 | 8/2006 | Diaz et al. |
| 2006/0178688 A1 | 8/2006 | Freeman et al. |
| 2006/0182738 A1 | 8/2006 | Holmes |
| 2006/0190195 A1 | 8/2006 | Watanabe et al. |
| 2006/0195269 A1 | 8/2006 | Yeatman et al. |
| 2006/0200369 A1 | 9/2006 | Batch et al. |
| 2006/0202385 A1 | 9/2006 | Xu et al. |
| 2006/0228465 A1 | 10/2006 | Zurecki |
| 2006/0258986 A1 | 11/2006 | Hunter et al. |
| 2007/0013910 A1 | 1/2007 | Jiang et al. |
| 2007/0020273 A1 | 1/2007 | Arlen et al. |
| 2007/0043320 A1 | 2/2007 | Kenany |
| 2007/0078376 A1 | 4/2007 | Smith |
| 2007/0078522 A2 | 4/2007 | Griffey et al. |
| 2007/0112598 A1 | 5/2007 | Heckerman et al. |
| 2007/0113639 A1 | 5/2007 | DiFoggio et al. |
| 2007/0135767 A1 | 6/2007 | Gillespie et al. |
| 2007/0148252 A1 | 6/2007 | Shaw et al. |
| 2007/0161964 A1 | 7/2007 | Yuzhakov |
| 2007/0178811 A1 | 8/2007 | Sundaram et al. |
| 2007/0186923 A1 | 8/2007 | Poutiatine et al. |
| 2007/0196437 A1 | 8/2007 | Hamaker et al. |
| 2007/0255589 A1 | 11/2007 | Rodriguez |
| 2008/0031934 A1 | 2/2008 | MacPhee et al. |
| 2008/0039521 A1 | 2/2008 | Yasuda et al. |
| 2008/0039773 A1 | 2/2008 | Py |
| 2008/0058732 A1 | 3/2008 | Harris |
| 2008/0085286 A1 | 4/2008 | Kalkum et al. |
| 2008/0167674 A1 | 7/2008 | Bodduluri et al. |
| 2009/0011087 A1 | 1/2009 | Rabault et al. |
| 2009/0062737 A1 | 3/2009 | Sun |
| 2009/0062783 A1 | 3/2009 | Sun |
| 2009/0232849 A1* | 9/2009 | Gallez et al. ............... 424/239.1 |
| 2009/0259176 A1 | 10/2009 | Yairi |
| 2009/0317759 A1 | 12/2009 | Groman |
| 2010/0087806 A1 | 4/2010 | Da Silva et al. |
| 2010/0111854 A1 | 5/2010 | Boyden et al. |
| 2010/0133195 A1* | 6/2010 | Gane et al. ............... 210/667 |
| 2010/0298760 A1 | 11/2010 | Olle et al. |
| 2011/0150765 A1 | 6/2011 | Boyden et al. |
| 2011/0277679 A1 | 11/2011 | Good et al. |

OTHER PUBLICATIONS

Hansen, T.C., et al., "Modelling ice Ic of different origin and stacking-faulted hexagonal ice using neutron powder diffraction data", 2006, Physics and Chemistry of Ice: proceedings of the 11th International Conference on the Physics and Chemistry of Ice held at Bremerhaven, pp. 1-8.*

Kidshealth.org, "Dehydration", 2002, source http://replay.waybackmachine.org/20021117135207/http://endoflifecare.tripod.com/juvenilehuntingtonsdisease/id51.html, pp. 1-5.*

Minaev, V.S., et al., "Polymorphous-crystallaoid nature of vitreous and liquid H2O", 2004, Journal of Optoelectronics and Advanced Materials, 6, pp. 103-112.*

Moffatt, et al., "Uptake characteristics of NGR-coupled stealth PEI/pDNA nanoparticles loaded with PLGA-PEG-PLGA tri-block copolymer for targeted delivery to human monocyte-derived dendritic cells", 2006, International Journal of Pharmaceutics, 321, pp. 143-154.*

Oechger, H., et al., "Atmospheric CO2 content in the past deduced from ice-core analyses", 1982, Annal of Glaciology, 3, pp. 227-232.*

Clath rate, Mirriam-Webster, accessed Jan. 3, 2012, accessed from: http://www.merriam-webster.com/dictionary.clathrate, pp. 1-2.*

Hervig, M., et al., "First confirmation that water ice is the primary component of polar mesopheric clouds", 2001, Geophys. Res. Lett., 28, pp. 971-974.*

"Martian Snowflakes", located at: http://www.exo.net/~pauld/Mars/4snowflakes/martiansnowflakes.html, accessed Nov. 14, 2011, pp. 1-11.*

Mainz, "Characterization of inclusions and their distribution in natural and artificial ice samples by synchrotron cryo-micro-tomography (SCXRT)", 2007, dissertation, pp. 1-121.*

Chen, S., et al., "In-situ Observations of Snow Sublimation using Scanning Electron Microscopy", 2009, 66th Eastern Snow Conference, pp. 5-9.*

Platt, U.F., et al., "Measurement of Nitrate Radical Concentrations in Continental Air", 1984, Environ. Sci. Technol., 18, pp. 365- 369.*

(56) References Cited

OTHER PUBLICATIONS

Fischer, R.G., et al., "Levels and pattern of alkyl nitrates, multifunctional alkyl nitrates, and halocarbons in the air over the Atlantic Ocean", 2000, Journal of Geophysical Research, 105, pp. 14,473-14,494.*

Law, M., "A 100-year-old Mystery: Nitrate Tolerance", 2003, HKPJ, 12(3). pp. 117.*

Precursor, located at: http://www.audioenglish.net/dictionary/precursor.htm, accessed Nov. 14, 2011, pp. 1-2.*

Currie, L.A., et al., "Long range transport of biomass aerosol to Greenland: Mutli-spectroscopic investigation of particles deposited in the snow",2005, J. RadioAnalytical and Nuclear Chemistry, 263, pp. 399-411.*

MIStupid, "Compostion of Air", located at:http://mistupid.com/chemistry/aircomp.htm, accessed Nov. 14, 2011, pp. 1-2.*

Gelderblom, H., et al., "Disposition of [G-3H]Paclitaxel and Cremophor El in a Patient With Severely Impaired Renal Function", 1999, Drug Metabolism and Disposition, pp. 1300-1305.*

Ansiaux, R., et al., "Use of botulinum toxins in cancer therapy", 2007, Expert Opinion in Investig. Drugs, pp. 209-218.*

Azbarzadeh, A., et al., "Liposome: classification, preparation, and applications", 2013, Nanoscale Res. Let., pp. 1-9.*

Wenk, M.R., et al., "Paclitaxel Partitioning into Lipid Bilayers", 2000, J. Pharm Sci., pp. 228-231.*

Amorij, J-P. et al.; "Expert Review: Development of Stable Influenza Vaccine Powder Formulations: Challenges and Possibilities"; Pharmaceutical Research; dated. Jun. 2008; pp. 1256-1273; vol. 25, No. 6; The Authors.
Amorij; J-P. et al.; "Pulmonary Delivery of an Inulin-Stabilized Influenza Subunit Vaccine Prepared by Spray-Freeze Drying Induces Systemic, Mucosal Humoral as Well as Cell-Mediated Immune Response in BALB/c Mice"; Vaccine; dated 2007; pp. 8707-8717; vol. 25; Elsevier Ltd.; located at; www.sciencedirect.com.
"Building Pykrete (Bulletproof Ice)"; Instructables; pp. 1-4; located at: http://www.instructables.com/id/Building/Pykrete-bulletproof-ice/.
Choukroun, Mathieu et al.; "Thermodynamic Model for Water and High-Pressure Ices Up to 2.2 GPa and Down to the Metastable Domain"; The Journal of Chemical Physics; dated 2007; pp. 124506.1-11; vol. 127; American Institute of Physics; located at: http://jcp.aip.oraijcp/copyright.jsp.
"Cubic Ice (Ice Ic)"; Water Structure and Science; pp. 1-7; printed on Jul. 24, 2008; located at; http://www.lsbu.ac.uk/water.
Debenedetti, Pablo G. et al.; "Supercooled and Glassy Water"; Physics Today; dated Jun. 2003; pp. 40-46; American Institute of Physics; located at: http://polymer.bu.edu/hes/articles/ds03.pdf.
Fernandez-Prini, Roberto et al.; "Aqueous Solubility of Volatile Nonelectrolytes"; Aqueous Systems at Elevated Temperatures and Pressures: Physical Chemistry in Water, Steam and Hydrothermal Solutions; dated 2004; pp. 73-98; Chapter 3; Elsevier Ltd. (abstract attached).
Garmise, Robert et al.; "Novel Dry Powder Preparations of Whole Inactivated Influenza Virus for Nasal Vaccination"; AAPS PharmSciTech; dated 2007; pp. E1-E9; vol. 8, No. 4, Article 81; located at: http://www.aapspharmscitech.org.
Hallbrucker, Andreas et al.; "Glass-Liquid Transition and Enthalpy of Devitrification of Annealed Vapor-Deposited Amorphous Solid Water. A Comparison with Hyperquenced Glassy Water"; Journal of Physical Chemistry; dated 1989; pp. 4986-4990; vol. 93; American Chemical Society.
Huber, Rudolf Maria et al.; "Palliative Endobronchial Brachytherapy for Central Lung Tumors: A Prospective, Randomized Comparison of Two Fractionation Schedules"; Chest; dated 1995; pp. 463-470; vol. 107; American College of Chest Physicians.
"Ice Structures"; pp. 1-11; located at; http://www.uwgb.edu/dutchs/PETROLGY/Ice%20Structure.HTM.
"Inkjet Printer"; Wikipedia, the Free Encyclopedia; pp. 1-5; located at; http://en.wikipedia.org/wiki/Inkjet_printer.
Ivanov, E.V. et al.; "Specific Features of Hydration of Gaseous Nitrogen and Oxygen, Revealed from Data on Their Solubility in Water H/D Isotopomers"; Russian Journal of General Chemistry; dated 2005; pp. 1851-1856; vol. 75, No. 12; Pleiades Publishing, Inc.
Ivanov, E.V. et al.; "Structural Contribution to the Effect of Hydrophobic Hydration of Noble Gases"; Journal of Structural Chemistry; dated 2005; pp. 253-263; vol. 46, No. 2; Springer Science+FBusiness Media, Inc.
Jankovic, J.; "Review: Botulinum Toxin in Clinical Practice"; Journal of Neurol Neurosurgery Psychiatry; dated 2004; pp. 951-957; vol. 75; located at: www.jnnp.com.
Johari, G.P. et al.; "Calorimetric Study of Pressure-Amorphized Cubic Ice"; Journal of Physical Chemistry; dated 1990; pp. 1212-1214; vol. 94; American Chemical Society.
Johari, G.P.; "Water's Size-Dependent Freezing to Cubic Ice"; The Journal of Chemical Physics; dated 2005; pp. 1945404.1-5; vol. 122; American Institute of Physics.
Kamps, Bernd Sebastian et al.; "Influenza Report"; dated 2006; pp. 1-225; located at: www.influenzareport.com/download.htm.
Kamrani, S. et al.; "Effect of Reinforcement Volume Fraction on Mechanical Alloying of Al—SiC Nanocomposite Powders"; Powder Metallurgy; dated Sep. 2007; pp. 276-282; vol. 50, No. 3; Maney Publishing (abstract attached).
"Kevlar Aramid Fiber: Technical Guide"; pp. 1-32.
Kippax, Paul; "Measuring Particle Size Using Modern Laser Diffraction Techniques"; Chemie.De; pp. 1-2; located at: http://www.chemeurope.com/articles/e/61205/?WT.mc_id=ca0102.
Klotz, Stefan et al.; "In Situ Neutron Diffraction Studies of High Density Amorphous Ice Under Pressure"; Journal of Physics Condensed Matter; dated 2005; pp. S967-S974; vol. 17; IOP Publishing Ltd.
Kumar, Ritesh et al.; "Review Article: Modified Transdermal Technologies: Breaking the Barriers of Drug Permeation via the Skin"; Tropical Journal of Pharmaceutical Research; dated Mar. 2007; pp. 633-644; vol. 6, No. 1; Pharmacy Group; located at: http://www.tjpr.org.
Loerting, Thomas et al.; "Tropical Review: Amorphous Ices: Experiments and Numerical Simulations"; Journal of Physics: Condensed Matter; dated 2006; pp. R919-R977; vol. 18; IOP Publishing Ltd.
"Lung Cancer"; Wikipedia, the Free Encyclopedia; pp. 1-21; located at: http://en.wikipedia.org/wiki/Lung_cancer.
Menon, G.K. et al.; "Particle-Mediated Gene Delivery and Human Skin: Ultrastructural Observations on Stratum Corneum Barrier Structures"; Skin Pharmaclogy and Physiology: dated 2007; pp. 141-147; vol. 20; Karger AG, Basel.
Murray, Benjamin J. et al.; "Formation and Stability of Cubic Ice in Water Droplets"; Physical Chemistry Chemical Physics; dated 2006; pp. 186-192; vol. 8; The Owner Societies.
Murthy, S. Narasimha et al.; "pH Influences the Postpulse Permeability State of Skin After Electroporation"; Journal of Controlled Release; dated 2003; pp. 49-57; vol. 93; Elsevier B.V.; located at: www.sciencedirect.com.
Nixon, W.A. et al.; "Flexural Strength of Sand-Reinforced Ice"; Journal of Cold Regions Engineering; Mar. 1991; pp. 14-27; vol. 5, Issue 1; American Society of Civil Engineers (abstract attached).
Ohtaki, Hitoshi; "Effects of Temperature and Pressue on Hydrogen Bonds in Water and in Formamide"; Journal of Molecular Liquids; dated 2003; pp. 3-13; vol. 103-104; Elsevier Science B.V.; located at; www.elsevier.com/locate/molliq.
"On Air"; Messer; dated Feb. 2007; pp. 1-16; vol. 2; located at; www.messer.si/Revija_On_air/C_Visual_On_Air2ang.pdf.
Paolino, Donatella et al.; "Drug Delivery Systems"; Encyclopedia of Medical Devices and Instrumentation: $2^{nd}$ Edition; dated 2006; pp. 437-495; John Wiley & Sons, Inc.
"Physical Properties of Ice"; Snow Crystals.com; pp. 1-3; located at http://www.its.caltech.edu/~atomic/snowcrystals/ice/ice.htm.
Pennings, A.J. et al.; "Polyethylene: High-Speed Gel-Spinning of Ultra-High Molecular Weight Polyethylene"; Polymer Bulletin; dated 1986; pp. 167-174; vol. 16;. Springer-Verlag.
"Pykrete"; Wikipedia, the Free Encyclopedia; pp. 1-6; located at; http://en.wikipedia.org/wiki/Pykrete.
Roberts, MS; "Targeted Drug Delivery to the Skin and Deeper Tissues: Role of Physiology, Solute Structure and Disease"; Clinical and Experimental Pharacology and Physiology: Annual Scientific Meeting of ASCEPT; dated 1996; pp. 874-879; vol. 24.

(56) References Cited

OTHER PUBLICATIONS

Spiro, Stephen G. et al.; "Centennial Review : One Hundred Years of Lung Cancer"; American Journal of Respiratory and Critical Care Medicine; dated 2005; pp. 523-529; vol. 172.

Tang, Hua et al.; "Research Paper: An Investigation of the Role of Cavitation in Low-Frequency Ultrasound-Mediated Transdermal Drug Transport"; Pharmaceutical Research; dated Aug. 2002; pp. 1160-1169; vol. 19, No. 8; Plenum Publishing Corporation.

Vergnon, J.-M. et al.; "Place of Cryotherapy, Brachytherapy and Photodynamic Therapy in Therapeutic Bronchoscopy of Lung Cancers"; European Respiratory Journal; dated 2006; pp. 200-218; vol. 28, No. 1; ERS Journals Ltd.

Wernet, PH. et al.; "Spectroscopic Characterization of Microscopic Hydrogen-Bonding Disparities in Supercritical Water"; The Journal of Chemical Physics; dated 2005; pp. 154503.1-7; vol. 123; American Institute of Physics.

Wolpin, Brian M.; "Adjuvant Treatment of Colorectal Cancer"; CA: A Cancer Journal for Clinicians; dated 2007; pp. 168-185; vol. 57; American Cancer Society, Inc.; located at: www.caonline. amcancersoc.org.

Yasui, Minami et al.; "Experimental Study on the Rate Dependent Strength of Ice-Silica Mixture with Silica Volume Fractions Up to 0.63"; Geophysical Research Letters; dated 2008; pp. L12206.1-5.

Zhang, W.X. et al.; "Selected Crystallization of Water as a Function of Size"; Chemical Physics Letters; dated 2006; pp. 251-255; vol. 421; Elsevier B.V.; located www.sciencedirect.com.

Zheligovskaya, E.A. et al.; "Crystalline Water Ices"; Russian Chemical Reviews; dated 2006; pp. 57-76; vol. 75, No. 1; Russian Academy of Sciences and Turpion Ltd.

Berman, S. et al.; "Tracking stem cells using magnetic nanoparticles"; WIREs Nanomedicine and Nanobiotechnology; Jul./Aug. 2011; pp. 343-355; vol. 3; John Wiley & Sons, Inc.

Bourgeois, Jocelyne C..; "Seasonal and interannual pollen variability in snow layers of arctic ice caps"; Review of Palaeobotany & Palynology; 2000; pp. 17-36; vol. 108; Elsevier Science B.V.

Clinical Trial; Pharmaceutical Medicine Dictionary; 2001; one page; located at; http://www.credoreference.cornlentry/pmd/clinical_trial retrieved online on Sep. 18, 2011.

eco-usa.net; "Benzene"; eco-usa.net; pp. 1-4; printed on Oct. 24, 2011; located at: http://www.eco-usa.net/toxics/chemicals/benzene.shtml; Information is excerpted from: "Toxicological Profile for Benzene, 2005 Draft for Public Comment"; Agency for Toxic Substances and Disease Registry, United States Public Health Service.

Kluz, K. et al.; "Application of ice-air jet blasting in treatment of sensitive surfaces"; Int. J. Abrasive Technology; May 30, 2007; pp. 59-77; vol. 1, No. 1; Inderscience Enterprises Ltd.

Mayo Clinic; "Impacted wisdom teeth"; mayoclinic.com special in association with cnn.com; Health/Library; Apr. 21, 2006; printed on Oct. 3, 2011; 4 pages; located at http://premium.asia.cnn.com/HEALTH/library/DS/00679.html.

MIStupid; "Composition of Air"; MIStupid.com; pp. 1-2; printed on Oct. 3, 2011; located at: http://mistupid.com/chemistry/aircomp.htm.

Pacini, E. et al.; "Pollen carbohydrates and water content during development, presentation, and dispersal: a short review"; Protoplasma; published Aug. 31, 2006; pp. 73-77; vol. 228; Springer-Verlag.

Sasaki, A. et al.; "Bisphosphonate Risedronate Reduces Metastatic Human Breast Cancer Burden in Bone in Nude Mice"; Cancer Research; Aug. 15, 1995; pp. 3551-3557; vol. 55; American Association for Cancer Research.

Shaw, G. et al.; "Chemical Studies on the Constitution of Some Pollen and Spore Membranes"; Grana Palynologica; published 1964; printed on Oct. 23, 2011; pp. 247-252 (& cover information, 2 pages); vol. 5, No. 2; Taylor & Francis Informa Ltd.

Taylor, C. H.; "Cancer"; 1915; p. 64; Lea & Febiger.

Toshiyuki, O. et al.; "Dermabrasion Technique for Peri-implant Soft Tissue Management in the Mandible Reconstructed by Free Osteocutaneous Flap"; Science Links Japan; 2004; pp. 1-2; Nippon Koku Inpuranto Gakkaishi; printed on Oct. 3, 2011; located at http://sciencelinks.jp/j-east/article/200424/000020042404A0800133.php.

Warts; Black's Medical Dictionary, $42^{nd}$ Edition; 2010; one page; retrieved on Sep. 18, 2011; located at: http://www.credoreference.com/entry/blackmed/warts; A & C Black Publishers Ltd.

Wilhardt, M. et al.; "National PBM Drug Monograph Papain-Urea (Accuzyme®) and Papain-Urea-Chlorophyllin Copper Complex Sodium (Panafil®)"; 10 pages; Jan. 2004; located at: http://www.vapbm.org or http://vaww.pbm.med.va.gov.

Abnet, Christian C. et al.; "Zinc Concentration in Esophageal Biopsy Specimens Measured by X-Ray Fluorescence and Esophageal Cancer Risk"; Journal of the National Cancer Institute, bearing a date of Feb. 15, 2005; pp. 301-306; vol. 97, No. 4; Oxford University Press.

Herman, F. A. et al.; "Total Mineral Material, Acidity, Sulphur and Nitrogen in Rain and Snow at Kentville, Nova Scotia"; Tellus; bearing a date of 1957; pp. 180-183; vol. IX, No. 2.

Definition from Hutchinson Unabridged Encyclopedia with Atlas and Weather guide; "Polymers"; The Hutchinson Unabridged Encyclopedia with Atlas and Weather guide; Jul. 15, 2011; total of 3 pages; located at: http://www.credoreference.com/entry/heliconhe/polymers; © 2010 Helicon Publishing/RM.

Definition from The Crystal Reference Encyclopedia; "Horse"; The Crystal Reference Encyclopedia; Jul. 15, 2011; total of 1 page; located at: http://www.credoreference.com/entry/cre/horse; Crystal Semantics Ltd.

Kidshealth.org; "Dehydration"; bearing a date of 2002; located at: http://endoflifecare.tripod.com/juvenilehuntingtondisease/id51.html ; printed on Mar. 17, 2011; pp. 1-5.

Butler, A.R. et al.; "Therapeutic Uses of Inorganic Nitrite and Nitrate: From the Past to the Future"; Circulation; bearing a date of 2008; pp. 2151-2159; vol. 117; Journal of the American Heart Association.

Schmidt, A.I. et al.; "Exposure to carbon dioxide and helium reduces in vitro proliferation of pediatric tumor cells"; Pediatric Surgical Int. bearing a date of 2006; pp. 72-77; vol. 22; Springer-Verlag.

Oeschger, H. et al.; "Atmospheric $CO_2$ Content in the Past Deduced From Ice-Core Analyses"; Annals of Glaciology; bearing a date of 1982; pp. 227-232; vol. 3; International Glaciological Society.

Edwards, R. et al.; "Iron in East Antarctic snow: Implications for atmospheric iron deposition and algal production in Antarctic waters"; Geophysical Research Letters; bearing a date of 2001; 1 page; vol. 28; No. 20; American Geophysical Union (Abstract only).

Uauy, C. et al.; "A NAC Gene Regulating Senescence Improves Grain Protein, Zinc, and Iron Content in Wheat"; Science; bearing a date of Nov. 24, 2006; pp. 1298-1301; vol. 314; No. 1298; American Association for the Advancement of Science.

Bertie, J. E. et al.; "Transformations of Ice II, Ice III, and Ice V at Atmospheric Pressure"; The Journal of Chemical Physics; bearing a date of Feb. 15, 1963; pp. 840-846; vol. 38, No. 4; Journal of Chemical Physics.

Buck, Christopher B. et al.; "Carrageenan Is a Potent Inhibitor of Papillomavirus Infection"; PLoS Pathogens; bearing a date of Jul. 2006; pp. 0671-0680; vol. 2, Issue 7; PLoS Pathogens.

Definition from Dorland's Illustrated Medical Dictionary "Nanoparticle"; bearing a date of 2007; Feb. 10, 2011; total of 1 page; Elsevier; located at: www.credoreference.com/entry/ehsdorland/nanoparticle.

Goodman, J. M.; "Liquid Nitrogen Therapy of Warts and Other Skin Lesions"; Canad. M. A. J.; bearing a date of Mar. 19, 1960; pp. 628-630; vol. 82.

Want, Roy; "RFID: A Key to Automating Everything"; Scientific American; bearing a date of Jan. 2004, printed on Feb. 21, 2004; pp. 1-10; vol. 290, No. 1; Scientific American.

Al-Amoudi A. et al.; "Amorphous solid water produced by cryosectioning of crystalline ice at 113 K"; J. Microsc.; Aug. 2002; pp. 146-153; vol. 207 (Pt 2); (Abstract Only).

Barnes, Piers R.F. et al.; "Distribution of soluble impurities in cold glacial ice"; Journal of Glaciology; Jun. 2004; pp. 311-324(14); vol. 50, No. 170; (Abstract Only).

McFeeters, Roger F.; "Single-Injection HPLC Analysis of Acids, Sugars, and Alcohols in Cucumber Fermentations"; J. Agric. Food Chem.; 1993; pp. 1439-1443; vol. 41, No. 9.

(56) References Cited

OTHER PUBLICATIONS

Melville, Kate; "The incredible noise of snow flakes!"; scienceagogo.com; Mar. 16, 2000; pp. 1-3; located at http://www.scienceagogo.com/news/20000216171241data_trunc_sys.shtml.

Painter, Thomas H. et al.; "Detection and Quantification of Snow Algae with an Airborne Imaging Spectrometer"; Applied and Environmental Microbiology; Nov. 2001; pp. 5267-5272 plus cover page; vol. 67, No. 11; American Society for Microbiology.

Raman, Chandrashekar et al.; "Modeling small-molecule release from PLG microspheres: effects of polymer degradation and nonuniform drug distribution"; Journal of Controlled Release; bearing a date of Dec. 7, 2004; pp. 149-158; vol. 103; Elsevier B.V.

Singh, Manmohan et al.; "Charged polylactide co-glycolide microparticles as antigen delivery systems"; Expert Opin. Biol. Ther.; 2004; pp. 483-491; vol. 4, No. 4; Ashley Publications Ltd.

Babicki, A. et al.; "Evaluation of using fibrin tissue adhesive (Beriplast) and preparations of thrombin and adrenalin in injection hemostatis methods for gastric and duodenal ulcer hemorrhage. Randomized, prospective clinical trial"; Wiad Lek; 1997; pp. 2:383-7; 50 Suppl 1 Pt; PubMed (Abstract Only).

Belitsky, Rosalind B. et al.; "Evaluation of the Effectiveness of Wet Ice, Dry Ice, and Cryogen Packs in Reducing Skin Temperature"; Physical Therapy; Jul. 1987; pp. 1080-1084; vol. 67, No. 7.

Currie, L. A. et al.; "Long range transport of biomass aerosol to Greenland: Multi-spectroscopic investigation of particles deposited in the snow"; Journal of Radioanalytical and Nuclear Chemistry; 2005; pp. 399-411; vol. 263, No. 2; Akadémiai Kiadö, Budapest.

Escámez, Maria José et al.; "An In Vivo Model of Wound Healing in Genetically Modified Skin-Humanized Mice"; The Journal of Investigative Dermatology; Dec. 6, 2004; pp. 1182-1191; vol. 123; The Society for Investigative Dermatology, Inc.

Kennedy, Muiris T. et al.; "Hypertonic saline reduces inflammation and enhances the resolution of oleic acid induced acute lung injury"; BMC Pulmonary Medicine; Jul. 8, 2008; pp. 1-7; vol. 8, Issue 9; BioMed Central Ltd.

Lin, Hwai-Jeng et al.; "Endoscopic injection with fibrin sealant versus epinephrine for arrest of peptic ulcer bleeding: a randomized, comparative trial"; Journal of Clinical Gastroenterology; 2002; pp. 218-221; vol. 35, Issue 3; PubMed (Abstract Only).

"Martian Snowflakes"; exo.net; printed on Nov. 14, 2011; 11 pages; located at http://www.exo.net/~pauld/Mars/4snowflakes/martiansnowflakes.html.

"Precursor"; AudioEnglish.net; printed on Nov. 14, 2011; 2 pages; located at http://www.audioenglish.net/dictionary/precursor.htm.

Rifkin, Barry R. et al.; "Osteoid Resorption by Mononuclear Cells in vitro"; Cell and Tissue Research; 1980; pp. 493-500; vol. 210; Springer-Verlag.

"Snow", wikipedia.org; printed on Nov. 14, 2011; 18 pages; located at http://en.wikipedia.org/wiki/Snow.

"A Guide to Snowflakes"; SnowCrystals.com; printed on May 19, 2012; 10 pages; located at http://www.its.caltech.edu/~atomic/snowcrystals/class/class.htm.

Berleant, Daniel; "New Plant Paradigms (Part X: Power Plants, Greening the Desert, Phyto-Terraforming, and Recommendations)"; Lifeboat News: The Blog; Sep. 19, 2010; 3 pages; located at http://lifeboat.com/blog/2010/09/new-plant-paradigms-part-x-power-plants-greening-the-desert-phyto-terraforming-and-recommendations.

"Bullet"; definition of Bullet; dictionary.reference.com; printed on May 19, 2012; 4 pages; located at http://dictionary.reference.com/browse/bullet.

Campo et al.; "Super-exchange interactions enhanced through spin delocalisation in $K_2FeCl_5 \cdot H_2O$"; Scientific Highlights; bearing a date of 2002; pp. 18-19; located at http://www.unizar.es/icma/depart/termomag/lineas/h11.pdf.

"Cryonomic Dry Ice Cleaning Technology"; Cryonomic; bearing a date of 2006; ; 2 pages; located at http://www.cryonomic.ro/produse.php?lang=en&p_id=2.

"Fixative"; definition of Fixative; TheFreeOnlineDictionary.com; printed on May 19, 2012; 2 pages; located at http://www.thefreedictionary.com/fixative.

"Freeze"; definition of Freeze; American Heritage Dictionary; printed on May 19, 2012; 6 pages; located at http://www.answers.com/topic/freeze.

"Freeze-Dry"; The Penguin English Dictionary; bearing a date of 2000, 2003; 2 pages; Penguin Books.

Gromball, F.; "Nanometer-Scale Height Measurements in Micromachined Picoliter Vials Based on Interference Fringe Analysis"; ACM Digital Library (US Patent & Trademark Office); bearing a date of 2000; 1 page; located at http://dl.acm.org/citation.cfm?id=877015.

Minnery, John; "Kill Without Joy! The Complete How to Kill Book"; bearing a date of 1992; cover page, publication information, and p. 149; Paladin Press.

"Robot"; definition of Robot; TheFreeOnlineDictionary.com; printed on May 7, 2012; 3 pages; located at http://www.thefreedictionary.com/robot.

Ryalls, Charles Wager; Transactions of the National Association for the Promotion of Social Science; Glasgow Meeting, 1874; bearing dates of 1874 and 1875; 2 pages; Longmans, Green, and Co., London.

Tamai et al.; "Percutaneous injection of a low-concentration alkaline solution targeting hepatocellular carcinoma"; Oncol. Rep.; bearing a date of Jul.-Aug. 2000; pp. 719-23; vol. 7, No. 4; located at http://www.ncbi.nlm.nih.gov/pubmed/10854532 (abstract only—1 page).

Wiseman, John "Lofty"; "The Ultimate Survival Guide"; bearing dates of 1986, 1993, 2004; cover page, copyright page and p. 140; Harper-Collins Publishers Inc.

Adams et al.; "Update in Vitamin D"; J Clin Endocrinol Metab; bearing a date of Feb. 2010; pp. 471-478; vol. 95, No. 2; The Endocrine Society.

Armstrong et al.; "Vasodilator Therapy in Acute Myocardial Infarction. A Compassion of Sodium Nitoprusside and Nitroglycerin"; Circulation, Journal of the American Heart Association; bearing a date Dec. 1975; pp. 1118-1122 and 1 cover-page; vol. 52; American Heart Association; Dallas, TX.

Cornell University Cooperative Extension; "Water Quality Information for Consumers"; accessed at http://waterquality.cce.cornell.edu/bottled/htm; accessed on Mar. 14, 2012; pp. 1-6; Cornell University.

"Dynamite"; Classic Encyclopedia 1911; located at http://1911encylopedia.org/Dynamite; printed on May 5, 2012; pp. 1-2.

Holmes et al.; "Nitroglycerin: The Explosive Drug"; Journal of Chemical Education; bearing a date of Sep. 1971; pp. 573-576; vol. 48, No. 9.

Leroux et al.; "Biodegradable Nanoparticles—From Sustained Release Formulations to Improved Site Specific Drug Delivery"; Journal of Controlled Release; bearing a date of 1996; pp. 339-350; vol. 39; Elsevier Science B. V.

Murray, Benjamin J.; "Enhanced Formation of Cubic Ice in Aqueous Organic Acid Droplets"; Environmental Research Letters; published May 30, 2008; pp. 1-7; vol. 3; IOP Publishing Ltd.

Nasa Tech Brief; "Tools Made of Ice Facilitate Forming of Soft, Sticky Materials"; Brief 69-10199; bearing a date of Jun. 1969; pp. 1-2.

Nomura et al.; "Interaction of Water with Native Collagen"; Biopolymers; bearing a date of 1977: pp. 231-246; vol. 16; John Wiley & Sons, Inc.

Overholt et al.; "Photodynamic Therapy with Porfimer Sodium for Ablation of High-Grade Dysplasia in Barrett's Esophagus; International, Partially Blinded, Randomized Phase III Trial (CME)": Gastrointestinal Endoscopy; bearing a date of 2005; pp. 488-498; vol. 62, No. 4; The American Society for Gastrointestinal Endoscopy.

RxList; "Nystatin and Triamcinoline Acetonide"; located at http://www.rxlist.com/nystatin-and-triamicinolone-acetonide-drug.htm; printed on Mar. 10, 2012; pp. 1-3; WebMD, LLC.

Vogl et al.; "Colorectal Carcinoma Metastases in Liver: Laser-Induced Interstitial Thermotherapy—Local Tumor Control Rate and Survival Data"; Radiology; bearing a date of 2004; pp. 450-458; vol. 230, No. 2; RSNA.

(56) References Cited

OTHER PUBLICATIONS

Wissner-Goss et al.; "Diamond Stabilization of Ice Multilayers at Human Body Temperature"; Physical Review E; published on Aug. 27, 2007; pp. 020501-1 through 020501-4; vol. 76, No. 020501(R); The American Physical Society.
Ali et al.; "Lid for a Vacuum Line Cooling Trap"; J. Chem. Educ.; bearing a date of Jun. 1995; p. 549; vol. 72, No. 6.
"Dell Precision™ Workstation 650"; Product brochure,; bearing a date of Nov. 2002; pp. 1-2; Dell Computer Corporation.
He et al.; "A Virtual Prototype Manufacturing Software System for Mems"; International Workshop on Micro Electromechanical Systems,; bearing a date of 1996; pp. 122-126; IEEE.
Henry et al.; "Microfabricated Microneedles: A Novel Approach to Transdermal Drug Delivery"; Journal of Pharmaceutical Sciences; bearing a date of Aug. 1998; pp. 922-925; vol. 87, No. 8; American Chemical Society and American Pharmaceutical Association.
McAllister et al.; "Microfabricated Microneedles for Gene and Drug Delivery"; Annual Review of Biomedical Engineering; bearing a date of 2000; pp. 289-313; Annual Reviews.
McAllister et al.; "Microfabricated Needles for Transdermal Delivery of Macromolecules and Nanoparticles: Fabrication Methods and Transport Studies"; Proceedings of the National Academy of Sciences USA; bearing a date of Nov. 25, 2003; pp. 13755-13760; vol. 100, No. 24; The National Academy of Sciences of the USA.
Gorman et al.; Effects of Topical Nitroglycerin and Flurbiprofen in the Rat Comb Burn Model; Annals of Plastic Surgery; May 1999; 1 page (abstract only); Lippincott Williams & Wilkins, Inc.
Ito et al.; "Evaluation of self-dissolving needles containing low molecular weight heparin (LMWH) in rats"; International Journal of Pharmaceutics; bearing a date of 2008; available online Aug. 6, 2007; pp. 124-129; vol. 349; Elsevier B. V.
Nagourney, Eric; "Vital Signs: Sensations; A Needle on Ice to Ease the Pain"; The New York Times; Oct. 16, 2001; 2 pages; located online at : http://www.nytimes.com/2001/10/16/health/vital-signs-sensations-a-needle-on-ice-to-ease-the-pain.html ; The New York Times Company.
Van Baare et al.; "Microbiological Evaluation of Glycerolized Cadaveric Donor Skin"; Transplantation; bearing a date of Apr. 15, 1998; pp. 1-7 (966-970); vol. 65, No. 7; Williams & Wilkins.
Bellissent-Funel, M-C; "Structure of confined water"; Journal of Physics: Condensed Matter; bearing a date of 2001; pp. 9165-9177; vol. 13; IOP Publishing Ltd.
Brayden, David J.; "Oral vaccination in man using antigens in particles: current status"; European Journal of Pharmaceutical Sciences; bearing a date of 2001; pp. 183-189; vol. 14; Elsevier Science B.V.
Davis et al.; "Significant Improvement of Stiff-Person Syndrome After Paraspinal Injection of Botulinum Toxin A"; Movement Disorders; bearing a date of 1993; pp. 371-373; vol. 8, No. 3; Movement Disorder Society.
dE Berrazueta et al.; "Effect of transdermal nitroglycerin on inflammatory mediators in patients with peripheral atherosclerotic vascular disease"; American Heart Journal; bearing a date of Oct. 2003; pp. 1-6; vol. 146, No. 14; Mosby, Inc.
Du et al.; "Functional reconstruction of rabbit corneal epithelium by human limbal cells cultured on amniotic membrane"; Molecular Vision; bearing a date of 2003; pp. 1-16; vol. 9.
Fuchsluger et al.; "Rate of epithelialization and re-operations in corneal ulcers treated with amniotic membrane transplantation combined with botulinum toxin-induced ptosis"; Graefe's Arch Clin Exp Ophthalmol; bearing a date of Jan. 12, 2007; pp. 955-964; vol. 245; Springer-Verlag.
Kweon et al.; "A Nontoxic Chimeric Enterotoxin Adjuvant Induces Protective Immunity in Both Mucosal and Systemic Compartments with Reduced IgE Antibodies"; The Journal of Infectious Diseases; bearing a date of 2002; pp. 1261-1269; vol. 186; Infectious Diseases Society of America.
Meinert, Curtis L.; "Clinical Trials, Overview"; Encyclopedia of Biostatistics ; bearing a date of 2005; pp. 1-15.

Satoh et al.; "Effects of Anti-Inflammatory Drugs on Triple Vaccine-Induced Pleurisy in Rats"; Japan. J. Pharmacol.; bearing a date of 1982; pp. 909-919; vol. 32.
Simon et al.; "Phase II Trials"; *Encyclopedia of Biostatistics*, Online; bearing a date of 2005; pp. 1-6; John Wiley & Sons, Ltd.
Storer, Barry E.; "Phase I Trials"; *Encyclopedia of Biostatistics*, Online; bearing a date of 2005; pp. 1-5; John Wiley & Sons, Ltd.
Usami et al.; "An SOI-Based 7.5 µm-Thick 0.15×0 15mm$^2$ RFIDChip"; International Solid State Circuits Conference 2006/Session 17/RFID and RF Directions/17.1; bearing a date of Feb. 7, 2006; pp. 1-3; IEEE.
Usami, M.; "Ultra-Small RFID Chip Technology"; IEEE International Conference Electronic Circuits Syst; bearing a date of 2006; pp. 708-711; IEEE.
Walker, Glenn A.; "Common Statistical Methods for Clinical Research with SAS® Examples, Second Edition"; bearing a date of Jul. 2002; pp. 1-200; SAS Institute, Inc.
Bhalla, M. et al.; "Microdermabrasion: Reappraisal and Brief Review of Literature"; American Society for Dermatologic Surgery, Inc.; bearing a date of Jun. 2006; pp. 809-814; vol. 32; Blackwell Publishing.
Davari, P. et al.; "A randomized investigator-blind trial of different passes of microdermabrasion therapy and their effects on skin biophysical characteristics"; International Journal of Dermatology; bearing a date of 2008; pp. 508-513; vol. 47; The International Society of Dermatology.
Fang, J-Y. et al.; "Enhancement of topical 5-aminolaevulinic acid delivery by erbium:YAG laser and microdermabrasion: a comparison with iontophoresis and electroporation"; The British Journal of Dermatology; bearing a date of 2004; pp. 132-140; vol. 151; British Association of Dermatologists.
Grimes, P. E.; "Microdermabrasion"; The American Society for Dermatologic Surgery, Inc.; bearing a date of Sep., 2005; pp. 1160-1165; vol. 31, No. 9, Part 2; BC Decker, Inc.
Lee, Woan-Ruoh et al.; "Microdermabrasion as a Novel Tool to Enhance Drug Delivery via the Skin: An Animal Study"; The American Society for Dermatologic Surgery, Inc.; bearing a date of Aug. 2006; pp. 1013-1022; vol. 32, No. 8; Blackwell Publishing.
Rajan, P. et al.; "Skin Barrier Changes Induced by Aluminum Oxide and Sodium Chloride Microderrnabrasion"; The American Society for Dermatologic Surgery, Inc.; bearing a date of May, 2002; pp. 390-393; vol. 28, No. 5; Blackwell Publishing.
Spencer, J. M. et al.; "Approaches to Document the Efficacy and Safety of Microdermabrasion Procedure"; The American Society for Dermatologic Surgery, Inc.; bearing a date of Nov. 2006; pp. 1353-1357; vol. 32, No. 11; Blackwell Publishing.
Anisimov, Mikhail A. et al.; "Near-Critical Behavior of Aqueous Systems"; Aqueous Systems at Elevated Temperatures and Pressures: Physical Chemistry in Water, Steam and Hydrothermal Solutions; dated 2004; pp. 29-71; Chapter 2; Elsevier Ltd. (abstract attached).
Aguilar, J.C. et al.; "Vaccine Adjuvants Revisited"; Vaccine; dated 2007; pp. 3752-3762; vol. 25; Elsevier Ltd.; located at; www.sciencedirect.com.
Richerson et al.; "Modern Ceramic Engineering"; Third Edition; published 2006; 3 pages; Informa.
Balakrishnan et al.; "Evaluation of an in situ forming hydrogel wound dressing based on oxidized alginate and gelatin"; Biomaterials; Apr. 4, 2005; pp. 6335-6342; vol. 26; Elsevier Ltd.
Hollisaz et al.; "A randomized clinical trial comparing hydrocolloid, phenytoin and simple dressings for the treatment of pressure ulcers"; BMC Dermatology; Dec. 15, 2004; pp. 1-9; vol. 4, No. 18; BioMed Central Ltd.
Lee et al.; "Dissolving microneedles for transdermal drug delivery"; Biomaterials; Dec. 22, 2007; pp. 2113-2124; vol. 29; Elsevier Ltd.
Mulholland et al.; "Analysis of microparticle penetration into human and porcine skin: non-invasive imaging with multiphoton excitation microscopy"; Jun. 17, 2002; Proc. SPIE 4620, Multiphoton Microscopy in the Biomedical Sciences II; pp. 113-122.
Park et al.; "Biodegradable polymer microneedles: Fabrication, mechanics and transdermal drug delivery"; Journal of Controlled Release; Feb. 2, 2005; pp. 51-66; vol. 104; Elsevier Ltd.

(56) References Cited

OTHER PUBLICATIONS

Baxter et al.; "Jet-induced skin puncture and its impact on needle-free jet injections: Experimental studies and a predictive model"; Journal of Controlled Release; bearing a date of Jul. 5, 2005; pp. 361-373; vol. 106; Elsevier B.V.

Callaway et al.; "Energy bands in ferromagnetic iron"; Physical Review B; Sep. 1, 1977; pp. 2095-2105; vol. 16, No. 5.

Merisko-Liversidge et al.; "Nanosizing: a formulation approach for poorly-water-soluble compounds"; European Journal of Pharmaceutical Sciences; bearing a date of Nov. 18, 2002; pp. 113-120; vol. 18; Elsevier Science B.V.

Warren et al.; "A Model for the Spectral Albedo of Snow, II: Snow Containing Atmospheric Aerosols"; Journal of the Atmospheric Sciences; bearing a date of Aug. 28, 1980; pp. 2734-2745; vol. 37; American Meteorological Society.

"Building Pykrete (Bulletproof Ice)"; Instructables; pp. 1-4; located at: http://www.instractables.com/lid/Building-Pykrete-bulletproof-ice/; last accessed Mar. 24, 2015.

"Ice Structures"; pp. 1-11; located at; http://www.uwgb.edu/dutchs/PETROLGY/Ice%20Structure.HTM; last accessed Mar. 24, 2015.

"Inkjet printer"; from Wikipedia, the free encyclopedia; pp. 1-5; located at http://en.wikipedia.org/wiki/Inkjet_printer; last accessed Oct. 28, 2008.

Kippax, Paul; "Measuring Particle Size Using Modern Laser Diffraction Techniques"; Chemie.De; pp. 1-2; last accessed Mar. 24, 2015; located at: http://www.chemeurope.com/en/whitepapers/61205/measuring-particle-size-using-modern-laser-diffraction-techniques.html.

"Lung Cancer"; Wikipedia; bearing date of Aug. 22, 2011; printed on Aug. 26, 2011; pp. 1-21; located at: http://en.wikipedia.org/wiki/Lung_cancer.

"Physical Properties of Ice"; Snow Crystals.com; pp. 1-3; located at http://www.its.caltech.edu/~atomic/snowcrystals/ice/ice.htm; last accessed Nov. 6, 2008.

"Pykrete"; Wikipedia; bearing date of Aug. 24, 2011; printed on Aug. 26, 2011; pp. 1-6; located at: http://en.wikipedia.org/wiki/Pykrete.

* cited by examiner

700 A method comprising:

710 comparing information regarding at least one aspect of administering at least one frozen particle therapeutic composition to at least one subject and information regarding at least one clinical outcome following receipt by the at least one subject of at least one frozen particle therapeutic composition; and providing output information optionally based on the comparison 720 determining at least one statistical correlation 730 counting the occurrence of at least one clinical outcome 735 determining at least one correlation before the administration of the at least one frozen particle therapeutic composition 740 information regarding the amount of at least one frozen particle therapeutic composition or therapeutic agent administered to at least one biological tissue of a subject 750 information regarding at least one dimension of biological tissue penetration 760 information regarding at least one depth, width, or breadth of administration of at least one frozen particle therapeutic composition to at least one biological tissue of at least one subject 770 information regarding two or more subjects with one or more common attributes 780 genetic attributes, mental attributes, or psychological attributes 790 genotype attributes or phenotype attributes 797 at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical history; or blood condition

FIG. 8

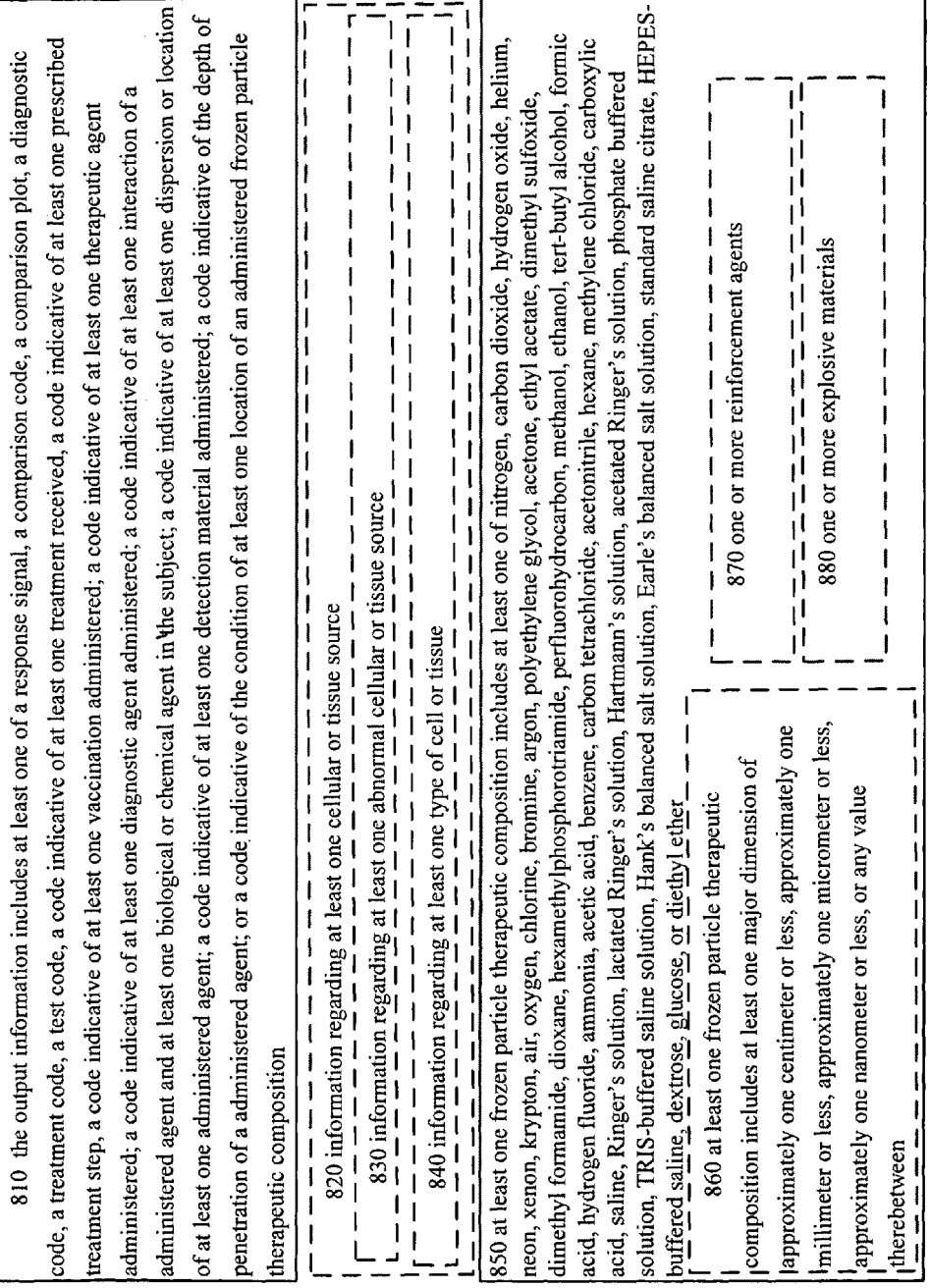

810 the output information includes at least one of a response signal, a comparison code, a comparison plot, a diagnostic code, a treatment code, a test code, a code indicative of at least one treatment received, a code indicative of at least one prescribed treatment step, a code indicative of at least one vaccination administered; a code indicative of at least one therapeutic agent administered; a code indicative of at least one diagnostic agent administered; a code indicative of at least one interaction of a administered agent and at least one biological or chemical agent in the subject; a code indicative of at least one dispersion or location of at least one administered agent; a code indicative of at least one detection material administered; a code indicative of the depth of penetration of a administered agent; or a code indicative of the condition of at least one location of an administered frozen particle therapeutic composition 820 information regarding at least one cellular or tissue source 830 information regarding at least one abnormal cellular or tissue source 840 information regarding at least one type of cell or tissue 850 at least one frozen particle therapeutic composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 860 at least one frozen particle therapeutic composition includes at least one major dimension of approximately one centimeter or less, approximately one millimeter or less, approximately one micrometer or less, approximately one nanometer or less, or any value therebetween 870 one or more reinforcement agents 880 one or more explosive materials

FIG. 9

900 receipt by the at least one subject of at least one frozen particle therapeutic composition is pursuant to at least one clinical trial 910 creating at least one inclusion criterion and at least one exclusion criterion for a clinical trial involving the at least one frozen particle therapeutic composition 920 suggesting the inclusion of one or more of the at least one subject in at least one clinical trial 930 suggesting the exclusion of one or more of the at least one subject in at least one clinical trial 940 using one or more comparisons to predict at least one clinical outcome regarding at least one second subject 950 the at least one second subject has not received the at least one frozen particle therapeutic composition 960 predicting at least one clinical outcome involving the at least one second subject, wherein the at least one second subject is a plurality of people; and segregating subject identifiers associated with the plurality of people in reference to the predicted at least one clinical outcome 970 determining the eligibility of the at least one second subject for the at least one clinical trial

FIG. 11

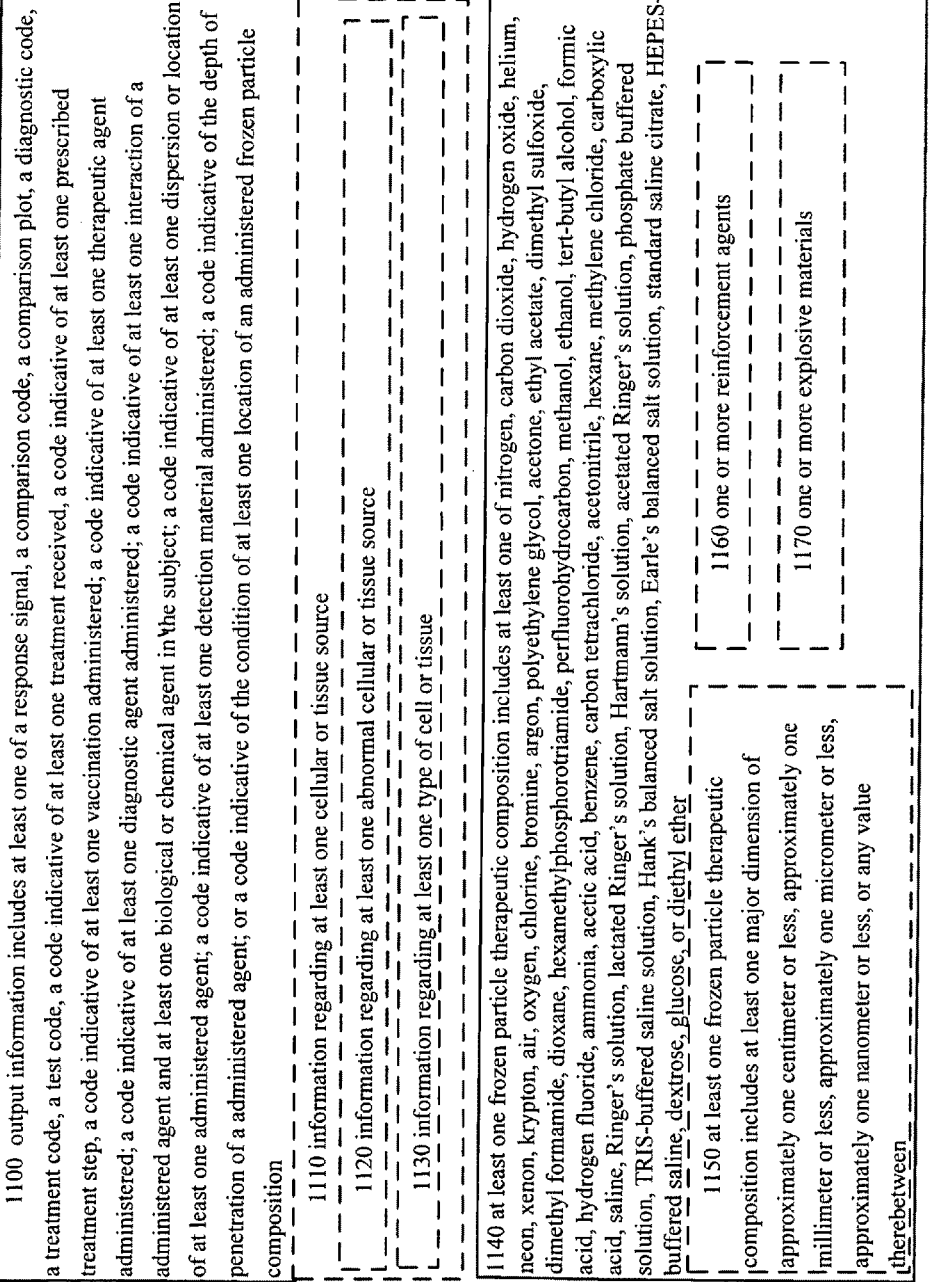

1100 output information includes at least one of a response signal, a comparison code, a comparison plot, a diagnostic code, a treatment code, a test code, a code indicative of at least one treatment received, a code indicative of at least one prescribed treatment step, a code indicative of at least one vaccination administered; a code indicative of at least one therapeutic agent administered; a code indicative of at least one diagnostic agent administered; a code indicative of at least one interaction of a administered agent and at least one biological or chemical agent in the subject; a code indicative of at least one dispersion or location of at least one administered agent; a code indicative of at least one detection material administered; a code indicative of the depth of penetration of a administered agent; or a code indicative of the condition of at least one location of an administered frozen particle composition 1110 information regarding at least one cellular or tissue source 1120 information regarding at least one abnormal cellular or tissue source 1130 information regarding at least one type of cell or tissue 1140 at least one frozen particle therapeutic composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 1150 at least one frozen particle therapeutic composition includes at least one major dimension of approximately one centimeter or less, approximately one millimeter or less, approximately one micrometer or less, approximately one nanometer or less, or any value therebetween 1160 one or more reinforcement agents 1170 one or more explosive materials

FIG. 12

1200 receipt by the at least one subject of at least one frozen particle therapeutic composition is pursuant to at least one clinical trial 1210 determining at least one correlation before the administration of the at least one frozen particle therapeutic composition 1220 creating at least one inclusion criterion and at least one exclusion criterion for a clinical trial involving the at least one frozen particle therapeutic composition 1230 suggesting the inclusion of one or more of the at least one subject in at least one clinical trial 1240 suggesting the exclusion of one or more of the at least one subject in at least one clinical trial 1250 using one or more the at least one determination to predict at least one clinical outcome regarding at least one second subject 1260 the at least one second subject has not received the at least one frozen particle therapeutic composition 1270 predicting at least one clinical outcome involving the at least one second subject, wherein the at least one second subject is a plurality of people; and segregating subject identifiers associated with the plurality of people in reference to the predicted at least one clinical outcome 1280 determining the eligibility of the at least one second subject for the at least one clinical trial

FIG. 15

1500 receipt by the at least one subject of at least one frozen particle therapeutic composition is pursuant to at least one clinical trial 1510 determining at least one correlation before the administration of the at least one frozen particle therapeutic composition 1520 creating at least one inclusion criterion and at least one exclusion criterion for a clinical trial involving the at least one frozen particle therapeutic composition 1530 suggesting the inclusion of one or more of the at least one subject in at least one clinical trial 1540 suggesting the exclusion of one or more of the at least one subject in at least one clinical trial 1550 using one or more of the at least one comparison to predict at least one clinical outcome regarding at least one second subject 1560 the at least one second subject has not received the at least one frozen particle therapeutic composition 1570 predicting at least one clinical outcome involving the at least one second subject, wherein the at least one second subject is a plurality of people; and segregating subject identifiers associated with the plurality of people in reference to the predicted at least one clinical outcome 1580 determining the eligibility of the at least one second subject for the at least one clinical trial

FIG. 20

2000 A computer program product comprising:

2010 a signal-bearing medium bearing at least one of 2020 one or more instructions for receiving a first input associated with a first possible dataset, the first possible dataset including data representative of one or more measurements relating to one or more physical attributes of a subject;

2030 one or more instructions for comparing a value associated with the first possible dataset with a second dataset including values representative of parameters relating to one or more expected biological changes following administration of one or more frozen particle therapeutic compositions;

2040 one or more instructions for determining from the comparison at least one biological change following administration of one or more frozen particle therapeutic compositions to the subject; and output information optionally based on the comparison 2050 one or more instructions for accessing the first possible dataset in response to the first input 2060 one or more instructions for generating the first possible dataset in response to the first input 2070 one or more instructions for determining a graphical illustration of the first possible dataset 2080 one or more instructions for determining a graphical illustration of the second possible dataset 2090 computer-readable medium | 2092 recordable medium | 2094 communications medium

FIG. 21

2100 A computer program product comprising:

2110 a signal-bearing medium bearing at least one of 2120 one or more instructions for processing a first input associated with a first possible dataset, the first possible dataset including data representative of one or more measurements relating to one or more physical attributes of a subject;

2130 one or more instructions for comparing a value associated with the first possible dataset with a second dataset including values representative of parameters relating to one or more expected biological changes following administration of one or more frozen particle therapeutic compositions;

2140 one or more instructions for determining from the comparison at least one biological change following administration of one or more frozen particle therapeutic compositions to the subject; and output information optionally based on the comparison

FIG. 23

2300 A method comprising:

2310 comparing information regarding at least one aspect of cellular or tissue abrasion or ablation of at least one biological tissue of at least one subject and information regarding at least one clinical outcome following receipt by the at least one subject of at least one frozen particle composition; and providing output information optionally based on the comparison 2320 determining at least one statistical correlation 2330 counting the occurrence of at least one clinical outcome 2340 information regarding quantity of cells or tissue removed or destroyed 2350 information regarding at least one dimension of cellular, tissue, or other material removal or destruction 2360 information regarding at least one depth, width, or breadth of cellular, tissue, or other material removal or destruction 2370 information regarding two or more subjects with one or more common attributes 2380 genetic attributes, mental attributes, or psychological attributes 2390 genotype attributes or phenotype attributes 2397 at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical condition; medical history, or blood condition

FIG. 24

2410 output information includes at least one of a response signal, a comparison code, a comparison plot, a diagnostic code, a treatment code, a test code, a code indicative of at least one treatment received, a code indicative of at least one prescribed treatment step, a code indicative of at least one vaccination administered; a code indicative of at least one therapeutic agent administered; a code indicative of at least one diagnostic agent administered; a code indicative of at least one interaction of a administered agent and at least one biological or chemical agent in the subject; a code indicative of at least one dispersion or location of at least one administered agent; a code indicative of at least one detection material administered; a code indicative of the depth of penetration of a administered agent; or a code indicative of the condition of at least one location of an administered frozen particle composition 2420 information regarding at least one cellular or tissue source 2430 information regarding at least one abnormal cellular or tissue source 2440 information regarding at least one type of cell or tissue 2450 at least one frozen particle composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 2460 at least one frozen particle composition includes at least one major dimension of approximately one centimeter or less, approximately one millimeter or less, approximately one micrometer or less, approximately one nanometer or less, or any value therebetween 2470 one or more reinforcement agents 2480 one or more explosive materials

FIG. 25

2500 receipt by the at least one subject of at least one frozen particle composition is pursuant to at least one clinical trial 2510 determining at least one correlation before the administration of the at least one frozen particle composition 2515 creating at least one inclusion criterion and at least one exclusion criterion for a clinical trial involving the at least one frozen particle composition 2520 suggesting the inclusion of one or more of the at least one subject in at least one clinical trial 2530 suggesting the exclusion of one or more of the at least one subject in at least one clinical trial 2540 using one or more of the at least one correlation to predict at least one clinical outcome regarding at least one second subject 2550 the at least one second subject has not received the at least one frozen particle composition 2560 predicting at least one clinical outcome involving the at least one second subject, wherein the at least one second subject is a plurality of people; and segregating subject identifiers associated with the plurality of people in reference to the predicted at least one clinical outcome 2570 determining the eligibility of the at least one second subject for the at least one clinical trial

FIG. 27

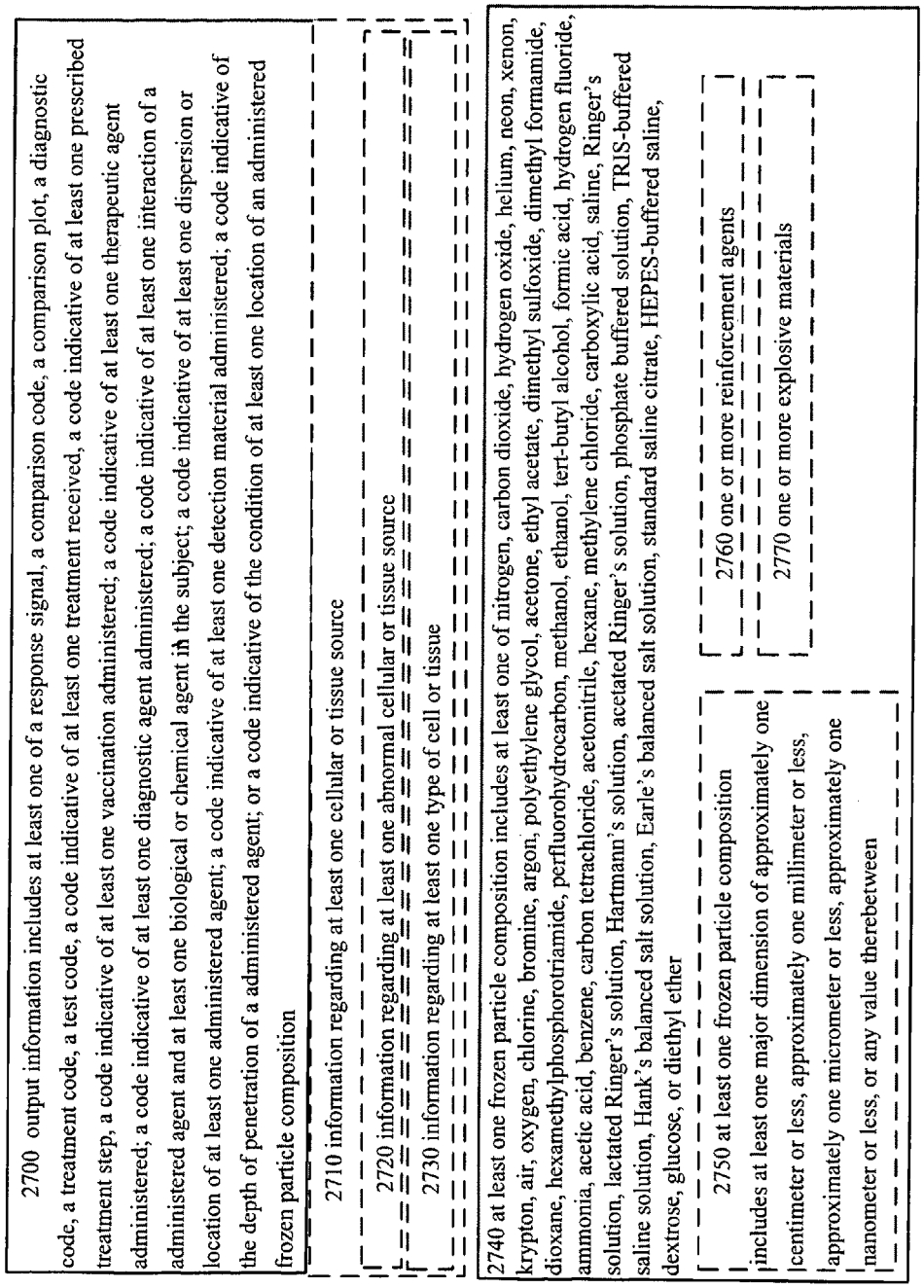

2700 output information includes at least one of a response signal, a comparison code, a comparison plot, a diagnostic code, a treatment code, a test code, a code indicative of at least one treatment received, a code indicative of at least one prescribed treatment step, a code indicative of at least one vaccination administered; a code indicative of at least one therapeutic agent administered; a code indicative of at least one diagnostic agent administered; a code indicative of at least one interaction of a administered agent and at least one biological or chemical agent in the subject; a code indicative of at least one dispersion or location of at least one administered agent; a code indicative of at least one detection material administered; a code indicative of the depth of penetration of a administered agent; or a code indicative of the condition of at least one location of an administered frozen particle composition 2710 information regarding at least one cellular or tissue source 2720 information regarding at least one abnormal cellular or tissue source 2730 information regarding at least one type of cell or tissue 2740 at least one frozen particle composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 2750 at least one frozen particle composition includes at least one major dimension of approximately one centimeter or less, approximately one millimeter or less, approximately one micrometer or less, approximately one nanometer or less, or any value therebetween 2760 one or more reinforcement agents 2770 one or more explosive materials

FIG. 30

3000 one or more instructions that when executed on the at least one computing device cause the at least one computing device to determine a graphical illustration of the second possible dataset 3005 the treatment regimen includes at least one of cellular or tissue removal, cellular or tissue ablation, debridement, delivery of at least one therapeutic agent, cleaning one or more wounds, removing material from at least one biological tissue, or removing material from at least one blood vessel 3008 at least one frozen particle composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 3010 one or more desktop computer, workstation computer, computing system including a cluster of processors, a networked computer, a tablet personal computer, a laptop computer, a mobile device, a mobile telephone, or a personal digital assistant computer 3020 wherein the at least one computing device is configured to communicate with a database to access the first possible dataset 3030 wherein the at least one computing device is configured to communicate with a frozen particle composition selecting apparatus or a frozen particle composition generating apparatus, or both

FIG. 32

3200 wherein the circuitry for receiving a first input associated with a first possible dataset includes circuitry for receiving one or more measurements relating to one or more physical attributes including at least one of height; weight; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; lymph condition, medical history, or blood condition 3210 circuitry for selecting the combination of at least two parameters selected from quality or quantity related to one or more frozen particle compositions, method of administration of one or more frozen particle compositions, administration location of one or more frozen particle compositions, content of one or more frozen particle compositions, timing of administration of one or more frozen particle compositions, decrease in a physical dimension of one or more frozen particle compositions, or time interval between at least two administrations with one or more frozen particle compositions 3220 circuitry for selecting the combination of at least two parameters selected from quality or quantity related to one or more frozen particle compositions, method of administration of one or more frozen particle compositions, administration location of one or more frozen particle compositions, content of one or more frozen particle compositions, timing of administration of one or more frozen particle compositions, decrease in a physical dimension of one or more frozen particle compositions, or time interval between at least two administrations with one or more frozen particle compositions 3230 circuitry for selecting at least one of a clinical outcome; secondary effects related to the treatment; disease stage; longevity; or vaccination administration 3240 wherein the clinical outcome includes a positive clinical outcome or a negative clinical outcome 3250 wherein the clinical outcome includes one or more adverse effect, failure to attain a clinical endpoint of a clinical trial, failing to attain a beneficial effect, or measurement of at least one biochemical, biological or physiological parameter

FIG. 35

3500 receipt by the at least one subject of at least one frozen particle composition is pursuant to at least one clinical trial 3510 one or more instructions for determining at least one comparison before the administration of the at least one frozen particle composition to at least one subject 3520 one or more instructions for creating at least one inclusion criterion and at least one exclusion criterion for a clinical trial involving the at least one frozen particle composition 3530 one or more instructions for suggesting the inclusion of one or more of the at least one subject in at least one clinical trial 3540 one or more instructions for suggesting the exclusion of one or more of the at least one subject in at least one clinical trial 3550 one or more instructions for using one or more of the at least one comparison to predict at least one clinical outcome regarding at least one second subject 3560 the at least one second subject has not received the at least one frozen particle composition 3570 one or more instructions for predicting at least one clinical outcome involving the at least one second subject, wherein the at least one second subject is a plurality of people; and segregating subject identifiers associated with the plurality of people in reference to the predicted at least one clinical outcome 3580 wherein the at least one second subject is a plurality of people; and determining the eligibility of the at least one second subject for the at least one clinical trial

COMPOSITIONS AND METHODS FOR THERAPEUTIC DELIVERY WITH FROZEN PARTICLES

CROSS-REFERENCE TO RELATED APPLICATIONS

The present application is related to U.S. patent application Ser. No. 12/290,683, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,685, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,686, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,690, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,691, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,684, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,670, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,664, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,659, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,658, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,665, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,677, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,687, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008.

The present application is related to U.S. patent application Ser. No. 12/290,676, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008.

All subject matter of the Related Applications and of any and all parent, grandparent, great-grandparent, etc. applications of the Related Applications is incorporated herein by reference to the extent such subject matter is not inconsistent herewith.

SUMMARY

In at least one aspect, a therapeutic composition includes one or more frozen particles including at least one therapeutic agent and at least one of hydrogen oxide, helium, neon, krypton, argon, xenon, nitrogen, chlorine, bromine, oxygen, air, carbon dioxide, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether. In at least one embodiment, at least one of the constituents of the one or more frozen particles is frozen. In at least one embodiment, all of the constituents of the one or more frozen particles are frozen. In at least one embodiment, the at least one composition or therapeutic composition includes one or more frozen solution particles. In at least one embodiment, the composition or therapeutic composition includes one or more frozen solution particles and the composition or therapeutic composition is in at least one crystalline or amorphous phase. In at least one embodiment, the frozen solution particles include at least one of the constituents described herein.

In at least one embodiment, the at least one composition or therapeutic composition includes hydrogen oxide in the form of at least one of amorphous frozen water, low density amorphous ice, high density amorphous ice, crystalline ice, very high density amorphous ice, clathrate ice, or hyperquenched glassy water. In at least one embodiment, the one or more frozen particles include hydrogen oxide in the form of at least one of ice Ic, ice Ih, ice II, ice III, ice IV, ice V, ice VI, ice VII, ice VIII, ice IX, ice X, ice XI, ice XII, ice XIII, or ice XIV. In at least one embodiment, the one or more frozen particles include hydrogen oxide in the form of ice Ic.

In at least one embodiment, the one or more frozen particles have at least one major dimension of approximately one decimeter or less, approximately one centimeter or less, approximately one millimeter or less, approximately one micrometer or less, approximately one nanometer or less, approximately one picometer or less, or any value therebetween. In at least one embodiment, the one or more frozen particles have at least one major dimension of approximately ten micrometers or less. In at least one embodiment, the at least one major dimension of the one or more frozen particles includes at least one of radius, diameter, length, width, height, or perimeter of a particle. In at least one embodiment, the one or more frozen particles have a density greater than approximately 0.92 g/cm$^3$.

In at least on embodiment, the one or more frozen particles approximate the shape of at least one of a sphere, bullet, flechette, cone, needle, arrow, spear, diamond, pyramid, cylinder, minie ball, shuttlecock, spiral, bell, pear, crystal, cube, spheroid, tetrahedron, crescent, or high aspect ratio shape. In at least one embodiment, the one or more frozen particles include a plurality of frozen particles that are approximately uniform with regard to size, shape, weight, or density.

In at least one embodiment, the one or more frozen particles or the compositions exist at about 30° C., about 20° C., about 10° C., about 5° C., about 0° C., about −10° C. about −20° C., about −30° C., about −40° C., about −50° C., about −60° C., about −70° C., about −75° C., about −80° C., about −85° C., about −90° C., about −95° C., about −100° C., about −120° C., about −150° C., about −180° C., about −200° C., about −220° C., about −250° C., or any value less than or therebetween. In certain instances, the one or more frozen particles are utilized at a very cold temperature so that effective penetration of a biological tissue is achieved. In certain instances, the one or more frozen particles are utilized at warmer temperatures, particularly if the contents of the one or more frozen particles include agents that have warmer freezing temperatures. For example, the freezing point of nitrogen is approximately −210° C., whereas the freezing point of dimethyl sulfoxide (DMSO) is approximately 18.45° C. Thus, frozen particles of DMSO can be utilized or administered at a warmer temperature than frozen particles of nitrogen.

In at least one embodiment, the composition or therapeutic composition includes at least one of a polymer, biopolymer, nanoparticle, or detection material. In certain instances, the detection material may be located on or in the one or more frozen particles. In certain instances, the detection material may be intermixed with the one or more frozen particles. In certain instances, the detection material provides a "tracer" agent that allows for viewing one or more locations of administration of the at least one composition or therapeutic composition. Thus, in certain instances the detection material is located on the at least one therapeutic composition or the at least one frozen particle. In other instances, the detection material is separate from the at least one therapeutic composition or the at least one frozen particle and forms a mixture with the therapeutic composition or frozen particles or is administered at approximately the same time, in approximately the same place, or in approximately the same manner as the one or more therapeutic compositions or frozen particles.

In at least one embodiment, the detection material includes at least one electronic identification device. In at least one embodiment, the at least one electronic identification device includes at least one radio frequency identification device. In at least one embodiment, the detection material includes at least one radioactive element. In at least one embodiment, the radioactive element includes one or more of $^{32}P$, $^{35}S$, $^{13}C$, $^{131}I$, $^{191}Ir$, $^{192}Ir$, $^{193}Ir$, $^{201}Tl$, or $^3H$.

In at least one embodiment, the detection material includes at least one colorimetric substance. In at least one embodiment, the at least one colorimetric substance includes one or more of an inorganic, organic, biological, natural, artificial, or synthetic substance. In at least one embodiment, the at least one colorimetric substance includes one or more of a dye, pigment, or a light-emitting substance. In at least one embodiment, the light-emitting substance includes at least one of a luminescent substance, fluorescent substance, phosphorescent substance, or quantum dot. In at least one embodiment, the at least one colorimetric substance is biocompatible.

In at least one embodiment, the detection material includes at least one of a diamagnetic particle, ferromagnetic particle, paramagnetic particle, super paramagnetic contrast agent, or other magnetic particle.

In at least one embodiment, the composition or therapeutic composition includes one or more abrasives, one or more reinforcement agents, or one or more explosive materials. In at least one embodiment, the one or more explosive materials include at least one of a high explosive or a low explosive. In at least one embodiment, the one or more explosive materials include at least one of carbon dioxide, nitroglycerine, or a reactive metal.

In at least one embodiment, the one or more reinforcement agents include at least one of a natural, artificial, or synthetic agent. In at least one embodiment, the one or more reinforcement agents include at least one of a plate, fiber, or spheroid. In at least one embodiment, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, hydrogen oxide ice, plant matter (including vegetable matter), animal matter, or mineral matter. In at least one embodiment, the one or more reinforcement agents are located at least on the surface or beneath the surface of the particle. In at least one embodiment, the one or more reinforcement agents are located within the particle.

In at least one embodiment, the at least one therapeutic agent includes at least one of an organic or inorganic small molecule, clathrate or caged compound, protocell, coacervate, microsphere, proteinoid, laminate, helical rod, liposome, macroscopic tube, noisome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, sphingolipid, glycosphingolipid, glycoprotein, peptidoglycan, lipid, carbohydrate, metalloprotein, proteoglycan, chromosome, nucleus, acid, base, buffer, protic solvent, aprotic solvent, nitric oxide, nitric oxide synthase, amino acid, micelle, polymer, co-polymer, or piloxymer.

In at least one embodiment, the at least one therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

In at least one embodiment, the antimicrobial agent includes at least one of an anti-fungal agent, antibiotic agent, anti-parasitic agent, or anti-worm agent. In at least one embodiment, the at least one anti-tumor agent includes one or more of an alkylating agent, antimetabolite, anthracycline, plant alkaloid, topoisomerase inhibitor, monoclonal antibody, or tyrosine kinase inhibitor. In at least one embodiment, the at least one plant alkaloid includes paclitaxel.

In at least one embodiment, the at least one therapeutic agent includes one or more of a prodrug or precursor compound. In at least one embodiment, the at least one therapeutic agent is activated by delivery of the therapeutic composition to at least one biological tissue.

In at least one embodiment, the at least one therapeutic agent resides in one or more distinct regions of the one or more frozen particles. In at least one embodiment, the one or more frozen particles include a plurality of frozen particles that are approximately uniform in size, shape, weight, or density.

In at least one embodiment, a therapeutic composition includes at least one of a solid, liquid, or gas. In at least one embodiment, the therapeutic composition includes one or more of a suspension, mixture, solution, sol, clathrate, colloid, emulsion, microemulsion, aerosol, ointment, capsule, powder, tablet, suppository, cream, device, paste, liniment, lotion, ampule, elixir, spray, suspension, syrup, tincture, detection material, polymer, biopolymer, buffer, adjuvant, diluent, lubricant, disintegration agent, suspending agent, solvent, colorimetric agent, light-emitting substance, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, or gel.

In at least one embodiment, the composition is formulated to be a therapeutic composition administered by one or more of topical delivery, oral delivery, enteral delivery, mucosal delivery, percutaneous delivery, or parenteral delivery. In at least one embodiment, parenteral delivery includes at least one of intravenous delivery, intra-arterial delivery, intracardiac delivery, subcutaneous delivery, intraperitoneal delivery, or intramuscular delivery. In at least one embodiment, the composition or therapeutic composition is formulated to be administered by high velocity impact. In at least one embodiment, the composition or therapeutic composition is formulated to be administered by one or more devices. In certain instances, an example of a device that may be used for administering one or more of the compositions described herein includes a handheld device, such as a wand, a pen, a baton, a hose, a sprayer, a gun (e.g., a pellet gun), or other handheld device. In certain instances, the device is at least part of a built-in delivery device, such as may be included in a wall, an overhead device, a corral, a gate, or a device that includes a cavity into which a subject may be placed for administration or delivery of at least one composition described herein. In certain instances, the device has robotic action. In any of these instances, the device may be remotely controlled, for example, by a human or computer program.

In at least one aspect, a method of providing at least one therapeutic agent to at least one biological tissue of a subject includes delivering at least one therapeutic composition as described herein. In at least one embodiment, delivering at least one therapeutic composition to at least one biological tissue includes propelling the therapeutic composition toward the at least one biological tissue. In certain instances, the therapeutic composition is propelled to or at a predetermined pressure for delivery of the at least one therapeutic composition to a desired location on or in the at least one biological tissue. In at least one embodiment, the therapeutic composition is propelled using a pressure set at least about 10 psi, about 20 psi, about 30 psi, about 40 psi, about 50 psi, at least about 100 psi, at least about 200 psi, at least about 300 psi, at least about 400 psi, at least about 450 psi, at least about 500 psi, at least about 600 psi, at least about 700 psi, at least about 800 psi, at least about 900 psi, at least about 1000 psi, at least about 1100 psi, at least about 1200 psi, at least about 1300 psi, at least about 1400 psi, at least about 1500 psi, about 2000 psi, about 2500 psi, a bout 3000 psi, a bout 3500 psi, about 4000 psi, about 5000 psi, about 6000 psi, about 7000 psi, about 8000 psi, about 9000 psi, about 10000 psi, or any value therebetween.

In at least one embodiment, the at least one therapeutic composition is propelled at or to a predetermined velocity for delivery of the at least one therapeutic composition to a desired location of the at least one biological tissue. In at least one embodiment, the at least one therapeutic composition is propelled at or to a velocity of approximately 10 m/s, approximately 20 m/s, approximately 30 m/s, approximately 40 m/s, approximately 50 m/s, approximately 60 m/s, approximately 70 m/s, approximately 80 m/s, approximately 90 m/s, approximately 100 m/s, approximately 200 m/s, approximately 300 m/s, approximately 400 m/s, approximately 500 m/s, approximately 600 m/s, approximately 700 m/s, approximately 800 m/s, approximately 900 m/s, approximately 1000 m/s, approximately 1500 m/s, approximately 2000 m/s, or any value greater or therebetween.

In at least one embodiment, delivering at least one therapeutic agent to at least one biological tissue of a subject includes ejecting the therapeutic composition toward at least one biological tissue. In at least one embodiment, delivering at least one therapeutic composition includes accelerating the therapeutic composition toward at least one biological tissue. In at least one embodiment, the at least one therapeutic composition is accelerated to a predetermined velocity for delivery of the at least one therapeutic composition to a desired location of the at least one biological tissue. In at least one embodiment, the at least one therapeutic composition is accelerated toward the at least one biological tissue to a velocity of approximately 10 m/s, approximately 20 m/s, approximately 30 m/s, approximately 40 m/s, approximately 50 m/s, approximately 60 m/s, approximately 70 m/s, approximately 80 m/s, approximately 90 m/s, approximately 100 m/s, approximately 200 m/s, approximately 300 m/s, approximately 400 m/s, approximately 500 m/s, approximately 600 m/s, approximately 700 m/s, approximately 800 m/s, approximately 900 m/s, approximately 1000 m/s, approximately 1500 m/s, approximately 2000 m/s, or any value greater or therebetween.

In at least one embodiment, a method of providing at least one therapeutic agent to at least one biological tissue includes propelling, ejecting, or accelerating multiple therapeutic compositions toward at least one biological tissue. In at least one embodiment, a method of providing at least one therapeutic agent to at least one biological tissue includes delivering at least one therapeutic agent to at least one biological tissue by propelling, ejecting, or accelerating two or more of the multiple therapeutic compositions. In at least one embodiment, the multiple therapeutic compositions include one or more similar therapeutic agents. In at least one embodiment, the multiple therapeutic compositions include one or more dissimilar therapeutic agents.

A particular plurality of compositions or therapeutic compositions may include multiple frozen particles where various multiple agents are associated with a single particle. Likewise, a particular plurality of compositions or therapeutic compositions may include various multiple agents, where each individual agent is associated with a single frozen particle. In at least one embodiment, a plurality of compositions or therapeutic compositions may include any number of subsets of frozen particles associated with a particular therapeutic agent or other constituent. During the course of any particular method described herein, one or more plurality of compositions or therapeutic compositions, or any particular subset thereof, may be administered in a single treatment.

One non-limiting example of multiple therapeutic agents capable of combining to form another therapeutic agent includes combining at least one prodrug and at least one enzyme with a single frozen particle, wherein the at least one prodrug and at least one enzyme combine during administration to form at least one active therapeutic agent. In another non-limiting example, a single frozen particle includes at least one adjuvant and at least one immunogen.

In at least one embodiment, delivering or administering the at least one composition or therapeutic composition includes contacting the at least one surface of at least one biological tissue of a subject with at least one composition or therapeutic composition. In at least one embodiment, delivering or administering the at least one composition or therapeutic composition includes contacting the at least one surface of at least one biological tissue of a subject with one or more frozen particles. In at least one embodiment, delivering or administering the at least one composition or therapeutic composition includes rupturing one or more cells of at least one surface of at least one biological tissue of a subject. In at least one embodiment, delivering the at least one therapeutic composition occurs prior to, during, or subsequent to surgery on the at least one biological tissue or on the subject.

In at least one embodiment, a method for providing at least one therapeutic agent to at least one biological tissue includes at least one biological tissue located in at least one of in situ, in vitro, in vivo, in utero, in planta, in silico, or ex vivo. In certain instances, the at least one biological tissue includes at least one tissue or organ that was artificially synthesized from biological or other sources. In at least one embodiment, the at least one biological tissue is located in vivo. In at least one embodiment, the at least one biological tissue is located in at least one tissue or organ related to transplantation. In at least one embodiment, the at least one tissue or organ related to transplantation includes at least one donor or recipient tissue or organ. In at least one embodiment, the at least one donor includes at least one cadaver. In at least one embodiment, the at least one biological tissue is ingested by at least one subject. In at least one embodiment, the at least one biological tissue includes one or more of skin, scalp, hair, nail, nail bed, teeth, eye, ear, ovary, oviduct, tongue, tonsil, adenoid, liver, bone, pancreas, stomach, blood vessel, blood, lymph, heart, lung, brain, breast, kidney, bladder, urethra, ureter, gall bladder, uterus, prostate, testes, fallopian tubes, vas deferens, large intestine, small intestine, esophagus, oral cavity, nasal cavity, otic cavity, connective tissue, muscle tissue, or adipose tissue. In at least one embodiment, methods and compositions described herein relate to providing or removing reproductive sterilization of a subject.

In at least one embodiment, a method for abrasion of at least one biological tissue surface of a subject and the at least one biological tissue includes at least one cell mass. In at least one embodiment, the at least one cell mass includes at least one of a scar, pore, pit, eschar, granuloma, keloid, artheromatous plaque, abscess, pustule, scaling (e.g., psoriasis or eczema), infected tissue, hair follicle, necrotic tissue, stratum corneum, wrinkle, wound, tumor, skin structure, nevus, cyst, lesion, callus, neoplastic tissue, gangrenous tissue, or cellular deposit.

In at least one embodiment, the at least one cell mass includes at least one benign or malignant tumor. In at least one embodiment, the at least one benign or malignant tumor relates to one or more of a melanoma, lymphoma, leukemia, sarcoma, blastoma, or carcinoma. In at least one embodiment, the at least one cell mass is related to at least one blood clot, microorganism accumulation, blood vessel obstruction, duct obstruction, bowel obstruction, infection, gangrene, connective tissue destruction, tissue or organ damage, injury, white blood cell accumulation, or cancer.

In at least one embodiment, a method includes delivering at least one therapeutic agent to at least one biological tissue and includes delivering to the at least one biological tissue at least one of a polymer, biopolymer, nanoparticle, or detection material, examples of each of which are described herein. In at least one embodiment, the detection material is intermixed with the at least one therapeutic composition. In at least one embodiment, the detection material resides in the at least one therapeutic composition. In at least one embodiment, the detection material resides in the one or more frozen particles.

In at least one embodiment, a method includes delivering at least one therapeutic agent to at least one biological tissue and the at least one biological tissue is located at least one subject that includes at least one invertebrate or vertebrate animal. In at least one embodiment, the at least one subject includes insects, insect cells, bacteria, algae, plankton, or protozoa. In at least one embodiment, the subject includes at least one insect, arachnid, microorganism, reptile, mammal, amphibian, bird or fish. In at least one embodiment, the subject includes at least one human. In at least one embodiment, the subject includes at least one livestock, pet, undomesticated herd animal, wild animal or product animal. In at least one embodiment, the subject includes at least one of a sheep, goat, frog, dog, cat, rat, mouse, vermin, monkey, duck, horse, cow, pig, chicken, shellfish, fish, turkey, llama, alpaca, bison, wolf, fox, coyote, deer, rabbit, guinea pig, yak, chinchilla, mink, reindeer, deer, elk, raccoon, camel, donkey, or mule.

In at least one aspect, a method of vaccinating a subject includes delivering or administering to a subject at least one therapeutic composition that includes at least one vaccine and one or more frozen particles, examples of which are described herein.

In at least one embodiment, the at least one therapeutic composition includes at least one pharmaceutically-acceptable carrier or excipient. In at least one embodiment, the at least one vaccine includes at least one prophylactic or therapeutic vaccine. In at least one embodiment, the therapeutic vaccine includes an anti-cancer vaccine. In at least one embodiment, the at least one therapeutic composition includes at least one of an anti-tumor agent, antimicrobial agent, anti-viral agent, immunogen, antigen, live microbe, dead microbe, attenuated microbe, microbe or component thereof, live virus, recombinant virus, killed virus, attenuated virus, virus component, plasmid DNA, nucleic acid, amino acid, peptide, protein, glycopeptide, proteoglycan, glycoprotein, glycolipid, sphingolipid, glycosphingolipid, cancer cell or component thereof, organic or inorganic small molecule, or toxoid.

In at least one embodiment, the therapeutic composition includes at least one adjuvant. In certain instances, the at least one adjuvant includes one or more organic or inorganic compounds. In certain instances, the at least one adjuvant includes at least one of a liposome, viro some, lipid, phospholipid, mineral salt, single-stranded DNA, double-stranded RNA, lipopolysaccharide, molecular antigen cage, CpG motif, microbial cell wall or component thereof, squalene, oil emulsion, surfactant, saponin, isolated microbial toxin, modified microbial toxin, endogenous immunomodulator, or cytokine.

In at least one embodiment, the method of vaccinating a subject includes delivering the at least one therapeutic composition to at least one biological tissue of the subject, examples of which are described herein. For example, as described herein for any composition or therapeutic composition, a vaccine composition may be propelled, accelerated, or ejected toward the at least one biological tissue. In certain instances, delivering the at least one vaccine composition includes contacting the at least one biological tissue with the at least one composition, therapeutic agent, or vaccine.

In at least one embodiment, a method of vaccinating a subject includes delivering the at least one vaccine composition prior to, during, or subsequent to surgery. In at least one embodiment, the at least one biological tissue is located in at least one of in situ, in vitro, in vivo, in utero, in planta, in silico, or ex vivo. In at least one embodiment, the at least one biological tissue is located in vivo. In at least one embodiment, the at least one biological tissue is transplanted or implanted into at least one subject. In at least one embodiment, the biological tissue includes artificial or synthetic tissue or organs. In at least one embodiment, the at least one biological tissue is ingested by at least one subject. In at least one embodiment, the at least one biological tissue includes at least one biological tissue from at least one donor or recipient. In at least one embodiment, at least one donor includes at least one cadaver.

In at least one embodiment, the at least one biological tissue includes one or more of skin, scalp, hair, nail, nail bed, teeth, eye, ear, ovary, oviduct, tongue, tonsil, adenoid, liver, bone, pancreas, stomach, blood vessel, blood, lymph, heart, lung, brain, breast, kidney, bladder, urethra, ureter, gall bladder, uterus, prostate, large intestine, small intestine, esophagus, oral cavity, nasal cavity, otic cavity, connective tissue, muscle tissue, or adipose tissue.

In at least one embodiment, a method of vaccinating a subject includes delivering at least one vaccine composition to at least one biological tissue that includes at least one cell mass. In at least one embodiment, the at least one cell mass includes at least one of a scar, pore, pit, eschar, granuloma, keloid, artheromatous plaque, abscess, pustule, hair follicle, necrotic tissue, stratum corneum, wrinkle, wound, tumor, skin structure, nevus, cyst, lesion, callus, neoplastic tissue, gangrenous tissue, or cellular deposit. In at least one embodiment, the at least one cell mass includes at least one benign or malignant tumor. In at least one embodiment, the at least one benign or malignant tumor relates to one or more of a melanoma, lymphoma, leukemia, sarcoma, blastoma, or carcinoma. In at least one embodiment, the at least one cell mass is related to at least one blood clot, microorganism accumulation, blood vessel obstruction, duct obstruction, bowel obstruction, infection, gangrene, connective tissue destruction, tissue or organ damage, injury, white blood cell accumulation, or cancer.

In at least one embodiment, a method of vaccinating a subject includes delivering to the at least one biological tissue at least one of a polymer, biopolymer, nanoparticle, or detection material, examples of each of which are described herein.

In at least one embodiment, a method of vaccinating a subject includes administering at least one vaccine composition to at least one subject, including at least one invertebrate or vertebrate animal. In at least one embodiment, the subject includes insects, insect cells, bacteria, algae, plankton, or protozoa. In at least one embodiment, the subject includes at least one insect, arachnid, microorganism, reptile, mammal, amphibian, bird or fish. In at least one embodiment, the subject includes at least one human. In at least one embodiment, the subject includes at least one livestock, pet, undomesticated herd animal, wild animal or product animal. In at least one embodiment, the subject includes at least one of a sheep, goat, frog, dog, cat, rat, mouse, vermin, monkey, duck, horse, cow, pig, chicken, shellfish, fish, turkey, llama, alpaca, bison, wolf, fox, coyote, deer, rabbit, guinea pig, yak, chinchilla, mink, reindeer, deer, elk, raccoon, camel, donkey, or mule.

In at least one aspect, a method includes comparing information regarding at least one aspect of administering at least one frozen particle therapeutic composition to at least one subject and information regarding at least one clinical outcome following receipt by the at least one subject of at least one frozen particle therapeutic composition; and providing output information that is optionally based on the comparison.

In at least one embodiment, the method further comprises determining at least one statistical correlation. In at least one embodiment, the method further comprises counting the occurrence of at least one clinical outcome or determining at least one correlation before the administration of the at least one frozen particle therapeutic composition. In at least one embodiment, the information regarding the at least one aspect of administering at least one frozen particle therapeutic composition and the regarding at least one clinical outcome before the administration of the at least one frozen particle therapeutic composition to another subject. In at least one embodiment, the information regarding the at least one aspect of administering at least one frozen particle therapeutic composition includes information regarding the amount of at least one frozen particle therapeutic composition or therapeutic agent delivered or administered to at least one biological tissue of a subject.

In at least one embodiment, the information regarding the at least one aspect of administering at least one frozen particle therapeutic composition includes information regarding at least one dimension of biological tissue penetration. In at least one embodiment, the information regarding the at least one dimension of biological tissue penetration includes information regarding at least one of depth, width, or breadth of delivery or administration of at least one frozen particle therapeutic composition to at least one biological tissue of at least one subject.

In at least one embodiment, the information regarding at least one aspect of administering at least one frozen particle therapeutic composition includes information regarding two or more subjects with one or more common attributes. In at least one embodiment, the one or more common attributes include genetic attributes, mental attributes, or psychological attributes. In at least one embodiment, the one or more common attributes include genotype attributes or phenotype attributes.

In at least one embodiment, the one or more common attributes include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical history; or blood condition.

In the at least one embodiment, the output information includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of an administered frozen particle composition.

In at least one embodiment, the information regarding at least one aspect of administering at least one frozen particle therapeutic composition includes information regarding at least one cellular or tissue source. In at least one embodiment, the information regarding at least one cellular or tissue source includes information regarding at least one abnormal cellular or tissue source. In at least one embodiment, the information regarding at least one cellular or tissue source includes information regarding at least one type of cell or tissue.

In at least one embodiment, the at least one frozen particle therapeutic composition includes at least one of nitrogen, carbon dioxide, hydrogen oxide, helium, neon, xenon, krypton, air, oxygen, chlorine, oxygen, air, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In at least one embodiment, the at least one frozen particle composition includes at least one major dimension of approximately one centimeter or less, approximately one millimeter or less, approximately one micrometer or less, approximately one nanometer or less, or any value therebetween. In at least one embodiment, the at least one frozen particle therapeutic composition includes one or more reinforcement agents, one or more abrasives, or one or more explosive materials.

In at least one embodiment, the receipt by the at least one subject of at least one frozen particle therapeutic composition is pursuant to at least one clinical trial. In at least one embodiment, the method includes creating at least one inclusion criterion and at least one exclusion criterion for a clinical trial involving the at least one frozen particle therapeutic composition.

In at least one embodiment, the method further comprises suggesting the inclusion of one or more of the at least one subject in at least one clinical trial. In at least one embodiment, the method further comprises suggesting the exclusion of one or more of the at least one subject in at least one clinical trial. In at least one embodiment, the method includes using one or more of the at least one comparisons to predict at least one clinical outcome regarding at least one second subject. In at least one embodiment, the at least one second subject has not received the at least one frozen particle therapeutic composition. In at least one embodiment, using one or more of the at least one correlation further comprises predicting at least one clinical outcome involving the at least one second subject, wherein the at least one second subject is a plurality of people; and segregating subject identifiers associated with the plurality of people in reference to the predicted at least one clinical outcome. In at least one embodiment, the method includes determining the eligibility of the at least one second subject for the at least one clinical trial.

In at least one aspect, a method of predicting a clinical outcome of administering at least one frozen particle therapeutic composition to at least one biological tissue of at least one first subject includes determining a similarity or dissimilarity in information regarding at least one aspect of administering at least one therapeutic composition to the at least one biological tissue of the at least one first subject to information regarding at least one aspect of administering at least one therapeutic composition to the at least one biological tissue of the at least one second subject, wherein the at least one second subject attained a clinical outcome following receipt of the at least one frozen particle therapeutic composition; and providing output information, optionally based on the comparison or determination.

In at least one embodiment, the information regarding at least one aspect of administering at least one therapeutic composition includes information regarding amount of at least one therapeutic composition or therapeutic agent administered to at least one biological tissue of at least one subject.

In at least one embodiment, the information regarding at least one aspect of administering at least one frozen particle therapeutic composition includes information regarding at least one dimension of biological tissue penetration. Such information may include, but not be limited to information regarding at least one of depth, width, or breadth of administration of at least one frozen particle therapeutic composition to at least one biological tissue of at least one subject. In at least one embodiment, the information regarding at least one aspect of administering at least one therapeutic composition includes information regarding two or more subjects with one or more common attributes, including but not limited to genetic attributes, mental attributes, or psychological attributes. In at least one embodiment, the one or more common attributes include genotype attributes or phenotype attributes. In at least one embodiment, the one or more common attributes include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood condition; lymph condition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical history; or blood condition.

In at least one embodiment, the output information includes at least one of a response signal, a comparison code, a comparison plot, a diagnostic code, a treatment code, a test code, a code indicative of at least one treatment received, a code indicative of at least one prescribed treatment step, a code indicative of at least one vaccination administered; a code indicative of at least one therapeutic agent administered; a code indicative of at least one diagnostic agent administered; a code indicative of at least one interaction of a administered agent and at least one biological or chemical agent in the subject; a code indicative of at least one dispersion or location of at least one administered agent; a code indicative of at least one detection material administered; a code indicative of the depth of penetration of an administered agent; or a code indicative of the condition of at least one location of an administered frozen particle composition.

In at least one embodiment, the information regarding at least one aspect of administering at least one frozen particle therapeutic composition includes information regarding at least one cellular or tissue source. In at least one embodiment, the information regarding at least one cellular or tissue source includes information regarding at least one abnormal cellular or tissue source, and may include at least one type of cell or tissue. In at least one embodiment of the method, the at least one frozen particle therapeutic composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

In at least one embodiment of the method, the at least one frozen particle therapeutic composition includes at least one major dimension of approximately one centimeter or less, approximately one millimeter or less, approximately one micrometer or less, approximately one nanometer or less, or any value therebetween. In at least one embodiment, the at least one frozen particle therapeutic composition includes one or more reinforcement agents, one or more abrasives, or one or more explosive agents.

In at least one embodiment, the method includes that the receipt by the at least one subject of at least one frozen particle therapeutic composition is pursuant to at least one clinical trial. In at least one embodiment, the method further comprises determining at least one correlation before the onset of the at least one frozen particle therapeutic composition. In at least one embodiment, the method further comprises creating at least one inclusion criterion and at least one exclusion criterion for a clinical trial involving the at least one frozen particle therapeutic composition. In at least one embodiment, the method further comprises suggesting the inclusion of one or more of the at least one subject in at least one clinical trial. In at least one embodiment, the method further comprises suggesting the exclusion of one or more of the at least one subject in at least one clinical trial. In at least one embodiment, the method further comprises using one or more determination to predict at least one clinical outcome regarding at least one second subject. In at least one embodiment, the at least one second subject has not received the at least one frozen particle therapeutic composition. In at least one embodiment, using one or more of the at least one comparison includes predicting at least one clinical outcome involving the at least one second subject, wherein the at least one second subject is a plurality of people; and segregating subject identifiers associated with the plurality of people in reference to the predicted at least one clinical outcome. In at least one embodiment, the method includes determining the eligibility of the at least one second subject for the at least one clinical trial.

In at least one aspect, a system comprises at least one computer program, configured with a computer-readable medium, for use with at least one computer system and wherein the computer program includes a plurality of instructions including but not limited to one or more instructions for comparing information regarding at least one aspect of at least one therapeutic administration of at least one frozen particle therapeutic composition to at least one biological tissue of at least one subject, and information regarding at least one clinical outcome following receipt by the at least one subject of at least one frozen particle therapeutic composition.

In at least one embodiment, the information regarding at least one aspect of therapeutic administration of at least one frozen particle therapeutic composition includes information regarding amount of the at least one therapeutic composition or therapeutic agent administered to at least one biological tissue of at least one subject. In at least one embodiment, the information regarding at least one aspect of therapeutic administration of at least one frozen particle therapeutic composition includes information regarding at least one dimension of biological tissue penetration. In at least one embodiment, the information regarding at least one dimension of biological tissue penetration includes information regarding at least one of depth, width, or breadth of administration of at least one frozen particle therapeutic composition to at least one biological tissue of at least one subject.

In at least one embodiment, the computing device is configured to communicate with at least one printing device, at least one imaging device, or at least one input device. In at least one embodiment, the information regarding at least one aspect of therapeutic administration of at least one frozen particle therapeutic composition includes information regarding two or more subjects with one or more common attributes. In at least one embodiment, the information regarding at least one aspect of therapeutic administration of at least one frozen particle therapeutic composition includes information regarding at least one cellular or tissue source. In at least one embodiment, the information regarding at least one cellular or tissue source includes information regarding at least one abnormal cellular or tissue source. In at least one embodiment, information regarding the at least one cellular or tissue source includes information regarding at least one type of cell or tissue.

In at least one embodiment, the system includes information relating to at least one frozen particle therapeutic composition including at least one of nitrogen, carbon dioxide, hydrogen oxide, helium, neon, xenon, krypton, air, oxygen, chlorine, oxygen, air, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether. In at least one embodiment, the at least one frozen particle therapeutic composition includes at least one major dimension of approximately one centimeter or less, approximately one millimeter or less, approximately one micrometer or less, approximately one nanometer or less, or any value therebetween. In at least one embodiment, the at least one frozen particle therapeutic composition includes one or more reinforcement agents, one or more abrasives, or one or more explosive materials.

In at least one embodiment, the system includes that the receipt by the at least one subject of at least one frozen particle therapeutic composition is pursuant to at least one clinical trial. In at least one embodiment, the system further comprises determining at least one correlation before the administration of the at least one frozen particle therapeutic composition. In at least one embodiment, the system further comprises creating at least one inclusion criterion and at least one exclusion criterion for a clinical trial involving the at least one frozen particle therapeutic composition. In at least one embodiment, the system further comprises suggesting the inclusion of one or more of the at least one subject in at least one clinical trial. In at least one embodiment, the system further comprises suggesting the exclusion of one or more of the at least one subject in at least one clinical trial. In at least one embodiment, the system further comprises using one or more of the at least one comparison to predict at least one clinical outcome regarding at least one second subject. In at least one embodiment, the at least one second subject has not received the at least one frozen particle therapeutic composition.

In at least one embodiment, using one or more of the at least one comparison includes predicting at least one clinical outcome involving the at least one second subject, wherein the at least one second subject is a plurality of people; and segregating subject identifiers associated with the plurality of people in reference to the predicted at least one clinical outcome. In at least one embodiment, using one or more of the at least one comparison includes the at least one second subject is a plurality of people; and determining the eligibility of the at least one second subject for the at least one clinical trial.

In at least one aspect, a system comprises at least one computer program, configured with a computer-readable medium, for use with at least one computer system and wherein the computer program includes a plurality of instructions including but not limited to one or more instructions for comparing information regarding at least one aspect of at least one therapeutic administration of at least one frozen particle therapeutic composition to at least one biological tissue of at least one subject, and information regarding at least one frozen particle therapeutic composition involving the at least one biological tissue of the at least one subject; and one or more instructions for applying one or more comparisons to the information regarding the at least one aspect of therapeutic administration of at least one frozen particle therapeutic composition to a plurality of people.

In at least one embodiment, the system includes one or more instructions for segregating subject identifiers associated with the plurality of people in reference to at least one of the one or more applied comparisons. In at least one embodiment, the information regarding at least one aspect of the therapeutic administration of at least one frozen particle therapeutic composition includes information regarding the amount of therapeutic composition or therapeutic agent administered to at least one biological tissue of at least one subject. In at least one embodiment, the information regarding at least one aspect of the therapeutic administration of at least one frozen particle therapeutic composition includes information regarding at least one dimension of biological tissue penetration. In at least one embodiment, the information regarding at least one dimension of biological tissue penetration includes information relating to at least one of depth, width, or breadth of administration of the at least one frozen particle therapeutic composition to at least one biological tissue of at least one subject. In at least one embodiment, the system includes one or more instructions for segregating individual identifiers associated with the plurality of people in reference to at least one characteristic shared by two or more subjects in the plurality of people.

In at least one aspect, a computer program product includes a signal bearing medium bearing at least one of one or more instructions for receiving a first input associated with a first possible dataset, the first possible dataset including data representative of one or more measurements relating to one or more physical attributes of a first subject; one or more instructions for comparing a value associated with the first possible dataset with a second dataset including values representative of predictive regimen parameters from a second subject with one or more similar or dissimilar physical attributes; one or more instructions for determining from the comparison at least one frozen particle therapeutic composition regimen for the first subject; and output information. In at least one embodiment, the output information is based on the comparison.

In at least one embodiment, the computer program product includes one or more instructions for accessing the first possible dataset in response to the first input. In at least one embodiment, the computer program product further comprises one or more instructions for generating the first possible dataset in response to the first input. In at least one embodiment, the computer program product further comprises one or more instructions for determining a graphical illustration of the first possible dataset. In at least one embodiment, the computer program product further comprises one or more instructions for determining a graphical illustration of the second possible dataset. In at least one embodiment, the computer program product includes a signal bearing medium, such as a computer-readable medium. In at least one embodiment, the signal bearing medium includes a recordable medium, or a communications medium.

In at least one aspect, a computer program product includes a signal bearing medium bearing at least one of one or more instructions for processing a first possible dataset, the first possible dataset including data representative of one or more measurements relating to one or more physical attributes of a first subject; one or more instructions for comparing a value associated with the first possible dataset with a second dataset including values representative of predictive regimen parameters from a second subject with one or more similar or dissimilar physical attributes; one or more instructions for determining from the comparison at least one frozen particle therapeutic composition treatment regimen for the first subject; and output information, wherein the output information is optionally based on the comparison.

In at least one aspect, a computer program product includes a signal bearing medium bearing at least one of one or more instructions responsive to a first possible dataset, the first possible dataset including data representative of one or more measurements relating to one or more physical attributes of a first subject; one or more instructions for comparing a value associated with the first possible dataset with a second dataset including values representative of predictive regimen parameters for a second subject with one or more similar or dissimilar physical attributes; one or more instructions for determining from the comparison at least one frozen particle therapeutic composition treatment regimen for the first subject; and output information.

In at least one aspect, a computer program product includes a signal bearing medium bearing at least one of one or more instructions for receiving a first input associated with a first possible dataset, the first possible dataset including data representative of one or more measurements relating to one or more physical attributes of a subject; one or more instructions for comparing a value associated with the first possible dataset with a second dataset including values representative of parameters relating to one or more expected biological changes following administration of one or more frozen particle therapeutic compositions; one or more instructions for determining from the comparison at least one biological change following administration of one or more frozen particle therapeutic compositions to the subject; and output information. In at least one embodiment, the output information is based on the comparison.

In at least one embodiment, the computer program product includes one or more instructions for accessing the first possible dataset in response to the first input. In at least one embodiment, the computer program product further comprises one or more instructions for generating the first possible dataset in response to the first input. In at least one embodiment, the computer program product further comprises one or more instructions for determining a graphical illustration of the first possible dataset. In at least one embodiment, the computer program product further comprises one or more instructions for determining a graphical illustration of the second possible dataset. In at least one embodiment, the computer program product includes a signal bearing medium that includes a computer-readable medium, a recordable medium, or a communications medium.

In at least one aspect, a computer program product includes a signal bearing medium bearing at least one of one or more instructions for processing a first input associated with a first possible dataset, the first possible dataset including data representative of one or more measurements relating to one or more physical attributes of a subject; one or more instructions for comparing a value associated with the first possible dataset with a second dataset including values representative of parameters relating to one or more expected biological changes following administration of one or more frozen particle therapeutic compositions; one or more instructions for determining from the comparison at least one biological change following administration of one or more frozen particle therapeutic compositions to the subject; and output information.

In at least one aspect, a computer program product includes a signal bearing medium bearing at least one of one or more instructions responsive to a first possible dataset, the first possible dataset including data representative of one or more measurements relating to one or more physical attributes of a subject; one or more instructions for comparing a value associated with the first possible dataset with a second dataset including values representative of parameters relating to one or more expected biological changes following administration of one or more frozen particle therapeutic compositions; one or more instructions for determining from the comparison at least one biological change following administration of one or more frozen particle therapeutic compositions to the subject; and output information.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 7 illustrates a partial view of a method 700 that includes generating at least one response.

FIG. 8 illustrates a partial view and an embodiment of FIG. 7.

FIG. 9 illustrates a partial view and an embodiment of FIG. 7.

FIG. 11 illustrates a partial view and an embodiment of FIG. 10.

FIG. 12 illustrates a partial view and an embodiment of FIG. 10.

FIG. 15 illustrates a partial view and an embodiment of FIG. 13.

FIG. 20 illustrates a partial view of a computer program product 2000 for executing a computing process on a computing device.

FIG. 21 illustrates a partial view of a computer program product 2100 for executing a computing process on a computing device.

FIG. 23 illustrates a partial view of a method 2300 that includes generating at least one response.

FIG. 24 illustrates a partial view and an embodiment of FIG. 23.

FIG. 25 illustrates a partial view and an embodiment of FIG. 23.

FIG. 27 illustrates a partial view and an embodiment of FIG. 26.

FIG. 30 illustrates a partial view and an embodiment of FIG. 29.

FIG. 32 illustrates a partial view and an embodiment of FIG. 31.

FIG. 35 illustrates a partial view and an embodiment of FIG. 33.

DETAILED DESCRIPTION

Figure 1:
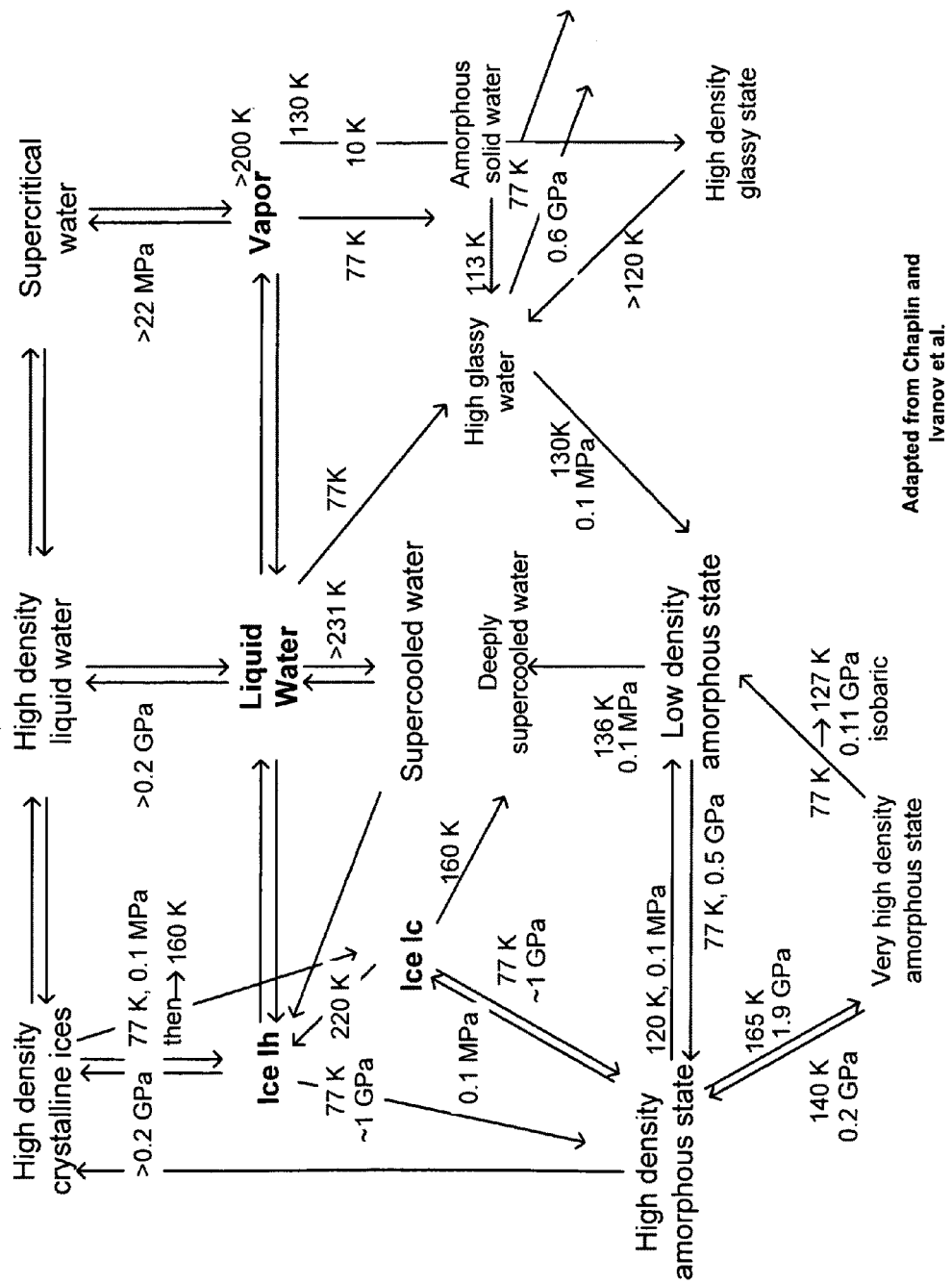
FIG. 1 illustrates particular phases of hydrogen oxide.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In at least one embodiment, at least one composition, therapeutic composition, device, system, product, or method disclosed herein relates to utilizing one or more frozen particles for various purposes. In at least one embodiment, the one or more frozen particles include at least one frozen constituent including at least one of hydrogen oxide, helium, neon, krypton, argon, xenon, nitrogen, chlorine, bromine, oxygen, air, carbon dioxide, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether. In at least one embodiment, at least one of the constituents of the one or more frozen particles is frozen. In at least one embodiment, all of the constituents of the one or more frozen particles are frozen. In at least one embodiment, the at least one composition or therapeutic composition includes one or more frozen solution particles. In at least one embodiment, the composition or therapeutic composition includes one or more frozen solution particles and the composition or therapeutic composition is in at least one crystalline or amorphous phase. In at least one embodiment, the frozen solution particles include at least one of the constituents described herein.

In at least one embodiment, the one or more frozen particles include frozen hydrogen oxide particles. Frozen hydrogen oxide, or typical water ice, exists in several non-crystalline forms. Each of these forms has specific physical characteristics such as density and vibrational spectra. Some of the frozen hydrogen oxide phase transformations are shown in FIG. 1. (See e.g., Chaplin, the worldwide web at lsbu.ac.uk/water; Ivanov et al., Russian J. Gen. Chem. vol. 75, pp. 1851-1856 (2005), each of which is incorporated herein by reference).

Hydrogen oxide (water) has many frozen phases (ices), including crystalline and non-crystalline phases. The crystalline phases generally have the common structure of having hydrogen bonds to four neighboring water molecules, such as two hydrogen atoms near each oxygen atom. Structural data on the known frozen hydrogen oxide polymorphs are shown in Table I, with two known phases of ice XI. (See, e.g., Chaplin, Ibid; and Zheligovskaya, et al., Russian Chem. Rev. 75, pp. 57-76, 2006, each of which is incorporated herein by reference).

TABLE I

Structural data on the ice polymorphs

| Ice polymorph | Density, g/cm³ | Protons | Crystal | Symmetry | Dielectric constant, $\epsilon_S$ | Notes |
| --- | --- | --- | --- | --- | --- | --- |
| Hexagonal ice, Ih | 0.92 | disordered | Hexagonal | One $C_6$ | 97.5 | |
| Cubic ice, Ic | 0.92 | disordered | Cubic | four $C_3$ | | |
| LDA, Ia | 0.94 | disordered | Non-crystalline | | | As prepared, may be mixtures of several types |

TABLE I-continued

Structural data on the ice polymorphs

| Ice polymorph | Density, g/cm³ | Protons | Crystal | Symmetry | Dielectric constant, $\epsilon_S$ | Notes |
|---|---|---|---|---|---|---|
| HAD | 1.17 | disordered | Non-crystalline | | | As prepared, may be mixtures of several types |
| VHDA | 1.25 | disordered | Non-crystalline | | | |
| II | 1.17 | ordered | Rhombohedral | One $C_3$ | 3.66 | |
| III | 1.14 | disordered | Tetragonal | One $C_4$ | 117 | protons may be partially ordered |
| IV | 1.27 | disordered | Rhombohedral | One $C_3$ | | metastable in ice V phase space |
| V | 1.23 | disordered | Monoclinic | One $C_2$ | 144 | protons may be partially ordered |
| VI | 1.31 | disordered | Tetragonal | One $C_4$ | 193 | protons can be partly ordered |
| VII | 1.50 | disordered | Cubic | four $C_3$ | 150 | two interpenetrating ice Ic frameworks |
| VIII | 1.46 | ordered | Tetragonal | One $C_4$ | 4 | low temperature form of ice VII |
| IX | 1.16 | ordered | Tetragonal | One $C_4$ | 3.74 | low temperature form of ice III, metastable in ice II space |
| X | 2.51 | symmetric | Cubic | four $C_3$ | | symmetric proton form of ice VII |
| XI | 0.92 | ordered | Orthorhombic | three $C_2$ | | low temperature form of ice Ih |
| XI | >2.51 | symmetric | Hexagonal close packed | distorted | | Found in simulations only |
| XII | 1.29 | disordered | Tetragonal | One $C_4$ | | metastable in ice V phase space |
| XIII | 1.23 | ordered | Monoclinic | One $C_2$ | | ordered form of ice V phase |
| XIV | 1.29 | mostly ordered | Orthorhombic | One $C_4$ | | ordered form of ice XII phase |
| XV | 1.31 (?) | ordered | ? | ? | | ordered form of ice VI phase |

Cooling liquid hydrogen oxide below its standard freezing point typically results in the formation of frozen hexagonal ice. However, if the hydrogen oxide is pure and cooled slowly, the liquid hydrogen oxide can be supercooled to approximately −42° C. Amorphous solids harden without crystallizing, such that if hydrogen oxide is cooled rapidly it results in formation of a glass-like state, for example, hyperquenched glassy water. (See e.g., Debenedetti, J. Phys. Condens. Matter, vol. 15, pp. R1669-R1726 (2003), and as cited by Chaplin, worldwideweb at lsbu.ac.uk/water; each of which is incorporated herein by reference.) Generally, hyperquenched glassy water is formed by rapidly spraying a fine mist of micrometer-sized hydrogen oxide droplets into very cold liquefied gas, such as propane. Alternatively, a fine mist of hydrogen oxide can be sprayed onto a very cold frozen substrate, at or below approximately −193° C. Hyperquenched glassy water may also be formed by cooling capillary tubes containing bulk liquid water (~100 μm diameter) with liquid helium at approximately −269° C.

Figure 2:
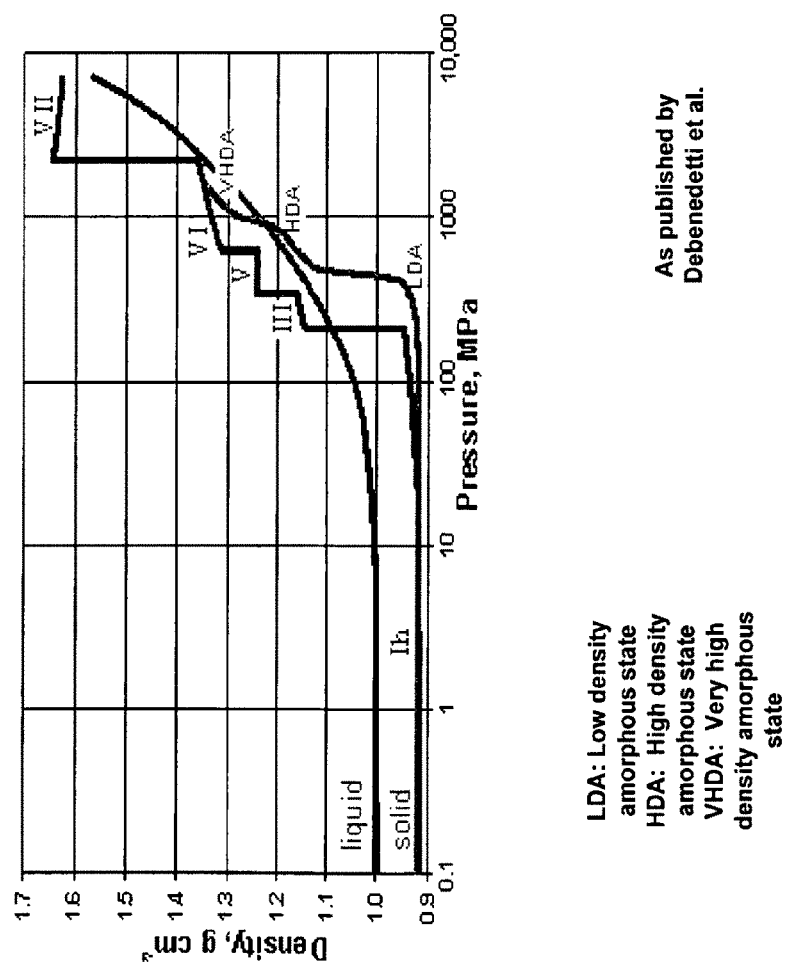
FIG. 2 illustrates the density of hydrogen oxide at various pressure points.
Figure 3:
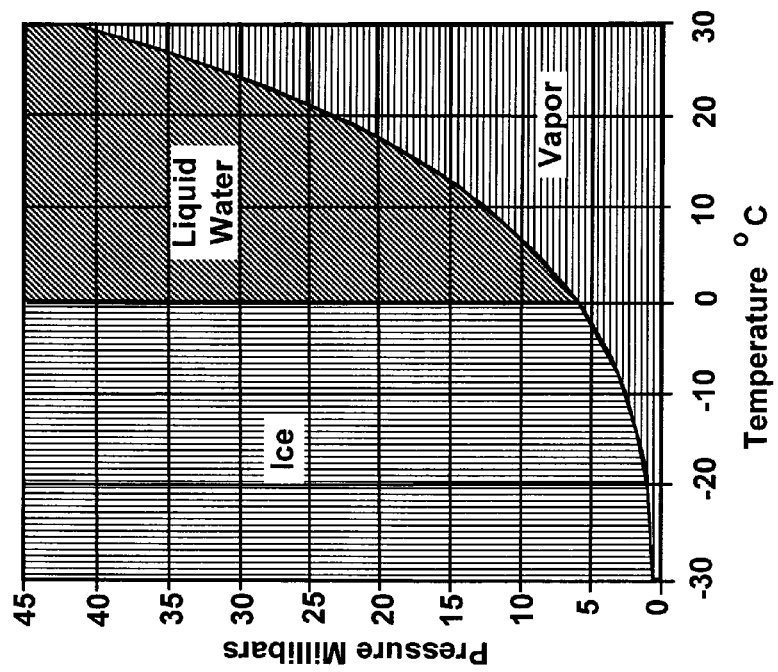
FIG. 3 illustrates particular phases of hydrogen oxide at various pressure and temperature points.
Figure 4:
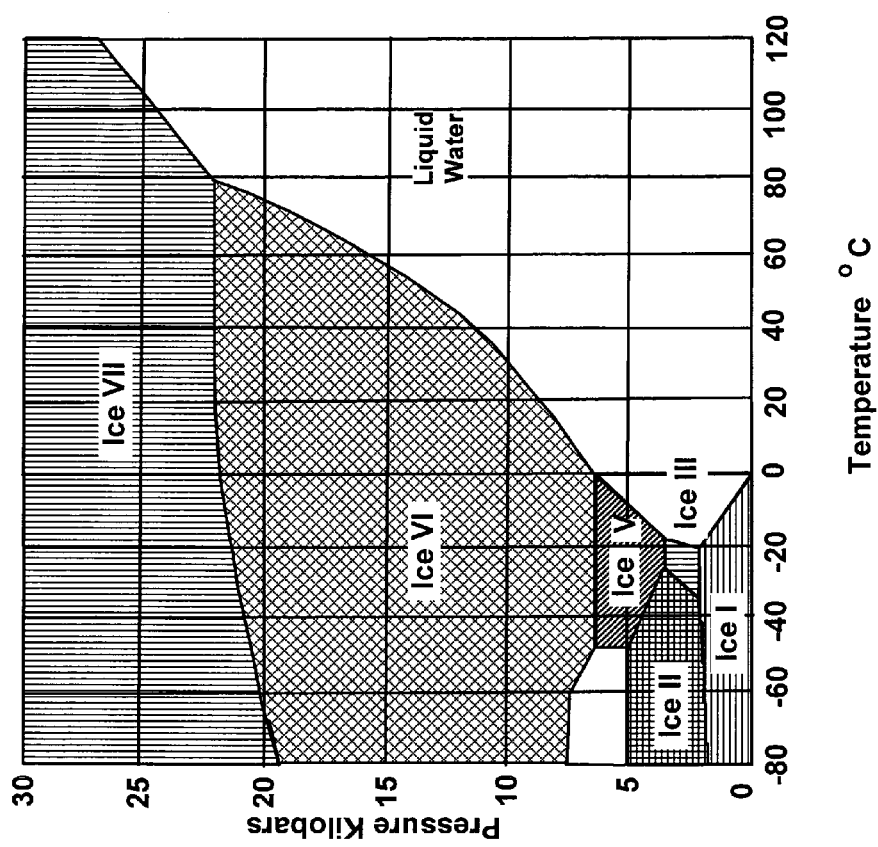
FIG. 4 illustrates particular phases of hydrogen oxide at various pressure and temperature points.

As shown in FIGS. 1-4, hydrogen oxide attains various structures and phases depending upon the temperature or pressure of the environment. As indicated in FIG. 1, for example, hydrogen oxide ice Ic is derived from high density amorphous water or deeply supercooled liquid water, when put under low temperature or higher pressure. Likewise, as indicated in FIG. 2, the hydrogen oxide has a greater density as a liquid than as a solid under ambient conditions (ice Ih). However, at increasing pressure, at least ice stages III, V, VI, and VII exhibit a greater density than liquid hydrogen oxide. FIG. 3 indicates the phase diagram for hydrogen oxide based on pressure and temperature variance, while FIG. 4 shows the specific sub-categories of hydrogen oxide based on physical properties, such as structure and density, among others, as the temperature and pressure vary.

Similarly, amorphous solid water is formed from the slow deposition of hydrogen oxide vapor on a cold metal crystal surface (at less than approximately 2 nm/s), below the temperature of approximately −153° C. Amorphous solid water is a viscous semi-solid material that has a density of approximately 0.94 g/cm³ and harbors gaps and spaces in its structure, as well as reactive hydrogen bonds. These structures are removed by annealing under vacuum pressure, which allows the material to convert to a high density glassy water or low density amorphous ice, depending on the temperature. Typically, high density glassy water, which has a density of approximately 1.1 g/cm³, is formed by vapor deposition at approximately −263° C.

Low-density amorphous (LDA) ice also occurs from heating high-density amorphous (HDA) ice to just above approximately −153° C. at atmospheric pressure, and transforms to cubic ice at approximately −113° C. to −123° C. Low-density amorphous ice is also prepared by submitting low-pressure phases (Ih, Ic, XI, etc.) to high pressure (approximately 1.0 GPa) at low temperatures (e.g., below approximately −148° C.).

Very-high density amorphous (VHDA) ice is a viscous water state with a density of approximately 1.25 g/cm³, and is prepared by heating high-density amorphous ice to just above approximately −113° C. and approximately 1.15 GPa. When very-high density amorphous ice is heated at different pressures between 0.3 and 2 GPa, it re-crystallizes into only the proton disordered ices III, IV, V, XII, VI and VII in order of increasing pressure, but does not typically re-crystallize into the proton ordered phases (e.g., ice II).

Typically, the density of liquid water increases with increased pressure. When liquid water approaches the critical point in the liquid-vapor phase, water enters a supercritical phase where it exists as small but liquid-like hydrogen-bonded clusters dispersed within a gas-like phase and its physical properties vary according to changing density. Supercritical water is an excellent solvent for non-polar molecules, due to its low dielectric constant and poor hydrogen bonding. Due to these same properties, supercritical water is typically not a good solvent for electrolytes, which tend to form ionic bonds.

As indicated in FIG. 2, hexagonal ice is less dense than liquid water, whereas the other ice phases are all denser and phase changes occur near the liquid and solid densities (See e.g., Loerting et al., J. Phys.: Condens. Matter vol. 18, R919-R977 (2006), which is incorporated herein by reference). Liquid water density varies with change in temperature or pressure, whereas the density of amorphous ice varies only with change in pressure, but not temperature.

Hydrogen oxide has a high heat of vaporization (approximately 40.7 kJ/mol), and a high heat of sublimation (approximately 51.059 kJ/mol at 0° C.), which allows for the frozen particles to remain intact for a short time period during which the particles are delivered to one or more cells or tissues. These properties further enable the frozen particles to serve as particles for delivery of at least one therapeutic composition to one or more cells or tissues.

Hydrogen oxide becomes more viscous as the temperature is decreased to below approximately 33° C., or the pressure is increased. Frozen particles may include a "solid," such as true solids, semi-solids, and viscous fluid, such as gels, hydrogels, or sols. Frozen particles may include particles that are at least partially frozen, or are entirely frozen. Compositions including one or more particles may include one or more subset groups of one or more particles, some of which may be entirely frozen and some of which may be at least partially frozen. Such compositions may include multiple different compositions, where the group of frozen particles includes at least one subset that includes multiple particles, wherein each particle has an individual therapeutic agent or unique composition. The group of frozen particles may also include at least one subset of multiple particles, wherein each particle includes multiple agents (including therapeutic agents).

A particular plurality of compositions or therapeutic compositions may include multiple frozen particles where various multiple agents are associated with a single particle. Likewise, a particular plurality of compositions or therapeutic compositions may include various multiple agents, where each individual agent is associated with a single frozen particle. In at least one embodiment, a plurality of compositions or therapeutic compositions may include any number of subsets of frozen particles associated with a particular therapeutic agent or other constituent. During the course of any particular method described herein, one or more plurality of compositions or therapeutic compositions, or any particular subset thereof, may be administered in a single treatment.

In at least one embodiment, the one or more frozen particles exist at about 30° C., about 20° C., about 10° C., about 5° C., about 0° C., about −10° C. about −20° C., about −30° C., about −40° C., about −50° C., about −60° C., about −70° C., about −75° C., about −80° C., about −85° C., about −90° C., about −95° C., about −100° C., about −120° C., about −150° C., about −180° C., about −200° C., about −220° C., about −250° C., or any value less than or therebetween.

In certain instances, the one or more frozen particles are utilized at a very cold temperature so that effective penetration of a biological tissue is achieved. In certain instances, the one or more frozen particles are utilized at warmer temperatures, particularly if the contents of the one or more frozen particles include agents that have warmer freezing temperatures. For example, the freezing point of nitrogen is approximately −210° C., whereas the freezing point of dimethyl sulfoxide (DMSO) is approximately 18.45° C. Thus, frozen particles of DMSO can be utilized or administered at a warmer temperature than can frozen particles of nitrogen.

Ice Ic is generally formed by condensation of water vapor, at ambient pressure and low temperatures (less than approximately −80° C.), or below approximately −38° C. as a mist. (See e.g., Murray et al., Phys. Chem. Chem. Phys. Vol. 8, pp. 186-192 (2006), which is incorporated herein by reference). Ice Ic is also prepared by reducing the pressure on high-pressure hydrogen oxide ice at approximately −196° C. It may be the preferred phase for ice formed from hydrogen oxide droplets smaller than about 15 nm in radius, particularly at low temperatures (e.g., −113° C. to −53° C.). (See e.g., Johari, J. Chem. Phys. vol. 122 pp. 194504 (2005); Zhang, et al., Chem. Phys. Lett. vol. 421, pp. 251-255 (2006), each of which is incorporated herein by reference).

Ice Ih constitutes a large portion of naturally-occurring snow and ice. Since hexagonal ice exhibits changes in the hydrogen bonding, ice Ih shows anomalous reduction in thermal conductivity with increasing pressure (as does cubic ice and low-density amorphous ice). (See e.g., Andersson et al., Phys. Rev. B vol. 65 pp. 140201.1-14201.4 (2002), which is incorporated herein by reference).

Ice II maintains a general rhombohedral unit shape, similar to ice I. The density of ice II is approximately 1.17 g/cm³. Ice III maintains a general tetragonal unit shape, with a density of approximately 1.14 g/cm³. Ice VI also maintains a general tetragonal unit shape, with a density of approximately 1.31 g/cm³. Ice VII is primarily composed of multiple intercalating ice Ic lattices, and has a density of approximately 1.66 g/cm³.

In at least one embodiment, the therapeutic composition includes at least one of a solid, liquid, or gas. In at least one embodiment, the therapeutic composition includes one or more of a suspension, mixture, solution, sol, clathrate, colloid, emulsion, microemulsion, aerosol, ointment, capsule, powder, tablet, suppository, cream, device, paste, liniment, lotion, ampule, elixir, spray, suspension, syrup, tincture, detection material, polymer, biopolymer, buffer, adjuvant, diluent, lubricant, disintegration agent, suspending agent, solvent, colorimetric agent, light-emitting agent, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, or gel.

In at least one embodiment, the at least one adhesive is included in one or more frozen particles. In at least one embodiment, the one or more frozen particles provide a vehicle for the at least one adhesive. In certain instances, at least one adhesive is provided to at least one biological tissue in an inactive form, wherein the at least one adhesive polymerizes or activates upon contact with the at least one biological tissue, or shortly thereafter.

In at least one embodiment, at least one scaffold (e.g., collagen, elastin, protein, carbohydrate, nucleic acid, organic chemical, or other component) is provided with the at least one composition or therapeutic composition for one or more cells. In at least one embodiment, the scaffold provides a matrix for one or more cells. In at least one embodiment, the one or more cells are located in at least one biological tissue.

In at least one embodiment, clathrate compositions are included. Clathrate ice forms from water or other liquids, and contains small amounts of non-polar molecules (generally gases) under moderate pressure of a few MPa, and temperatures close to 0° C. Clathrate structures can vary, but generally allow a minimum amount of small molecules to fit into and stabilize gaps without forming covalent or hydrogen bonds with the hydrogen oxide molecules. Certain clathrates are formed at the interface of the liquid phase, under atmospheric pressure. Clathrates include but are not limited to the structural forms of sI, sII, and sh. In certain instances, noble gases may be used to form clathrate compounds with hydrogen oxide or other molecules. Noble gases generally have low polarizability, and tend to be spherically symmetrical, which allows for solubility with the hydrogen oxide cage. In addition, the solubility of the noble gases increases considerably as the temperature is lowered. The solubility of particular noble gases as clathrates with hydrogen oxide are shown in Table II. (See e.g., Dec et al., J. Solution Chem. vol. 14, pp. 417-429 (1985); Ivanov, et al., J. Struct. Chem. vol. 46, pp. 253-263 (2005); Fernandez-Prini, et al., Elsvier, pp. 73-98 (2004); Ivanov, et al., Russian J. Gen. Chem. vol. 75, pp. 1851-1856 (2005), each of which is incorporated herein by reference.)

approximately 18.45° C., and water or other co-solvents can decrease the freezing point. The freezing point of lactated Ringer's solution is approximately −45° C. These and other materials can be utilized as described herein either alone, or in combination with other materials.

In at least one embodiment, the one or more frozen particles have at least one major dimension of approximately one decimeter or less, approximately one centimeter or less, approximately one millimeter or less, approximately one micrometer or less, approximately one nanometer or less, approximately one picometer or less, or any value therebetween. In at least one embodiment, a plurality of frozen particles is delivered or administered, and the plurality includes at least two subsets of frozen particles which can be differentiated based on size. In at least one embodiment, a plurality of frozen particles includes at least one subset of frozen particles that have at least one major dimension of approximately ten micrometers or less. In at least one embodiment, the at least one major dimension of the one or more frozen particles includes at least one of radius, diameter, length, width, height, or perimeter.

In at least one embodiment, the one or more frozen particles approximate the shape of at least one of a sphere, bullet, flechette, cone, needle, arrow, spear, diamond, pyramid, cylinder, mini ball, shuttlecock, spiral, bell, pear, crystal, cube, spheroid, tetrahedron, crescent, or high aspect ratio shape. The size, shape, weight, or density, as well as other physical parameters of the one or more frozen particles may be adjusted according to a particular composition or therapeutic composition, or desired goal in utilizing the compositions. In at least one embodiment, the one or more frozen particles include a plurality of frozen hydrogen oxide particles that are approximately uniform with regard to size, shape, weight, or density. In at least one embodiment, the one or more frozen particles include an array of different sizes, shapes, weights, or densities.

In at least one embodiment disclosed herein, one or more reinforcement agents may be included in the compositions or therapeutic compositions described. Examples of some reinforcement agents include, but are not limited to, polyaramid, vinylester matrix, metal, ceramic, fiberglass, cellulose, broad carbide, aromatic polyamide, nylon, silk, rayon, acetate,

TABLE II

Solubility properties of the noble gases

| Property | | He | Ne | Ar | Kr | Xe | Rn |
|---|---|---|---|---|---|---|---|
| Atomic number | | 2 | 10 | 18 | 36 | 54 | 86 |
| Atomic radius, Å | | 1.08 | 1.21 | 1.64 | 1.78 | 1.96 | 2.11 |
| $\Delta G\,°$ of solution in $H_2O$ at 25° C., kJ/mol | | 29.41 | 29.03 | 26.25 | 24.80 | 23.42 | |
| $\Delta H\,°$ of solution in $H_2O$ at 25° C., kJ/mol | | −0.59 | −3.80 | −11.98 | −15.29 | −18.99 | |
| $\Delta S\,°$ of solution in $H_2O$ at 25° C., J/molK | | −100.6 | −110.1 | −128.2 | −134.5 | −142.2 | |
| Solubility, mM, 5° C., 101,325 Pa | $H_2O$ | 0.41 | 0.53 | 2.11 | 4.20 | 8.21 | 18.83 |
| | $D_2O$ | 0.49 | 0.61 | 2.38 | 4.61 | 8.91 | 20.41 |
| Solubility minima, ° C. | $H_2O$ | 30 | 50 | 90 | 108 | 110 | |
| | $D_2O$ | 53 | 53 | 98 | 108 | 116 | |

Other materials are included in one or more compositions described herein. For example, liquid nitrogen is nontoxic and inert, with a freezing point at 1 atm pressure of approximately −210° C. Liquid helium is nontoxic and inert, with a freezing point at 367 psi of approximately −272.2° C. Liquid argon is nontoxic and inert with a freezing point at 1 atm pressure of approximately −189.4° C. Liquid neon has a freezing point of approximately −245.95° C., while liquid xenon has a freezing point of approximately −111.9° C. The freezing point of liquid dimethyl sulfoxide (DMSO) is modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, alluvium, sand, sugar, calcite, emery, diamond, novaculite, pumice, rouge, borazon, corundum, zirconia alumina, silicon, silica, frozen hydrogen oxide ice, plant matter, animal matter, or mineral matter. In at least one embodiment, plant matter may include vegetable matter, nuts or nut products or pieces (e.g., almonds), grains (e.g., oatmeal), wood (e.g., wood fibers) or other stalk material, leaf matter, fruit matter (including pits or seeds or parts thereof), and other plant material.

In at least one embodiment, one or more reinforcement agents are made by spinning into a fiber, wire, or filament. Some non-limiting examples of reinforcement fibers can be found at, for example, U.S. Pat. No. 5,855,663; U.S. Pat. No. 5,652,058; KEVLAR® technical guide, Polymer Bulletin, vol. 16, pp. 167-174 (1986), and WO/2003/060002, each of which is incorporated herein by reference.

In at least one embodiment, the one or more reinforcement agents are manufactured into a plate or spheroid. In certain instances, the one or more reinforcement agents are utilized in the form of a resin, powder, solution, flake, sheet, film, ribbon, gel, ball, pellet, or bead. (See e.g., U.S. Pat. No. 5,534,584; U.S. Pat. No. 5,331,046; each of which is incorporated herein by reference). The one or more reinforcement agents may be in the form of a solid, liquid, or gas.

The one or more reinforcement agents are positioned on or in the one or more frozen particles depending on a given context. For example, the positioning of one or more reinforcement agents may consider the particular goal of administering the one or more frozen particles, the components of the at least one composition or therapeutic composition, or the needs or desires of a particular outcome of treatment or administration of the one or more frozen particles. In at least one embodiment, the one or more reinforcement agents are located at least on the surface or beneath the surface of the one or more frozen particles. In at least one embodiment, the one or more reinforcement agents are located within the one or more frozen particles.

Figure 5:
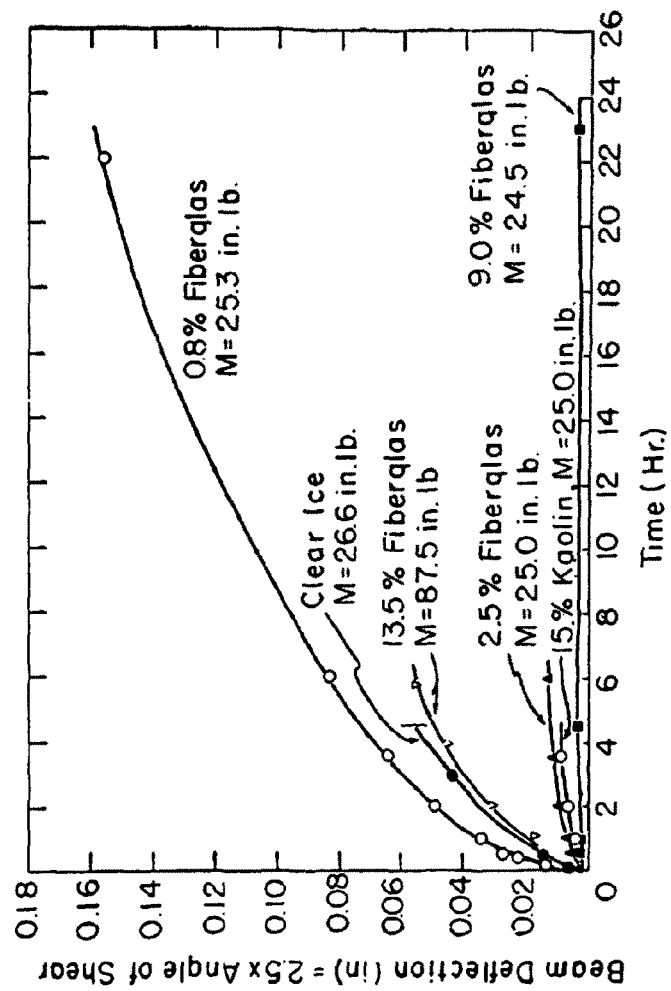
FIG. 5 illustrates the strength of hydrogen oxide samples reinforced with fiberglass or kaolin.
Figure 6:
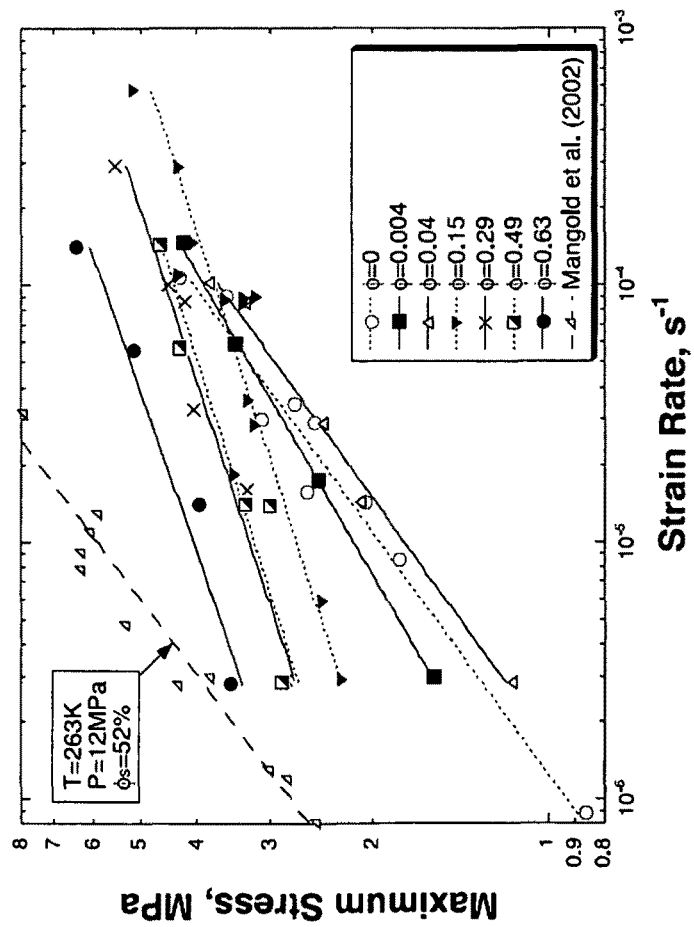
FIG. 6 illustrates the strength of hydrogen oxide samples reinforced with a reinforcement agent.

As shown in FIGS. 5 and 6, the strength of hydrogen oxide ice samples increases when particular reinforcement agents are added. As indicated in FIG. 5, ice samples exhibit increased strength, as measured by beam deflection as an angle of shear when reinforced with fiberglass or kaolin. As indicated in FIG. 6, the maximum stress (in MPa) and strain rate increases when particular reinforcement agents are added to the hydrogen oxide ice samples.

In certain instances, the composition or therapeutic composition described herein includes one or more abrasives may include treated or untreated abrasives, coated abrasives, bonded abrasives, powders, aggregates, composites, or other forms. In at least one embodiment, the one or more abrasives include, but are not limited to include, but are not limited to, polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, alluvium, sand, sugar, calcite, emery, diamond, novaculite, pumice, rouge, borazon, corundum, zirconia alumina, silicon, silica, frozen hydrogen oxide ice, plant matter, animal matter, or mineral matter. In at least one embodiment, plant matter may include vegetable matter, nuts or nut products or pieces (e.g., almonds), grains (e.g., oatmeal), wood (e.g., wood fibers) or other stalk material, leaf matter, fruit matter (including pits or seeds or parts thereof), or other plant material.

In at least one embodiment, a therapeutic composition and methods of delivery to at least one biological tissue include one or more frozen hydrogen oxide particles including at least one therapeutic agent; wherein the one or more hydrogen oxide particles are in one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV.

In at least one embodiment, a therapeutic composition includes one or more frozen solution particles and at least one therapeutic agent; wherein the therapeutic composition is in at least one crystalline or amorphous phase.

In at least one embodiment, the at least one composition or therapeutic composition includes at least one therapeutic agent. (See, e.g., The Merck Index, $14^{th}$ Ed. Merck & Co., Inc., Whitehouse Station, N.J. (2006), which is incorporated herein by reference). Other agents that are approved for use in humans may be utilized as at least one therapeutic agent described herein, and may be found at the U.S. Food and Drug Administration website on the worldwide web at fda.gov, the information at which is incorporated herein by reference.

In certain instances, the one or more frozen particles themselves provide at least one therapeutic benefit. In certain instances, the one or more frozen particles act as vehicles for one or more therapeutic agents that provide at least one therapeutic benefit. The frozen particles acting as vehicles for one or more therapeutic agents may be inert, or may provide additional therapeutic benefit in the overall composition. In at least one embodiment, at least one therapeutic agent is activated during administration of the at least one composition or therapeutic composition to at least one biological tissue. In at least one embodiment, at least one therapeutic agent is activated prior to or subsequent to administration of the at least one composition or therapeutic composition to at least one biological tissue. In at least one embodiment, at least one therapeutic agent is activated after a prolonged time subsequent to administration of the at least one therapeutic composition or composition to at least one biological tissue (e.g. in cases where the therapeutic agent is encased or associated with a polymer or other agent that may insulate one or more reactant or retard the explosive or decomposition process). In at least one embodiment, the composition or therapeutic composition includes at least one activatable therapeutic agent. In at least one embodiment, the composition or therapeutic composition includes at least one activating agent or at least one inactivating agent, or both.

In certain instances, the therapeutic agent includes at least one of an organic or inorganic small molecule, clathrate or caged compound, protocell, coacervate, microsphere, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, glycoprotein, sphingolipid, glycosphingolipid, peptidoglycan, lipid, carbohydrate, metalloprotein, proteoglycan, chromosome, nucleus, acid, base, buffer, protic solvent, aprotic solvent, nitric oxide, nitric oxide synthase, amino acid, micelle, polymer, co-polymer, or piloxymer.

In at least one embodiment, the at least one therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, chemical debridement agent, immunogen, antigen, radioactive agent, apoptotic promoting factor, angiogenic factor, anti-angiogenic factor, hormone, enzymatic factor, enzyme, papain, collagenase, protease, peptidase, elastase, urea, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In at least one embodiment, the nutraceutical includes one or more of a flavonoid, antioxidant, beta-carotene, anthocyanin, alpha-linolenic acid, omega-3 fatty acids, yeast, bacteria, algae, other microorganisms, plant products, or animal products. In at least one embodiment, the analgesic or anesthetic includes one or more of any aminoamid or aminoester local anesthetic, ibuprofen, morphine, codeine, aspirin, acetaminophen, lidocaine/lignocaine, ropivacaine, mepivacaine, benzocaine, chloroprocaine, cocaine, cyclomethycaine, dimethocaine/larocaine, propoxycaine, procaine/novocaine, proparacaine, tetracaine/amethocaine, articaine, bupivacaine, carticaine, cinchocaine/dibucaine, etidocaine, levobupivacaine, piperocaine, prilocaine, trimecaine, saxitoxin, or tetrodotoxin.

In at least one embodiment, the therapeutic agent includes at least one anti-inflammatory agent, including but not limited to steroids, non-steroidal anti-inflammatory drugs, topical anti-inflammatory agents, or subcutaneously administered non-steroidal anti-inflammatory drugs (e.g. diclofenac).

In at least one embodiment, the analgesic includes but is not limited to one or more of paracetamol (acetaminophen), non-steroidal anti-inflammatory drugs (NSAIDs), salicylates, narcotics, or tramadol. In at least one embodiment, the analgesic includes but is not limited to aspirin, rofecoxib, celecoxib, morphine, codeine, oxycodone, hydrocodone, diamorphine, pethidine, buprenorphine, amitriptyline, carbamazepine, bagapentin, pregabalin, ibuprofen, naproxen, lidocaine, a psychotropic agent, orphenadrine, cyclobenzaprine, scopolamine, atropine, gabapentin, methadone, ketobemidone, or piritramide.

In at least one embodiment, the at least one therapeutic agent includes one or more antiseptic, including but not limited to one or more of an alcohol, a quaternary ammonium compound, boric acid, hydrogen peroxide, chlorhexidine gluconate, iodine, mercurochrome, octenidine dihydrochloride, phenol (carbolic acid) compounds, sodium chloride, or sodium hypochlorite.

In at least one embodiment, the antiseptic includes but is not limited to one or more of povidone-iodine, iodine, ethanol, 1-propanol, 2-propanol/isopropanol, benzalkonium chloride, cetyl trimethylammonium bromide, cetylpyridinium chloride, benzethonium chloride, chlorhexidine, octenidine dihydrochloride, or carbolic acid.

In at least one embodiment, the antimicrobial agent includes at least one of an anti-fungal agent, antibiotic agent, anti-bacterial, anti-parasitic agent, or anti-worm agent. In certain instances, the antimicrobial agent may occur in nature, or it may be synthetic.

In at least one embodiment, the at least one therapeutic agent includes one or more anti-tumor agent, at least one of which may also be identified as a cytotoxic agent, or chemotherapy agent. Non-limiting examples of an anti-tumor agent for use as described herein include at least one of an alkylating agent, antimetabolite, anthracycline, plant alkaloid (such as paclitaxel), topoisomerase inhibitor, monoclonal antibody, or tyrosine kinase inhibitor. In at least one embodiment, the therapeutic agent includes one or more of imatinib, mechlorethamine, cyclophosphamide, chlorambucil, azathioprine, mercaptopurine, vinca alkaloid, taxane, vincristine, vinblastine, vinorelbine, vindesine, podophyllotoxin, etoposide, teniposide, amsacrine, dactinomycin, trastuzumab, cetuximab, rituximab, bevacizumab, dexamethasone, finasteride, tamoxifen, goserelin, telomerase inhibitor, dichloroacetate, aminopterin, methotrexate, pemetrexed, raltitrexed, cladribine, clofarabine, fludarabine, pentostatin, thioguanine, cytarabine, decitabine, fluorouracil/capecitabine, floxuridine, gemcitabine, enocitabine, sapacitabine, chloromethine, cyclophosphamide, ifosfamide, melphalan, bendamustine, trofosfamide, uramustine, carmustine, fotemustine, lomustine, nimustine, prednimustine, ranimustine, semustine, spretpozocin, carboplatin, cisplatin, nedaplatin, oxaliplatin, triplatin tetranitrate, satraplatin, busulfan, mannosulfan, treosulfan, procarbazine, decarbazine, temozolomide, carboquone, ThioTEPA, triaziquone, triethylenemelamine, docetaxel, larotaxel, ortataxel, tesetaxel, vinflunine, ixabepilone, aclarubicin, daunorubicin, doxorubicin, epirubicin, idarubicin, amrubicin, pirarubicin, valrubicin, zorubicin, metoxantrone, pixantrone, actinomycin, bleomycin, mitomycin, plicamycin, hydroxyurea, camptothecin, topotecan, irinotecan, rubitecan, belotecan, altretamine, amsacrine, bexarotene, estramustine, irofulven, trabectedin, cetuximab, panitumumab, trastuzumab, rituximab, tositumomab, alemtuzumab, bevacizumab, edrecolomab, gemtuzumab, axitinib, bosutinib, cediranib, dasatinib, erlotinib, gefitinib, imatinib, lapatinib, lestaurtinib, nilotinib, semaxanib, sorafenib, sunitinib, vandetanib, alvocidib, seliciclib, aflibercept, denileukin diftitox, aminolevulnic acid, efaproxiral, porfimer sodium, talaporfin, temoporfin, verteporfin, alitretinoin, tretinoin, anagrelide, arsenic trioxide, asparaginase/pegaspergase, atrasentan, bortezomib, carmofur, celecoxib, demecolcine, elesclomol, elasamitrucin, etoglucid, lonidamine, lucanthone, masoprocol, mitobronitol, mitoguanzone, mitotane, oblimersen, omacetaxine, sitimagene ceradenovec, tegafur, testolactone, tiazofurine, tipifarnib, or vorinostat.

In at least one embodiment, at least one nutraceutical is included. At least one nutraceutical includes but is not limited to one or more of an extract of plant or animal matter (e.g., an oil, aqueous, or solid extract), a vitamin, a mineral, a mixture or solution, a food supplement, a food additive, a food fortification element, or other nutraceutical. In at least one embodiment, at least one nutraceutical includes but is not limited to resveratrol, an antioxidant, psyllium, sulforaphane, isoflavonoid, alpha-linolenic acid, beta-carotene, anthocyanins, phytoestrogens, polyphenols, polyphenons, catechins, benzenediols, tannins, phenylpropanoids, caffeine, alcohol, or others.

In at least one embodiment, at least one therapeutic agent includes one or more vaccine. In at least one embodiment, the therapeutic composition including at least one vaccine includes at least one prophylactic vaccine or therapeutic vaccine. In at least one embodiment, the at least one therapeutic vaccine includes at least one anti-cancer vaccine. In at least one embodiment, the at least one vaccine includes at least one of an anti-tumor agent, antimicrobial agent, anti-viral agent, immunogen, antigen, live microbe, dead microbe, attenuated microbe, microbe or component thereof, live virus, recombinant virus, killed virus, attenuated virus, virus component, plasmid DNA, nucleic acid, amino acid, peptide, protein, glycopeptide, proteoglycan, glycoprotein, glycolipid, sphingolipid, glycosphingolipid, cancer cell or component thereof, organic or inorganic small molecule, or toxoid.

One or more vaccine may include but not be limited to vaccines containing killed microorganisms (such as vaccines for flu, cholera, bubonic plague, and hepatitis A), vaccines containing live, attenuated virus or other microorganisms (such as vaccines for yellow fever, measles, rubella, and mumps), live vaccine (such as vaccines for tuberculosis), toxoid (such as vaccines for tetanus, diphtheria, and crotalis atrox), subunit of inactivated or attenuated microorganisms (such as vaccines for HBV, VLP, and HPV), conjugate vaccines (such as vaccines for *H. influenzae* type B), recombinant vector, DNA vaccination. In at least one embodiment, the at least one vaccine includes but is not limited to rubella, polio, measles, mumps, chickenpox, typhoid, shingles, hepatitis A, hepatitis B, diphtheria, pertussis, rotavirus, influenza, meningococcal disease, pneumonia, tetanus, rattlesnake venom, virus-like particle, or human papillomavirus, or anti-cancer vaccine.

In at least one embodiment, the at least one therapeutic agent includes at least one adjuvant. The at least one adjuvant may include but not be limited to one or more organic or inorganic compounds. The at least one adjuvant may include but not be limited to at least one of a liposome, virosome, lipid, phospholipid, mineral salt, single-stranded DNA, double-stranded RNA, lipopolysaccharide, molecular antigen cage, CpG motif, microbial cell wall or component thereof, squalene, oil emulsion, surfactant, saponin, isolated microbial toxin, modified microbial toxin, endogenous immunomodulator, or cytokine.

In one non-limiting example, a therapeutic composition includes one or more frozen particles including paclitaxel and at least one other constituent including at least one of air, oxygen, nitrogen, carbon dioxide, hydrogen oxide, helium, neon, xenon, krypton, chlorine, bromine, or argon.

In one non-limiting embodiment, a therapeutic composition includes one or more frozen particles including one or more pegylated cytokines or one or more anti-tumor compounds; wherein the one or more frozen particles include nitrogen, air, oxygen, carbon dioxide, hydrogen oxide, helium, xenon, krypton, chlorine, bromine, or argon.

In at least one embodiment, the one or more frozen particles provide a vehicle for delivery of the therapeutic agent. In at least one embodiment, the at least one therapeutic agent is located in at least one distinct region of the one or more frozen particles. In at least one embodiment, the at least one therapeutic agent is located in a physically or chemically separable compartment from at least one other region of the one or more frozen particles. In at least one embodiment, the at least one therapeutic agent is located on the surface or beneath the surface of the one or more frozen particles. In at least one embodiment, the at least one therapeutic agent is physically or chemically segregated from at least one other portion of the therapeutic composition. In at least one embodiment, the at least one distinct region of the particle is segregated by at least one of an impermeable, permeable, or semi-permeable partition. In certain instances, the therapeutic agent separates from the rest of the frozen particle upon administration of the therapeutic agent to a biological tissue.

As described herein, at least one embodiment includes administering at least one of a polymer, biopolymer, nanoparticle, or detection material in addition to a composition or therapeutic composition (including at least one vaccine). Such polymer, biopolymer, nanoparticle, or detection material may allow for visualization of the administration process, or provide other benefits (including therapeutic benefits).

In certain instances, the detection material may be located on or in the one or more frozen particles, or it may be intermixed with the one or more frozen particles. In certain instances, the detection material provides a "tracer" agent that allows for visualization of one or more locations of administration of the at least one therapeutic composition, or the at least one frozen particle. Thus, in certain instances the detection material is located on the at least one therapeutic composition or the at least one frozen particle. In other instances, the detection material is separate from the at least one therapeutic composition or the at least one frozen particle and forms a mixture with the therapeutic composition or frozen particles or is administered at approximately the same time, in approximately the same place, or in approximately the same manner as the one or more therapeutic compositions or frozen particles.

In at least one embodiment, detection material includes a detectable label including but not limited to, a colorimetric label, a radioactive label, a light-emitting label (such as a luminescent compound, a fluorescent compound, a phosphorescent compound, or a quantum dot), a nucleic acid label, a protein label, an antibody label, a ligand label, a receptor label, a magnetic label, or other detectable label. In at least one embodiment, the at least one detection material includes but is not limited to at least one electronic identification device. In at least one embodiment, the at least one electronic identification device includes at least one radio frequency identification device.

In at least one embodiment, the at least one detection material includes but is not limited to, at least one radioactive element. In at least one embodiment, the radioactive element includes but is not limited to $^{32}P$, $^{35}S$, $^{13}C$, $^{131}I$, $^{191}Ir$, $^{192}Ir$, $^{193}Ir$, $^{201}Tl$, or $^{3}H$. In at least one embodiment, the at least one detection material includes at least one colorimetric substance. In at least one embodiment, the at least one colorimetric substance includes one or more of an inorganic, organic, biological, natural, artificial, or synthetic substance. The colorimetric substance may include, but not be limited to a dye, pigment, or a light-emitting substance, such as a luminescent substance, a fluorescent substance, phosphorescent substance, or quantum dot. In at least one embodiment, the at least one colorimetric substance is biocompatible.

Some examples of colorimetric substances include, but are not limited to, colored agents that have an affinity to a substrate, such as acid dyes (e.g., water-soluble anionic dyes), basic dyes (e.g., water-soluble cationic dyes), direct or substantive dyes (e.g., stains for nucleic acids, proteins, lipids, carbohydrates, cell populations, tissues, or organelles), mordant dyes, vat dyes, reactive dyes, disperse dyes, azo dyes, sulfur dyes, food dyes, solvent dyes, carbene dyes, or others. Some examples of chromophores that may be utilized include, but are not limited to, dyes that are based on or derivatives of acridine, anthraquinone, arymethane (e.g., diphenyl methane, triphenyl methane), —N═N azo structure, phthalocyanine, diazonium salts, —NO₂ nitro functional group, —N═O nitroso functional group, phthalocyanine, quinine, azin, eurhodin, safranin, indamin, indophenol, oxazin, oxazone, thiazin, thiazole, xanthene, fluorine, pyronin, fluorine, rhodamine, or others. In at least one embodiment, the colorimetric substance includes trypan blue.

In at least one embodiment, the colorimetric substance includes one or more fluorescent tags, including but not limited to fluorescein, phycobilin, phycoerythrin, phycourobilin, chlorophyll, phycocyanin, allophycocyanin, green fluorescent protein, or others. In at least one embodiment, the colorimeteric substance includes at least one light-emitting substance, including but not limited to luminescent substances (e.g. bioluminescent substances, chemiluminescent substances, luciferin, isoluminol, luminescent minerals, etc.).

In at least one embodiment, the at least one detection material includes but is not limited to at least one of a diamagnetic particle, ferromagnetic particle, paramagnetic particle, super paramagnetic contrast agent, or other magnetic particle.

In at least one embodiment, a method or composition described herein includes one or more explosive materials.

Explosive materials are typically chemically or energetically unstable or produce a sudden expansion of the material with a change in pressure. Such a sudden expansion of the material under pressure changes is generally accompanied by the production of heat. Explosive materials are generally differentiated according to their decomposition rates. Generally, a chemical decomposition rate of an explosive material takes years, days, hours, minutes, seconds, or a fraction of a second. Certain explosive materials are relatively stable, and may maintain their explosive ability for some amount of time. Other explosive materials have relatively high rates of decomposition and detonate rapidly.

Explosive materials may contain at least one oxidizer that provides fuel for certain explosive materials. In certain instances, the oxidizer may be an oxidizing element, such as oxygen. In certain instances, the oxidizer reacts with a reactive metal; an example of such a compound includes reacting fine metal powder (e.g., aluminum or magnesium) with an oxidizer (e.g., potassium chlorate or perchlorate). Chemically pure compounds may have high decomposition rates and lead to an explosion, including but not limited to nitroglycerin, acetone peroxide, trinitrotoluene, nitrocellulose, carbon, carbon monoxide, chlorine, potassium nitrate, sulfur, nitrogen compounds (such as nitrite, nitrate, and azide), potassium chlorate and potassium nitrate, hydrogen, ammonium nitrate, phosphorous, dinitrogen tetroxide, or others. In at least one embodiment, one or more mixtures of organic materials and oxidizers are included. In at least one embodiment, one or more mixtures of reactive metals and oxidizers or oils are included.

In at least one embodiment, the one or more explosive materials include carbon dioxide gas. Carbon dioxide gas can be entrapped into various compositions or therapeutic compositions described herein. One method of incorporating carbon dioxide gas into at least one composition or therapeutic composition includes liquefying the composition or therapeutic composition and introducing carbon dioxide gas while maintaining the mixture under pressure. (See e.g., U.S. Pat. Nos. 4,289,794; 4,289,790; 4,262,029; 5,439,698, each of which is incorporated herein by reference).

In at least one embodiment, the one or more explosive materials include sodium bicarbonate. In at least one embodiment, the one or more explosive materials include citric acid. In at least one embodiment, the one or more explosive materials include sodium bicarbonate and citric acid. In at least one embodiment, the one or more explosive materials include hydrogen peroxide.

In certain instances, the at least one composition or therapeutic composition explodes during administration of the composition or therapeutic composition. In certain instances, the at least one composition or therapeutic composition explodes prior to or subsequent to administration of the composition or therapeutic composition to at least one biological tissue. In certain instances, the at least one composition or therapeutic composition explodes after a prolonged time subsequent to administration or delivery to at least one biological tissue (e.g. in cases where the explosive material is encased or associated with a polymer or other agent that may insulate one or more reactant or retard the explosive or decomposition process).

In at least one embodiment, at least one gasified frozen particle is formed by contacting fluid with gas under high pressure for a sufficient time period to form a gas hydrate. This gas hydrate is then cooled to a lower temperature in order to freeze the remaining unreacted fluid and entrap the gas hydrate. As one non-limiting example, aqueous liquid and carbon dioxide were kept in contact at approximately 0° C. for a time sufficient under a pressure range including at least approximately 200 psig to approximately 600 psig, while permitting absorption in the liquid of the gas in bound form and formation of the gasified ice. This process yields approximately 25-27.5 milliliters of gas per gram of ice. (See e.g., U.S. Pat. Nos. 4,487,023; 2,975,603; 3,086,370; 3,217,503, and 4,404,807, each of which is incorporated herein by reference).

Similarly, as described in U.S. Pat. No. 2,975,603, which is incorporated herein by reference, water contacted with carbon dioxide at a pressure of approximately 400 psig, in a temperature bath of approximately 0° C., is subsequently placed at −10° C. for 24 hours to effect degasification. As described in U.S. Pat. No. 2,975,603, the resulting product yields approximately 75 volumes of carbon dioxide per gram of ice. Additionally, as described in U.S. Pat. No. 3,086,370, which is incorporated herein by reference, gasified ice products are produced in a similar manner that contain other gases, such as nitrous oxide, sulfur-containing gases, chlorine-containing gases, inert gases, or carbon monoxide.

In at least one embodiment, compositions described herein include one or more explosive materials that may include, for example, at least one of a high explosive or a low explosive. In at least one embodiment, the one or more explosive materials include at least one of carbon dioxide, nitroglycerine, or a reactive metal. In certain instances, one or more compositions disclosed herein, including therapeutic compositions, maintain one or more explosive properties. In certain instances, the one or more explosive properties are the result of activation of one or more explosive materials. In certain instances, the one or more explosive properties are the result of inherent tendencies of the compositions themselves. In certain instances, the one or more explosive properties relate to an external event or stimulus, such as a change in temperature or pressure. In certain instances, the one or more explosive properties relate to a change in light intensity. In certain instances, the one or more explosive properties relate to a change in the composition upon administration or contact with at least one composition, cell, tissue, or subject. In certain instances, the one or more explosive properties result from a temperature or pressure increase relating to penetration of at least one cell, tissue, or subject. In certain instances, the one or more explosive properties result from contact with water or other moisture in a cell or tissue. In addition to the intensity of the one or more explosives, the one or more explosive materials may differ with regard to the volatility, density, toxicity, hygroscopicity, or brisance of a particular explosive material.

In at least one embodiment, at least one pharmaceutically-acceptable carrier or excipient is included in a therapeutic composition. The at least one pharmaceutically-acceptable carrier or excipient may take the form of a solid, liquid, gas, or any combination thereof. In certain instances, the at least one pharmaceutically-acceptable carrier or excipient includes one or more of air, oxygen, nitrogen, carbon dioxide, hydrogen oxide, helium, neon, xenon, krypton, chlorine, bromine, or argon. In at least one embodiment, the at least one pharmaceutically-acceptable carrier or excipient includes but is not limited to polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether. In at least one embodiment, the at least one pharmaceutically-acceptable carrier or excipient functions as a vehicle, or means to transport another agent. In at least one embodiment, the at least one pharmaceutically-acceptable carrier or excipient provides at least one clinical benefit.

As described herein, at least one composition or therapeutic composition described herein is useful in one or more methods, including one or more of a method for abrasion of at least one biological tissue surface of a subject by delivering at least one composition to at least one surface of at least one biological tissue of a subject in a manner sufficient to abrade the at least one surface of the at least one biological tissue; a method of delivering at least one therapeutic agent to at least one biological tissue; a method of vaccinating a subject; a method of treating a tissue related to transplantation; a method for cleaning one or more wounds; a method for debridement of tissue or cells; a method for removing material from one or more blood vessel, and others. These and other methods include utilizing one or more composition or therapeutic composition described herein.

In at least one embodiment, a method for abrasion of at least one biological tissue surface of a subject includes delivering at least one composition to at least one surface of at least one biological tissue of a subject in a manner sufficient to abrade the at least one surface of the at least one biological tissue.

As indicated herein, in at least one embodiment, a method for providing at least one therapeutic agent to at least one biological tissue of a subject is included. In at least one embodiment, the at least one therapeutic agent is delivered to at least one biological tissue prior to, during, or subsequent to surgery. In certain instances, at least one therapeutic agent includes one or more therapeutic agents described herein. In at least one embodiment, a method of providing at least one therapeutic agent to at least one biological tissue of a subject includes delivering at least one therapeutic composition to at least one biological tissue, including one or more frozen hydrogen oxide particles including at least one therapeutic agent; wherein the at least one therapeutic composition has at least one crystalline or amorphous phase.

In certain aspects, a method relates to vaccinating a subject by administering at least one therapeutic composition that includes at least one vaccine. The therapeutic composition can be administered singularly, or in conjunction with another treatment, such as surface abrasion therapy. In at least one embodiment, a method of vaccinating a subject includes administering to a subject at least one therapeutic composition; wherein the at least one therapeutic composition includes one or more frozen hydrogen oxide particles, and at least one vaccine; wherein the therapeutic composition has at least one crystalline or amorphous phase.

In at least one embodiment, a method of vaccinating a subject includes administering to a subject at least one therapeutic composition; wherein the at least one therapeutic composition includes one or more frozen particles, including at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether; and at least one vaccine.

As disclosed herein for other embodiments, a method of vaccinating a subject includes administering at least one therapeutic composition that includes one or more abrasives, one or more reinforcement agents, or one or more explosive materials. In at least one embodiment, the vaccine described herein relates to a therapeutic or prophylactic vaccine, and in certain instances the vaccine relates to an anti-cancer vaccine. In at least one embodiment, the one or more abrasives are the same as the one or more reinforcement agents, or the one or more explosive materials. In at least one embodiment, the one or more abrasives are different than the one or more reinforcement agents. In at least one embodiment, the one or more abrasives are different than the one or more explosive materials. In at least one embodiment, the subject receiving the vaccine includes one or more of a vertebrate or invertebrate, insect cells, insects, bacteria, algae, plankton, or protozoa. In at least one embodiment, the at least one subject includes one or more of a reptile, mammal, amphibian, bird, or fish. In at least one embodiment, the at least one subject includes at least one human. In at least one embodiment, the at least one subject includes at least one of livestock, pet, undomesticated herd animal, wild animal, or product animal. In certain instances, the vaccine compositions and methods relate to vaccinating wildlife animals (e.g. vaccinating raccoons for rabies, or bison for brucellosis). In certain instances, the vaccine compositions and methods described herein relate to vaccinating domesticated animals (such as cattle, horses, sheep, or goats). In certain instances, vaccine compositions and methods described herein relate to vaccinating a group of subjects, such as a population, a herd, a pride, a gaggle, a pack, flock, band, cluster, school, brood, troop, colony, or other group. In certain instances, vaccinating a group of subjects is included as a route to regulate or control infection within a group of subjects.

In at least one embodiment, the at least one subject includes at least one of a sheep, goat, frog, dog, cat, rat, mouse, vermin, monkey, duck, horse, cow, pig, chicken, shellfish, fish, turkey, llama, alpaca, bison, wolf, fox, coyote, deer, rabbit, guinea pig, yak, chinchilla, mink, reindeer, elk, deer, raccoon, camel, donkey, or mule.

As discussed herein, particular methods are disclosed for abrading or ablating at least one surface of at least one biological tissue. Abrading at least one surface of at least one biological tissue may entail debridement of at least one biological tissue. In certain instances, debridement may include removal or destruction of dead, damaged, or infected cells or tissues. In certain instances, debridement may be included as part of an additional course of treatment (e.g., surgery). In at least one embodiment, debridement may include penetrating one or more healthy cells or tissues in order to facilitate healing. In at least one embodiment, debridement may include penetrating one or more healthy cells or tissues near in proximity to one or more unhealthy cells or tissues of a subject.

In at least one embodiment, one or more of the debridement methods described herein include penetrating one or more cells or biological tissues of a subject with at least one composition or therapeutic composition, wherein the one or more cells or tissues are chemically or physically partitioned or segregated from at least one other part of the tissue or another tissue. In at least one embodiment, a method for debridement of at least one biological tissue of a subject includes delivering at least one composition or therapeutic composition to at least one biological tissue of a subject wherein the at least one biological tissue is partitioned from another biological tissue or part of another biological tissue, and at least one composition or therapeutic composition penetrates the at last one biological tissue with or without removing any tissue. In certain instances, a therapeutic agent is included with the at least one composition or therapeutic composition, as described herein. In certain instances, one or more reinforcement agents or one or more explosive materials may be included in the at least one composition or therapeutic composition.

In at least one embodiment, the one or more frozen particles are delivered or administered to the at least one biological tissue in a directed manner such that the tissue is etched, tattooed, shaped, carved, or otherwise modified in a directed outcome. In at least one embodiment, the directed manner is predetermined based on information, such as from the at least one biological tissue, the subject, the at least one composition or therapeutic composition, the context of the debridement, the health of the subject, or other information.

In at least one embodiment, the at least one biological tissue includes one or more of skin, scalp, hair, nail, nail bed, teeth, eye, ear, ovary, oviduct, tongue, tonsil, adenoid, liver, bone, pancreas, stomach, blood vessel, blood, lymph, heart, lung, brain, breast, kidney, bladder, urethra, ureter, gall bladder, uterus, prostate, testes, vas deferens, fallopian tubes, large intestine, small intestine, esophagus, oral cavity, nasal cavity, otic cavity, connective tissue, muscle tissue, or adipose tissue. Other cells or tissues of a subject are described herein.

In at least one embodiment, a method for removing one or more materials from at least one biological tissue includes delivering at least one composition or therapeutic composition to the at least one biological tissue. In at least one embodiment, the at least one biological tissue includes one or more tissues described herein. In at least one embodiment, the one or more materials may include one or more materials described herein.

In at least one embodiment, a method for removing one or more materials from at least one blood vessel of at least one subject includes delivering at least one composition to at least one blood vessel of a subject in a manner sufficient to remove one or more materials.

In certain instances, a method for abrasion of at least one biological tissue or organ surface related to transplantation is included. In at least one embodiment, the at least one biological tissue or organ includes one or more of the biological tissues or organs described herein.

In at least one embodiment, a method for abrasion of at least one biological tissue or organ surface related to transplantation includes one or more of biological tissues or organs described herein.

In at least one embodiment, a method for cleaning one or more wounds is included. In at least one embodiment, the one or more wounds are located in at least one biological tissue or organ described herein, including but not limited to skin tissue, muscle tissue, eye tissue, an organ, connective tissue, neoplastic tissue, or bone tissue. In at least one embodiment, the one or more wounds are located in at least one subject described herein. In at least one embodiment, at least one therapeutic agent is included in at least one composition for cleaning one or more wounds. The one or more wounds include but are not limited to at least one of an incision, laceration, abrasion, puncture wound, penetration wound, gunshot wound, iatrogenic wound, severing, infection, ulcer, pressure sore, lesion, chemical burn (including but not limited to exposure to an irritant, plant, or synthetic chemical), dental caries, first-degree burn, second-degree burn, third-degree burn, fourth-degree burn, fifth-degree burn, or sixth-degree burn. In certain instances, the wound may be a result of a bite, such as a bite from an animal, insect, or arachnid.

In at least one embodiment, a plurality of frozen particles is administered for a particular treatment. In some instances, the plurality of frozen particles includes multiple different compositions or therapeutic compositions. In some instances, the plurality of frozen particles includes one or more subsets of one or more frozen particles with common characteristics. In some instances, one or more subsets of the plurality of frozen particles may include but not be limited to one or more frozen particles that have approximately the same size, shape, weight, or density; one or more subsets of the plurality of frozen particles may include but not be limited to one or more frozen particles that include similar therapeutic agents; one or more subsets may include but not be limited to one or more frozen particles that are delivered at approximately the same time, with approximately the same velocity, or to approximately the same location.

In certain instances, it is desirable to deliver the one or more frozen particles to at least one cell or tissue, or administer the one or more frozen particles to at least one subject. In at least one instance, the one or more frozen particles include a plurality of frozen particles that include two or more subsets of frozen particles that are delivered or administered in sequential order. In at least one embodiment, the sequential order is predetermined, based on factors relating to, for example, the at least one cell or tissue, the at least one subject, or the at least one composition or therapeutic composition. In at least one embodiment, the sequential order is determined during the course of delivery or administration of at least one of the one or more frozen particles or at least one composition or therapeutic composition. In at least one embodiment, the sequential order is determined by a software program. In at least one embodiment, the sequential order of delivery is randomized.

In at least one embodiment, the sequential order includes one or more subsets of frozen particles that vary in size, shape, weight, density, location of delivery or administration, time of delivery or administration, or velocity of delivery or administration. In at least one embodiment, one or more subsets of frozen particles are delivered or administered according to a course of treatment (e.g., at least one subset of relatively small frozen particles are administered first, followed by at least one subset of relatively larger frozen particles; at least one subset of frozen particles are administered in a relatively fast velocity, followed by at least one subset of frozen particles administered by a relatively slow velocity; at least one subset of frozen particles approximately shaped as spheroids are administered followed by at least one subset of frozen particles approximately shaped as bullets, etc.).

In at least one embodiment, one or more methods described herein include delivering or administering one or more frozen particles by high velocity impact. In at least one embodiment, the one or more devices that utilize high velocity impact delivery provide at least one of localized delivery, targeted delivery, sustained delivery, modulated delivery, feedback controlled delivery. In some instances, an example of a device that may be used for administering one or more of the compositions described herein includes a handheld device, such as a wand, a pen, a baton, a hose, a sprayer, a gun (e.g., a pellet gun), or other handheld device. In certain instances, the device is at least part of a built-in delivery device, such as may be included in a wall, an overhead device, a corral, a gate, or a device that includes a cavity into which a subject may be placed for administration or delivery of at least one composition described herein. In certain instances, the device has robotic action. In any of these instances, the device may be remotely controlled, for example, by a human or computer program.

In at least one embodiment, delivering the at least one composition, including at least one therapeutic composition, to at least one biological tissue includes at least one of accelerating, ejecting, or propelling, the composition or therapeutic composition toward the at least one biological tissue. In at least one embodiment, the at least one composition is accelerated, ejected, or propelled to or at a predetermined pressure or velocity for delivery of the at least one composition to a desired location on or in the at least one biological tissue. In certain instances, the at least one composition or therapeutic composition is accelerated, ejected, or propelled at a particular pressure or velocity. In certain instances, the at least one composition or therapeutic composition is accelerated, ejected, or propelled at a predetermined pressure or velocity.

The velocity or pressure determined for delivery of the at least one composition to at least one biological tissue depends on certain factors, including but not limited to, size and density of the particle, content of the particle, desired effect or outcome of administration of the particle, density of the target tissue, density of surrounding tissue, type of tissue, architecture of the tissue, and other factors. In certain instances, the desired velocity or pressure for accelerating, ejecting, or propelling the at least one composition described herein will be the minimum velocity or pressure needed to achieve desired penetration of the tissue with the composition, whether for surface abrasion, therapeutic delivery, or other goal.

The means for accelerating, ejecting, or propelling the compositions described herein are non-limiting, and may include general methods for making, formulating, and delivering to at least one biological tissue by carrier gas under pressure, mechanical or electrical impulse assistance, centripetal or centrifugal force, or others, some of which are described herein. (See e.g., U.S. Pat. No. 4,945,050 and PCT application WO 92/01802, each of which is incorporated herein by reference). In certain instances, the one or more frozen particles are made, propelled, accelerated, or ejected simultaneously. Thus, the frozen particles may be made while propelled, the frozen particles may be made while accelerated, the frozen particles may be made while ejected, or any combination thereof.

In at least one embodiment, the one or more frozen particles are delivered or administered by a piezoelectric-type apparatus or device, by ultrasound-mediated transdermal drug transport, or by other device. When a voltage is applied, a piezoelectric-type apparatus generates a pressure pulse by change in shape or size of a chamber containing a fluid (or solid), and the pressure pulse drives the contents from the chamber. In one particular instance, a high velocity device (such as a powderject, air guns, or slingshot type devices) is utilized for injection of particles formulated with at least one therapeutic agent, for example, for therapy or prevention of a disease or condition.

For example, a powderject system, as described by Kumar and Philip (Trop. J. Pharm. Res., vol. 6, No. 1, pp. 633-644 (2007), which is incorporated herein by reference) propels frozen drug particles into the skin by means of high-speed gas flow (such as helium) that is usually painless and causes minimal bleeding or damage to the skin. (See also e.g., Tang et al., Pharm. Res., vol. 19, pp. 1160-69 (2002), which is incorporated herein by reference). As described by Kumar and Philip, particles contained in a cassette between two polycarbonate membranes located at the end of a chamber (Trop. J. Pharm. Res., vol. 6, No. 1, pp. 633-644 (2007), which is incorporated herein by reference). As described by Kumar and Philip, the polycarbonate membranes are ruptured when a carrier gas enters the chamber under high pressure, and the rapid expansion of the gas forms a shock wave that travels down the nozzle at a speed of approximately 600-900 m/s. Kumar and Philip report drug particle velocities of up to about 800 m/s at the nozzle exit, and the momentum density of the particles within the gas flow can be optimized for desired depth of penetration upon delivery to a biological tissue. (Trop. J. Pharm. Res., vol. 6, No. 1, pp. 633-644 (2007), which is incorporated herein by reference). In the powderject system, particle velocity is controlled by nozzle geometry, membrane burst strength, and gas pressure. (See e.g., U.S. Pat. Nos. 5,630,796; and 5,699,880, which are incorporated herein by reference).

Metered-dose transdermal sprays may also be used for delivery of at least one therapeutic composition as described herein. As described by Rathbone, et al., in one particular example, a topical solution containing a volatile then nonvolatile vehicle including a therapeutic agent is administered as a single-phase solution. (See Rathbone, et al., Modified Release of Drug Delivery Technology, NY, Marcel Dekker, Inc. vol. 126, pp. 471-619 (2004), which is incorporated herein by reference). A finite metered-dose application of the formulation to intact skin results in evaporation of the volatile component, leaving the remaining nonvolatile penetration enhancer or therapeutic agent to partition into the stratum corneum and creating a reservoir of the therapeutic agent(s). (See Rathbone, Ibid; and Kumar, et al., Trop. J. Pharm. Res., vol. 6, pp. 633-644 (2007), each of which is incorporated herein by reference).

In addition to these particular examples of devices that can be utilized for administration of the therapeutic compositions described herein, the therapeutic compositions can be administered in conjunction with other delivery devices or avenues. Likewise, the compositions described herein for abrasion of at least one biological tissue can be delivered to the at least one tissue by any means described herein. Some such means for delivery of the compositions described herein include, but are not limited to, ultrasound, iontophoresis (which involves applying an electrical potential across skin or other tissue in order to increase penetration of ionizable drugs), diffusion, electroporation, photomechanical waves (such as by producing pulses with Q-switched or mode-locked lasers to the skin or other tissue), needle-free injections, electro-osmosis, artificial vesicles, laser radiation, magnetophoresis (utilizing a diamagnetic substance for use with a magnetic field for increased penetration of the composition into the biological tissue), microscissuining, controlled heat aided delivery (which involves heating the skin prior to or during therapeutic administration), or tattoos and etchings.

Some non-limiting examples of particular diamagnetic substances include wood, water, organic compounds (such as petroleum), metals (including copper, mercury, gold, bismuth), or benzoic acid.

In one particular example, skin abrasion for superficial resurfacing (e.g., microdermabrasion) can be used to treat acne, scars, hyperpigmentation, and other skin blemishes, as described herein. Microscissuining creates microchannels in the skin by eroding the outer layers of skin with sharp microscopic metal granules (Carlisle Scientific, Carlisle, Mass.), and Med Pharm Ltd (Charlbury, UK) has developed a novel dermal abrasion device (D3S) for the delivery of difficult to formulate therapeutics ranging from hydrophilic low molecular weight compounds to other biopharmaceuticals, and can be utilized in conjunction with administration of at least one therapeutic composition described herein. (See e.g., Roberts, et al., Clin. Exp. Pharmacol. Physiol. vol. 24, pp. 874-9

(1997); Murthy, et al., J. Controlled Rel. vol. 93, pp. 49-57 (2003); each of which is incorporated herein by reference).

In at least one embodiment, Rathbone et al. have described artificial vesicles that mimic cell vesicles (such as TRANS-FERSOMES®, from IDEA AG, Germany) can be utilized for administration of one or more therapeutic composition described herein. Artificial vesicles penetrate the skin barrier along the transcutaneous moisture gradient and causes "virtual" pores between the cells in an organ without affecting its biological properties. (See, e.g., Modified Release Drug Delivery Technology, NY, Marcel Dekker, Inc., vol. 126, pp. 471-619 (2004), which is incorporated herein by reference). In addition, liposomes, and niosomes also serve as carriers and can be utilized in administration of at least one therapeutic composition described herein.

In at least one embodiment, the one or more frozen particles are generated by spraying a jet or mist of the composition constituents into a low temperature environment (solid, liquid, gas, or any combination thereof) such that the compositions freeze and form frozen particles. In at least one embodiment, streams of frozen particles are extruded at low temperatures through fine ducts and into a low temperature environment. In at least one embodiment, the one or more frozen particles are propelled through a nozzle or other delivery apparatus. In at least one embodiment, the one or more frozen particles are delivered by utilizing flash boiling of a cold liquid. In one particular example, liquid nitrogen is flash boiled in order to accelerate, eject, or propel one or more frozen particles for delivery or administration to at least one cell, tissue, or subject. In at least one embodiment, the flash boiling is caused or enhanced by one or more laser pulses (e.g., an infrared laser pulse). In at least one embodiment, the one or more frozen particles are prepared, delivered, or administered by another means.

In at least one embodiment, the at least one composition is propelled using a pressure set at least about 1 psi, about 5 psi, about 10 psi, about 20 psi, about 30 psi, about 40 psi, about 50 psi, at least about 100 psi, at least about 200 psi, at least about 300 psi, at least about 400 psi, at least about 450 psi, at least about 500 psi, at least about 600 psi, at least about 700 psi, at least about 800 psi, at least about 900 psi, at least about 1000 psi, at least about 1100 psi, at least about 1200 psi, at least about 1300 psi, at least about 1400 psi, at least about 1500 psi, about 2000 psi, about 2500 psi, about 3000 psi, about 3500 psi, about 4000 psi, about 5000 psi, about 6000 psi, about 7000 psi, about 8000 psi, about 9000 psi, about 10000 psi, about 20000 psi, about 30000 psi, about 40000 psi, about 50000 psi, or any value therebetween.

In at least one embodiment, the at least one composition is propelled to or at a predetermined velocity for delivery of the at least one composition to a desired location of the at least one biological tissue. In at least one embodiment, the at least one composition is propelled to or at a velocity of approximately 1 m/s, approximately 5 m/s, approximately 10 m/s, approximately 20 m/s, approximately 30 m/s, approximately 40 m/s, approximately 50 m/s, approximately 60 m/s, approximately 70 m/s, approximately 80 m/s, approximately 90 m/s, approximately 100 m/s, approximately 200 m/s, approximately 300 m/s, approximately 400 m/s, approximately 500 m/s, approximately 600 m/s, approximately 700 m/s, approximately 800 m/s, approximately 900 m/s, approximately 1000 m/s, approximately 1500 m/s, approximately 2000 m/s, approximately 3000 m/s, approximately 4000 m/s, approximately 5000 m/s, or any value greater or therebetween.

In at least one embodiment, the at least one composition is accelerated or ejected toward the at least one biological tissue to a velocity of approximately 1 m/s, approximately 5 m/s, approximately 10 m/s, approximately 20 m/s, approximately 30 m/s, approximately 40 m/s, approximately 50 m/s, approximately 60 m/s, approximately 70 m/s, approximately 80 m/s, approximately 90 m/s, approximately 100 m/s, approximately 200 m/s, approximately 300 m/s, approximately 400 m/s, approximately 500 m/s, approximately 600 m/s, approximately 700 m/s, approximately 800 m/s, approximately 900 m/s, approximately 1000 m/s, approximately 1500 m/s, approximately 2000 m/s, approximately 3000 m/s, approximately 4000 m/s, approximately 5000 m/s, or any value greater or therebetween.

In at least one embodiment, delivering at least one composition to at least one biological tissue includes accelerating, ejecting, or propelling a plurality of frozen particles toward the at least one biological tissue. Such a plurality of particles may include at least one embodiment wherein two or more frozen particles of the plurality include one or more similar therapeutic agents. Likewise, a plurality of frozen particles may include at least one embodiment wherein two or more frozen particles include one or more dissimilar therapeutic agents.

As described herein, a plurality of compositions or frozen particles may include one or more subsets, which may be delivered or administered in an order of operations. In at least one embodiment, the order of operations includes delivery or administration in a pattern. In at least one embodiment, the order of operations includes delivery or administration in a predetermined pattern. In at least one embodiment, the order of operations includes delivery or administration in sequential order. In at least one embodiment, the order of operations includes delivery or administration at random.

In at least one embodiment, delivering at least one composition to at least one surface of at least one biological tissue of a subject includes contacting the at least one surface of at least one biological tissue of a subject with the composition. In at least one embodiment, delivering at least one composition to at least one surface of at least one biological tissue of a subject includes contacting the at least one surface of at least one biological tissue of a subject with the one or more frozen particles. In at least one embodiment, delivering at least one composition to at least one surface of at least one biological tissue of a subject includes rupturing one or more cells of at least one surface of at least one biological tissue of a subject with the one or more frozen particles.

In at least one embodiment, a method described herein includes extracting or collecting material from the at least one abraded surface of at least one biological tissue. Such extraction or collection may include the use of at least one vacuum, aspirator, container, instrument, tool, device, chemical, laser, stylet, cannula, light source, scope (e.g., laprascope), needle, scalpel, shunt, stent, bag, film, filter, suction apparatus, tube, compressed gas, fluid (e.g., fluid stream or mist), magnifying apparatus, imaging device, computing device, or system.

In at least one embodiment, at least one of the needle, scalpel, or other tools or instruments utilized in extracting or collecting material from the at least one cell, tissue, or subject, includes one or more frozen particles (e.g., frozen hydrogen oxide, or other agents as described herein). Thus, the one or more frozen particles are fashioned or molded for use as microneedles or other instruments (e.g., scapels, blades, tools, etc.). In at least one embodiment, the one or more frozen particles are utilized prior to, during, or subsequent to surgery.

In at least one embodiment, the extracted or collected material includes at least one organic or inorganic material. In at least one embodiment, the material includes one or more cells from the at least one abraded surface of at least one biological tissue. In at least one embodiment, the at least one material includes at least part of one or more granuloma, eschar, callus, atheromatous plaque, abscess, pustule, scaling (e.g., psoriasis or eczema), infected tissue, microorganism accumulation, blood clot, blood vessel obstruction, duct obstruction, bowel obstruction, necrotic tissue, stratum corneum, hair follicle, nevus, wrinkle, keloid, biofilm, calculus, plaque, tartar, dandruff, keratin, collagen, dust, dirt, metal, glass, hair or fur, cellular secretion, microorganism, blood cell, particulate matter, or connective tissue.

In at least one embodiment, the at least one biological tissue is located in at least one of in situ, in vitro, in vivo, in utero, in planta, in silico, or ex vivo. In at least one embodiment, the at least one biological tissue is located in vivo. In at least one embodiment, the at least one biological tissue is located in at least one tissue or organ related to transplantation. In at least one embodiment, transplantation includes extraction or implantation of the at least one tissue or organ. In at least one embodiment, the at least one tissue or organ related to transplantation is extracted from at least one first biological source or subject and implanted into at least one second biological source or subject. In at least one embodiment, the at least one tissue or organ related to transplantation is cultured prior to implantation in a subject. In at least one embodiment, the tissue or organ related to transplantation is an artificial tissue or organ (e.g. a bladder, heart, kidney, liver, pancreas, skin, eye, lung, nerve, blood vessel, and others). In at least one embodiment, the tissue or organ related to transplantation involves at least two sources (i.e. multiple species, partially artificial or synthetic, multiple biological cells or tissues including stem cells). In at least one embodiment, the at least one tissue or organ related to transplantation includes at least one donor or recipient tissue or organ. In at least one embodiment, the at least one donor includes at least one cadaver. In at least one embodiment, the at least one biological tissue is ingested by at least one subject.

In at least one embodiment, the at least one tissue or organ related to transplantation includes one or more cells. The one or more cells may include endogenous or exogenous cells relative to a particular subject. In at least one embodiment, the at least one tissue or organ related to transplantation relates to one or more stem cells (e.g., hematopoietic stem cells, adipocyte stem cells, neuronal stem cells, embryonic stem cells, hepatic stem cells, dermal stem cells, pancreatic stem cells, stem cells related to bone, stem cells related to muscle, or others). In at least one embodiment, the at least one tissue or organ related to transplantation includes one or more of skin, scalp, hair, nail, nail bed, teeth, eye, cornea, ear, ovary, oviduct, tongue, tonsil, adenoid, liver, bone, pancreas, stomach, blood vessel, blood, lymph, heart, heart valve, lung, brain, breast, kidney, bladder, urethra, ureter, gall bladder, uterus, prostate, testes, vas deferens, fallopian tubes, large intestine, small intestine, esophagus, oral cavity, nasal cavity, otic cavity, tendon, vein (e.g., femoral or saphenous vein), artery, capillary, connective tissue, muscle tissue, or adipose tissue.

In at least one embodiment, the at least one biological tissue includes at least one cell mass. In at least one embodiment, the at least one cell mass includes at least one of a scar, pore, pit, eschar, granuloma, keloid, artheromatous plaque, abscess, pustule, scaling (e.g., psoriasis or eczema), infected tissue, hair follicle, necrotic tissue, stratum corneum, wrinkle, wound, tumor, skin structure, nevus, cyst, lesion, callus, neoplastic tissue, gangrenous tissue, or cellular deposit. In at least one embodiment, the at least one cell mass includes at least one benign or malignant tumor. In at least one embodiment, the at least one benign or malignant tumor relates to one or more of a melanoma, lymphoma, leukemia, sarcoma, blastoma, or carcinoma.

In at least one embodiment, the at least one cell mass is related to at least one blood clot, microorganism accumulation, blood vessel obstruction, duct obstruction, bowel obstruction, infection, gangrene, connective tissue destruction, tissue or organ damage, injury, white blood cell accumulation, or cancer.

For embodiments described herein, those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, C++ or other code sequences can be compiled or implemented in high-level descriptor languages (e.g., a logic-synthesizable language, a hardware description language, a hardware design simulation, and/or other such similar mode(s) of expression). For example, some or all of the logical expression may be manifested as a Verilog-type hardware description or other circuitry model before physical implementation in hardware. Those skilled in the art will recognize how to obtain, configure, and optimize suitable transmission or computational elements, material supplies, actuators, or other structures in light of these teachings.

As indicated in FIGS. 7-9, at least one embodiment, a method 700 includes comparing 710 information regarding at least one aspect of administering at least one frozen particle therapeutic composition to at least one subject and information regarding at least one clinical outcome following receipt by the at least one subject of at least one frozen particle therapeutic composition; and providing output information optionally based on the comparison.

In at least one embodiment, the method includes determining at least one statistical correlation 720. In at least one embodiment, the method includes counting the occurrence of at least one clinical outcome 730. In at least one embodiment, the method includes determining at least one correlation before the administration of the at least one frozen particle therapeutic composition 735. In at least one embodiment, information regarding at least one aspect of administering at least one frozen particle therapeutic composition includes information regarding the amount of at least one frozen particle therapeutic composition or therapeutic agent administered to at least one biological tissue of a subject 740. In at least one embodiment, the information regarding at least one aspect of administering or delivering at least one frozen particle therapeutic composition includes information regarding at least one dimension of biological tissue penetration 750. In at least one embodiment, information regarding the at least one dimension of biological tissue penetration includes information regarding at least one of depth, width, or breadth of administration of at least one frozen particle therapeutic composition to at least one biological tissue of at least one subject 760.

In at least one embodiment, the information regarding at least one aspect of administering at least one frozen particle therapeutic composition includes information regarding two or more subjects with one or more common attributes 770. In at least one embodiment, the one or more common attributes include genetic attributes, mental attributes, or psychological attributes 780. In at least on embodiment, the one or more common attributes include genotype attributes or phenotype attributes 790.

In at least one embodiment, the one or more common attributes 797 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical history; lymph condition, or blood condition.

In at least one embodiment, the output information 810 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of an administered or delivered frozen particle composition. In at least one embodiment, the at least one aspect of cellular or tissue abrasion or ablation includes information regarding at least one cellular or tissue source 820. In at least one embodiment, the information regarding at least one tissue source includes information regarding at least one abnormal cellular or tissue source 830. In at least one embodiment, the information regarding at least one cellular or tissue source includes information regarding at least one type of cell or tissue 840. In at least one embodiment, the cellular or tissue source includes at least one cell or biological tissue described herein.

In at least one embodiment, the at least one frozen particle composition or therapeutic composition includes at least one of nitrogen, carbon dioxide, hydrogen oxide, helium, neon, xenon, krypton, chlorine, bromine, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 850.

In at least one embodiment, the at least one frozen particle composition or therapeutic composition includes at least one major dimension of approximately one decimeter or less, or approximately one centimeter or less, approximately one millimeter or less, approximately one micrometer or less, approximately one nanometer or less, or any value therebetween 860.

In at least one embodiment, the at least one frozen particle composition or therapeutic composition includes one or more reinforcement agents 870. In at least one embodiment, the at least one frozen particle composition or therapeutic composition includes one or more explosive materials 880. In at least one embodiment, the receipt by the at least one subject of at least one frozen particle composition or therapeutic composition is pursuant to at least one clinical trial 900.

In at least one embodiment, the method includes creating at least one inclusion criterion and at least one exclusion criterion for a clinical trial involving the at least one frozen particle composition or therapeutic composition 910. In at least one embodiment, the method further comprises suggesting the inclusion of one or more of the at least one subject in at least one clinical trial 920. In at least one embodiment, the method further comprises suggesting the exclusion of one or more of the at least one subject in at least one clinical trial 930. In certain instances, multiple subjects from multiple clinical trials are included. In at least one embodiment, the method further includes using one or more of the at least one comparison to predict at least one clinical outcome regarding at least one second subject 940. In at least one embodiment, the at least one second subject has not received the at least one frozen particle composition or therapeutic composition 950. In at least one embodiment, the at least one second subject is a plurality of people; and the method further comprises segregating subject identifiers associated with the plurality of people in reference to the predicted at least one clinical outcome 960. In at least one embodiment, the at least one second subject is a plurality of people; and the method further comprises determining the eligibility of the at least one second subject for the at least one clinical trial 970.

Figure 10:
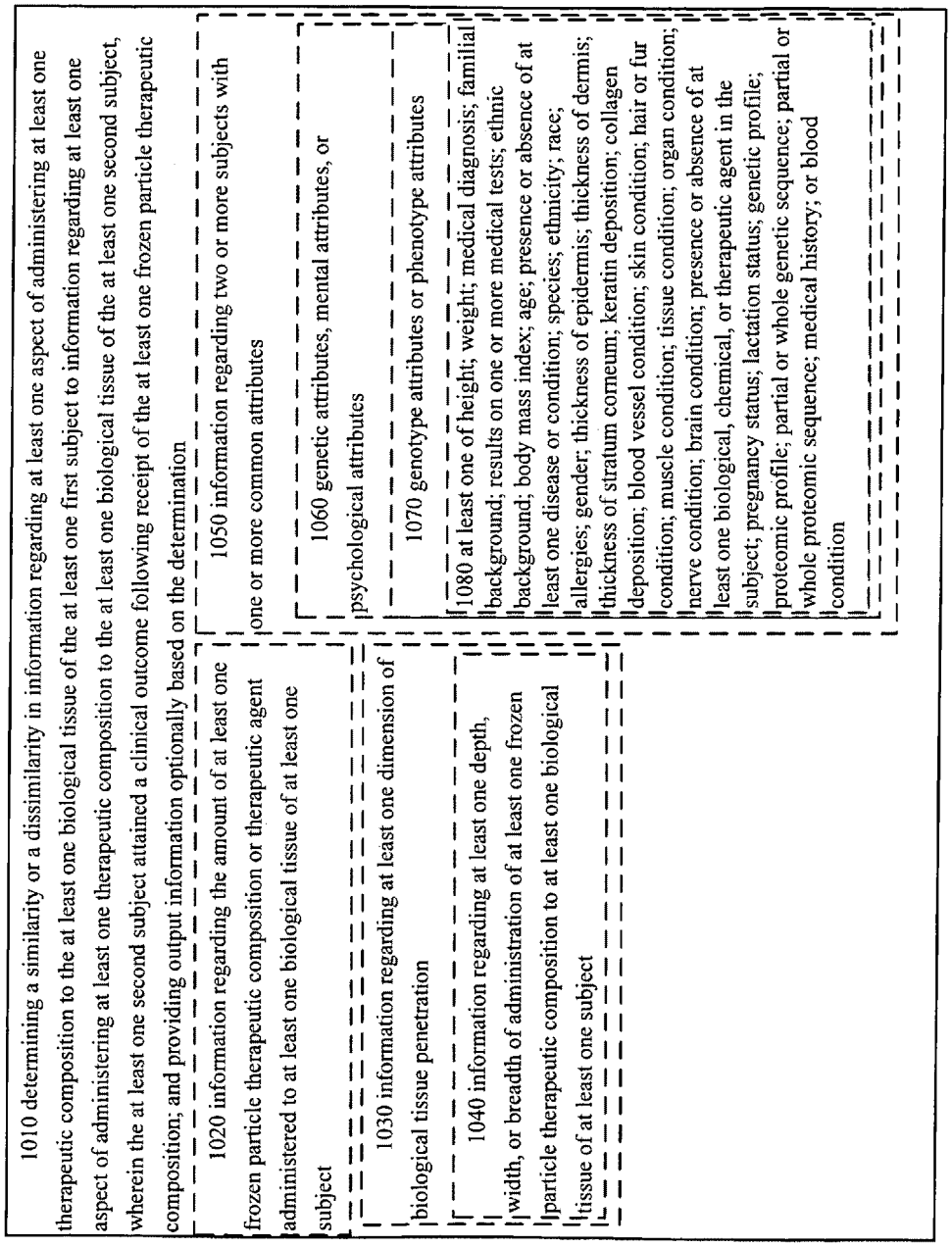
FIG. 10 illustrates a partial view of a method 1000 that includes generating at least one response.

As indicated in FIGS. 10-12, at least one aspect includes a method 1000 relating to predicting a clinical outcome of administering at least one frozen particle therapeutic composition to at least one biological tissue of at least one first subject includes determining a similarity or a dissimilarity in information regarding at least one aspect of administering at least one therapeutic composition to the at least one biological tissue of the at least one first subject to information regarding at least one aspect of administering at least one therapeutic composition to the at least one biological tissue of the at least one second subject, wherein the at least one second subject attained a clinical outcome following receipt of the at least one frozen particle therapeutic composition; and providing output information optionally based on the determination 1010.

In at least one embodiment, the information regarding the at least one aspect of administering at least one frozen particle therapeutic composition includes information 1020 regarding the amount of at least one frozen particle therapeutic composition or therapeutic agent delivered to at least one biological tissue of a subject. In at least one embodiment, the information regarding the at least one aspect of administering at least one frozen particle therapeutic composition includes information 1030 regarding at least one dimension of biological tissue penetration. In at least one embodiment, the information regarding the at least one dimension of biological tissue penetration includes information 1040 regarding at least one of depth, width, or breadth of delivery of at least one frozen particle therapeutic composition to at least one biological tissue of at least one subject; or information 1050 regarding two or more subjects with common attributes.

In at least one embodiment, the one or more common attributes include genetic attributes, mental attributes, or psychological attributes 1060. In at least on embodiment, the one or more common attributes include genotype attributes or phenotype attributes 1070.

In at least one embodiment, the one or more common attributes 1080 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; medical history; partial or whole proteomic sequence; lymph condition, or blood condition.

In at least one embodiment, the output information 1100 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of an administered or delivered frozen particle composition or therapeutic composition. In at least one embodiment, the at least one aspect of cellular or tissue abrasion or ablation includes information regarding at least one cellular or tissue source 1110. In at least one embodiment, the information regarding at least one tissue source includes information regarding at least one abnormal cellular or tissue source 1120. In at least one embodiment, the information regarding at least one cellular or tissue source includes information regarding at least one type of cell or tissue 1130. In at least one embodiment, the cellular or tissue source includes at least one cell or biological tissue described herein.

In at least one embodiment, the at least one frozen particle composition or therapeutic composition includes at least one of nitrogen, carbon dioxide, hydrogen oxide, helium, neon, xenon, krypton, chlorine, bromine, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 1140.

In at least one embodiment, the at least one frozen particle composition or therapeutic composition includes at least one major dimension of approximately one decimeter or less, or approximately one centimeter or less, approximately one millimeter or less, approximately one micrometer or less, approximately one nanometer or less, or any value therebetween 1150.

In at least one embodiment, the at least one frozen particle composition or therapeutic composition includes one or more reinforcement agents 1160. In at least one embodiment, the at least one frozen particle composition or therapeutic composition includes one or more explosive materials 1170.

In at least one embodiment, the receipt by the at least one subject of at least one frozen particle composition or therapeutic composition is pursuant to at least one clinical trial 1200. In at least one embodiment, the method further comprises determining at least one correlation before the administration or delivery of the at least one frozen particle composition or therapeutic composition to at least one subject 1210. The at least one subject includes, but is not limited to at least one subject described herein.

In at least one embodiment, the method includes creating at least one inclusion criterion and at least one exclusion criterion for a clinical trial involving the at least one frozen particle composition or therapeutic composition 1220. In at least one embodiment, the method further comprises suggesting the inclusion of one or more of the at least one subject in at least one clinical trial 1230. In at least one embodiment, the method further comprises suggesting the exclusion of one or more of the at least one subject in at least one clinical trial 1240. In certain instances, multiple subjects from multiple clinical trials are included. In at least one embodiment, the method further includes using one or more of the at least one comparison to predict at least one clinical outcome regarding at least one second subject 1250. In at least one embodiment, the at least one second subject has not received the at least one frozen particle composition or therapeutic composition 1260. In at least one embodiment, the method includes predicting at least one clinical outcome involving the at least one second subject, and the at least one second subject is a plurality of people; and the method further comprises segregating subject identifiers associated with the plurality of people in reference to the predicted at least one clinical outcome 1270.

In at least one embodiment, the at least one second subject is a plurality of people; and the method further comprises determining the eligibility of the at least one second subject for the at least one clinical trial 1280.

Figure 13:
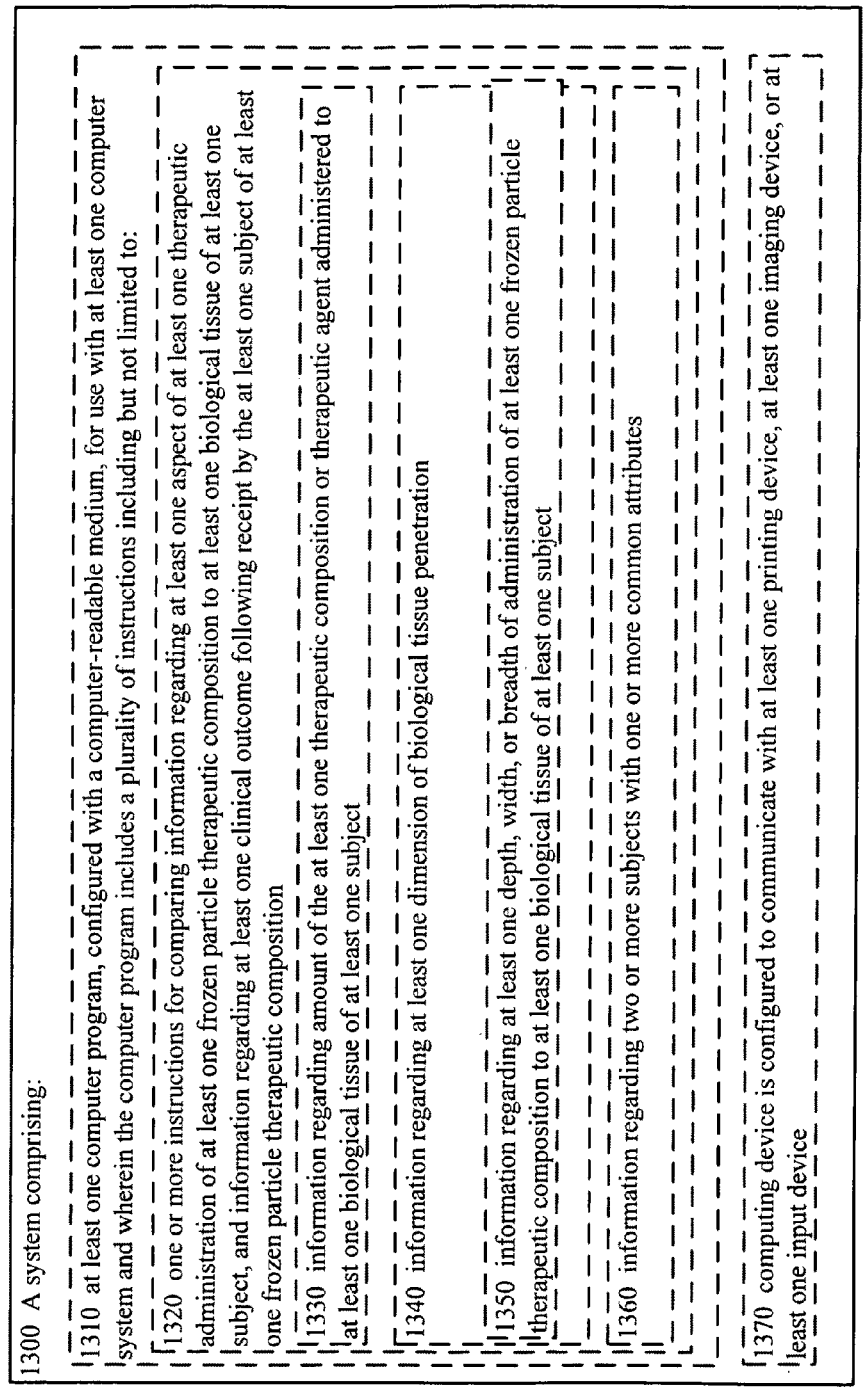
FIG. 13 illustrates a partial view of a system 1300 that includes a computer program for executing a computing process on a computing device.
Figure 14:
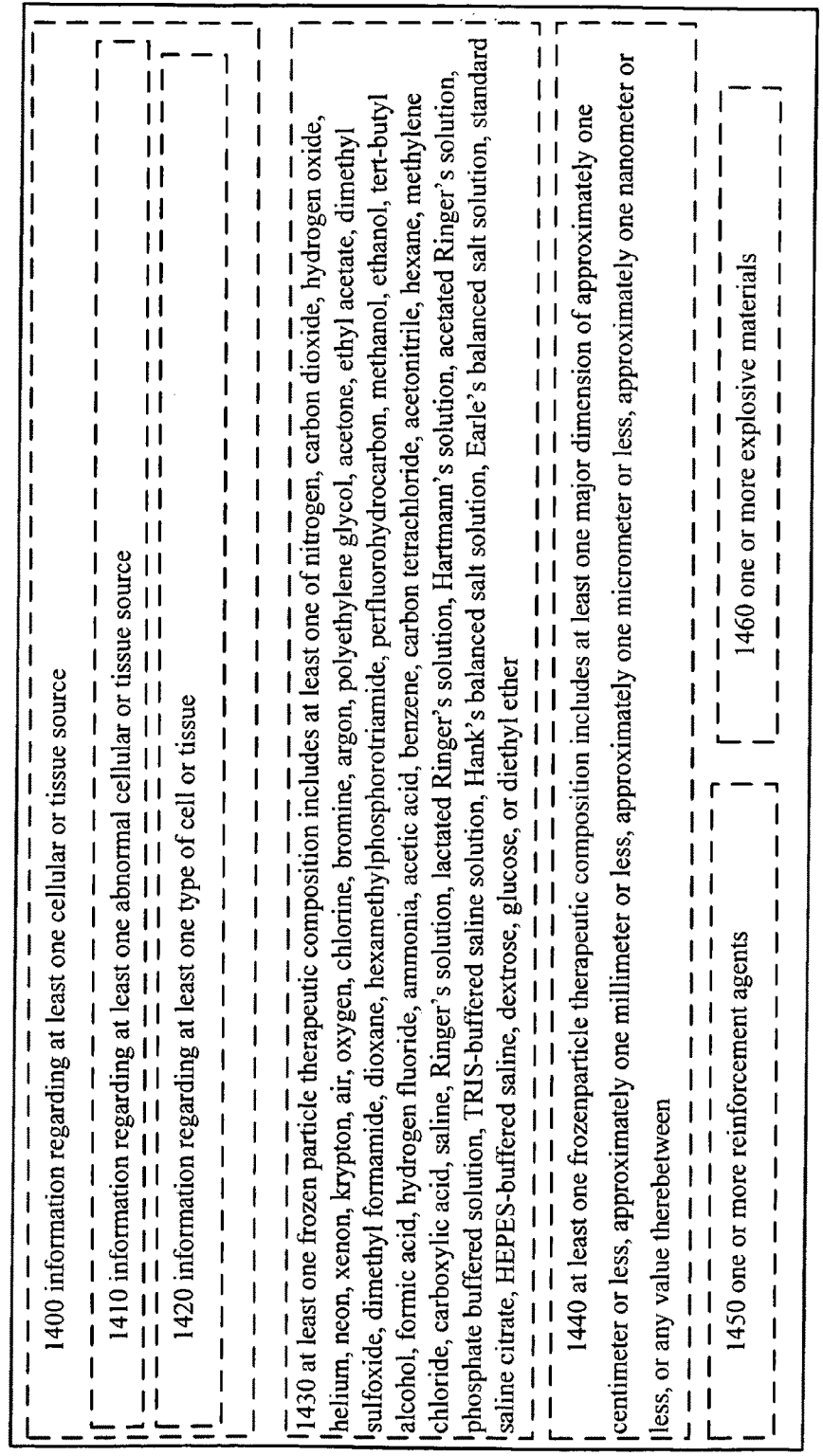
FIG. 14 illustrates a partial view and an embodiment of FIG. 13.

As shown in FIGS. 13-15, at least one embodiment includes a system 1300 including at least one computer program 1310, configured with a computer-readable medium, for use with at least one computer system and wherein the computer program includes a plurality of instructions including but not limited to one or more instructions 1320 for comparing information regarding at least one aspect of at least one therapeutic administration of at least one frozen particle composition or therapeutic composition to at least one subject. In at least one embodiment, information 1330 regarding amount of the at least one frozen particle composition, therapeutic composition, or therapeutic agent administered to at least one biological tissue of at least one subject. In at least one embodiment, information regarding at least one aspect of at least one therapeutic administration of at least one frozen particle composition or therapeutic composition includes information regarding at least one dimension of biological tissue penetration 1340. In at least one embodiment, information regarding at least one aspect of at least one therapeutic administration of at least one frozen particle composition or therapeutic composition includes information regarding at least one of depth, width, or breadth of administration of at least one frozen particle composition or therapeutic composition to at least one biological tissue of at least one subject 1350. In at least one embodiment, information regarding at least one aspect of at least one therapeutic administration includes information regarding two or more subjects with one or more common attributes 1360. In at least one embodiment, the computing device is configured to communicate with at least one imaging device. In at least one embodiment, the computing device is configured to communicate with at least one printing device. In at least one embodiment, the computing device is configured to communicate with at least one input device 1370.

In at least one embodiment, the information regarding at least one aspect of therapeutic administration of at least one therapeutic composition includes information regarding at least one cellular or tissue source 1400; information regarding at least one abnormal cellular or tissue source 1410; or information regarding at least one type of cell or tissue 1420. In at least one embodiment, at least one frozen particle composition or therapeutic composition includes at least one of nitrogen, carbon dioxide, hydrogen oxide, helium, neon, xenon, krypton, chlorine, bromine, oxygen, air or argon. In at least one embodiment, the at least one frozen particle composition or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 1430. In at least one embodiment, at least one frozen particle composition or therapeutic composition includes at least one major dimension of approximately one decimeter or less, approximately one centimeter or less, approximately one millimeter or less, approximately one micrometer or less, approximately one nanometer or less, or any value therebetween 1440. In at least one embodiment, the at least one frozen particle composition or therapeutic composition includes one or more reinforcement agents 1450 or one or more explosive materials 1460.

In at least one embodiment, the receipt by the at least one subject of at least one frozen particle composition or therapeutic composition is pursuant to at least one clinical trial 1500. In at least one embodiment, the system further comprises determining at least one correlation before the delivery or administration of the at least one frozen particle composition or therapeutic composition to at least one subject 1510.

In at least one embodiment, the method includes creating at least one inclusion criterion and at least one exclusion criterion for a clinical trial involving the at least one frozen particle composition or therapeutic composition 1520. In at least one embodiment, the instructions further comprise suggesting the inclusion of one or more of the at least one subject in at least one clinical trial 1530. In certain instances, multiple subjects from multiple clinical trials are included.

In at least one embodiment, the instructions include suggesting the exclusion of one or more of the at least one subject in at least one clinical trial 1540.

In at least one embodiment, a method includes using one or more of the at least one comparison to predict at least one clinical outcome regarding at least one second subject 1550. In at least one embodiment, the at least one second subject has not received the at least one frozen particle composition or therapeutic composition 1560. In at least one embodiment, the at least one second subject is a plurality of people; and further comprising segregating subject identifiers associated with the plurality of people in reference to the predicted at least one clinical outcome 1570.

In at least one embodiment, the using one or more of the at least one comparison, wherein the at least one second subject is a plurality of people; and further comprising determining the eligibility of the at least one second subject for the at least one clinical trial 1580.

Figure 16:
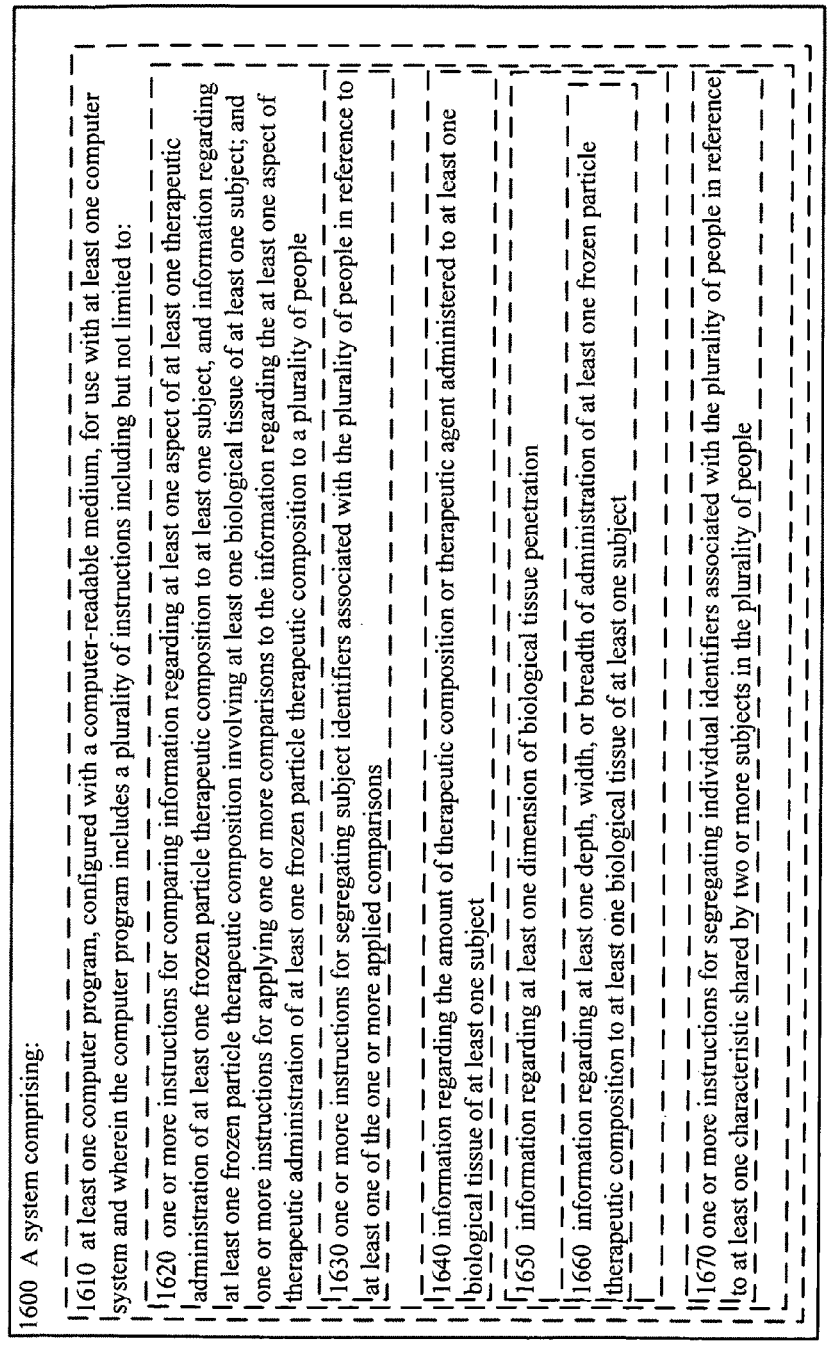
FIG. 16 illustrates a partial view of a system 1600 that includes a computer program for executing a computing process on a computing device.

As indicated in FIG. 16, at least one embodiment relates to a system 1600 including at least one computer program 1610 configured with a computer-readable medium, for use with at least one computer system and wherein the computer program includes a plurality of instructions including but not limited to one or more instructions 1620 for comparing information regarding at least one aspect of at least one therapeutic administration of at least one frozen particle therapeutic composition to at last one subject, and information regarding at least one frozen particle therapeutic composition involving at least one biological tissue of at least one subject; and one or more instructions for applying one or more comparisons to the information regarding the at least one aspect of therapeutic administration of at least one frozen particle therapeutic composition to a plurality of people. In at least one embodiment, the computer program includes one or more instructions 1630 for segregating subject identifiers associated with the plurality of people in reference to at least one of the one or more applied comparisons. In at least one embodiment, information regarding at least one aspect of at least one therapeutic administration includes information 1640 regarding the amount of at least one frozen particle composition, therapeutic composition or therapeutic agent administered to at least one biological tissue of at least one subject; information 1650 regarding at least one dimension of biological tissue penetration; information 1660 regarding at least one of depth, width, or breadth of administration of at least one frozen particle therapeutic composition to at least one biological tissue of at least one subject. In at least one embodiment, the computer program includes one or more instructions 1670 for segregating individual identifiers associated with the plurality of people in reference to at least one characteristic shared by two or more subjects in the plurality of people.

Figure 17:
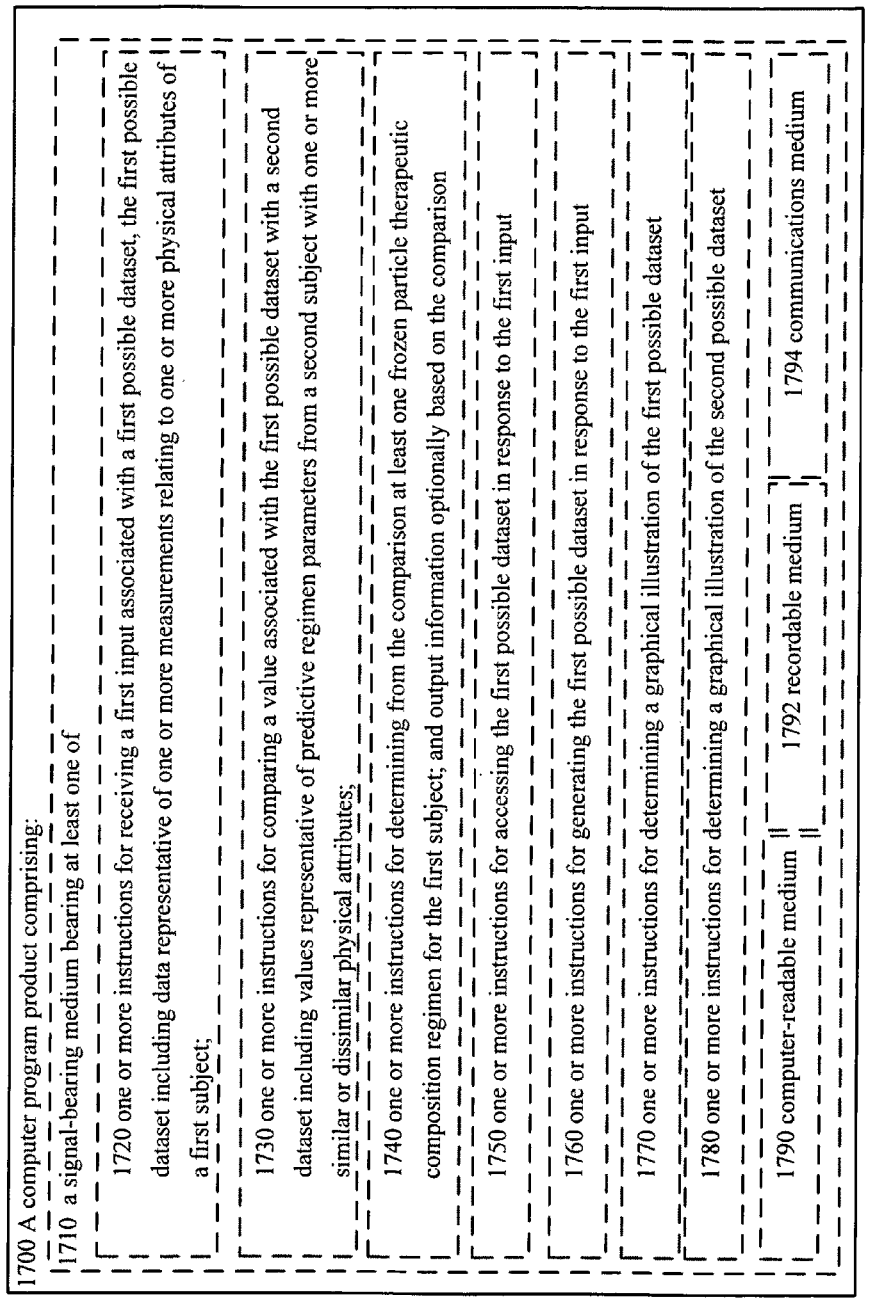
FIG. 17 illustrates a partial view of a computer program product 1700 for executing a computing process on a computing device.

As shown in FIG. 17, at least one embodiment relates to a computer program product 1700 that includes a signal bearing medium 1710 bearing at least one of one or more instructions 1720 for receiving a first input associated with a first possible dataset, the first possible dataset including data representative of one or more measurements relating to one or more physical attributes of a first subject; one or more instructions 1730 for comparing a value associated with the first possible dataset with a second dataset including values representative of predictive regimen parameters from a second subject with one or more similar or dissimilar physical attributes; one or more instructions 1740 for determining from the comparison at least one frozen particle therapeutic composition regimen for the first subject and output information; one or more instructions 1750 for accessing the first possible dataset in response to the first input; one or more instructions 1760 for generating the first possible dataset in response to the first input; one or more instructions 1770 for determining a graphical illustration of the first possible dataset; one or more instructions 1780 for determining a graphical illustration of the second possible dataset; and at least one generated output optionally based on the determination.

In at least one embodiment, the computer program product includes a signal bearing medium that includes a computer-readable medium 1790. In at least one embodiment, the signal bearing medium of the computer program product includes a recordable medium 1792. In at least one embodiment, the computer program product includes a signal bearing medium that includes a communications medium 1794.

Figure 18:
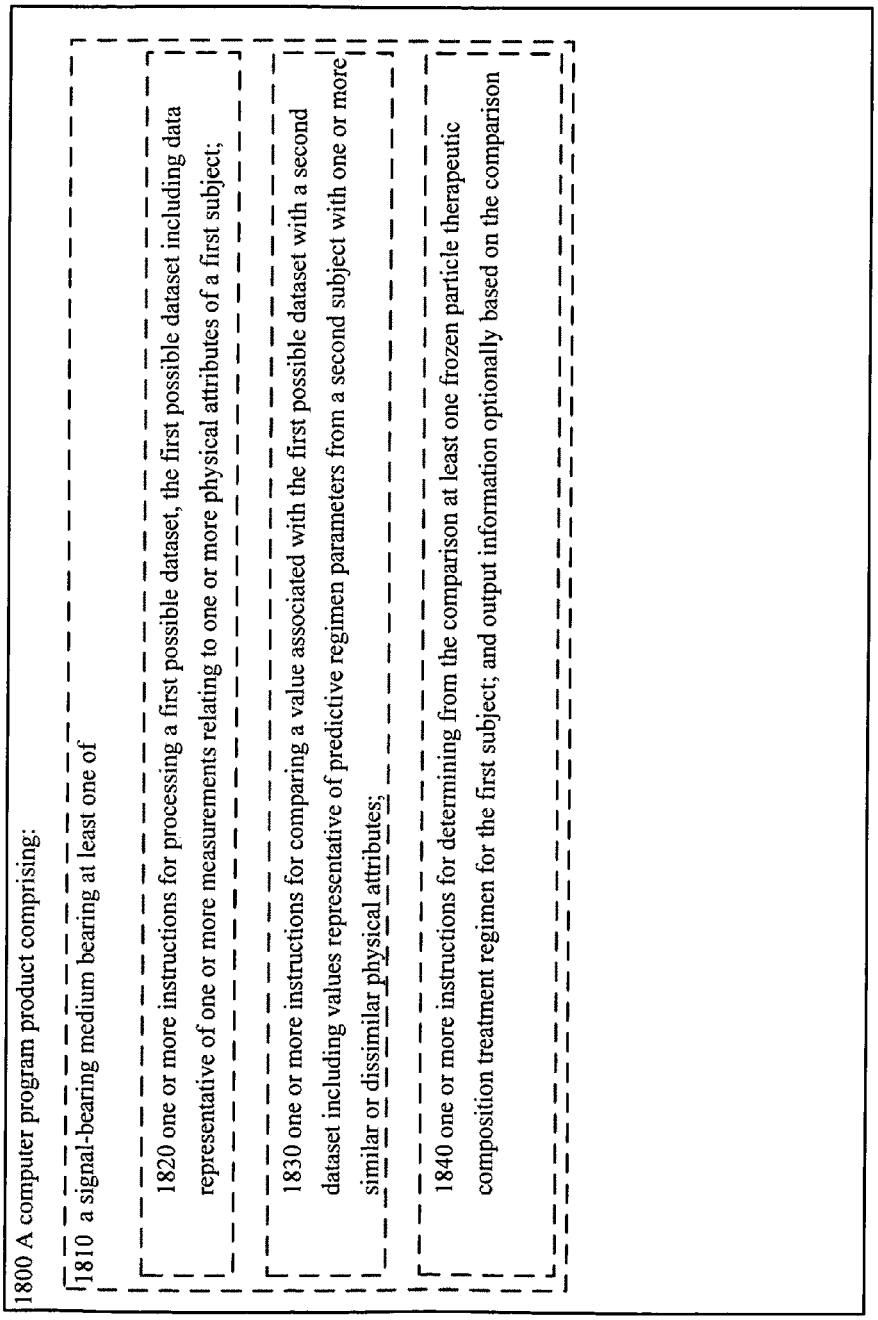
FIG. 18 illustrates a partial view of a computer program product 1800 for executing a computing process on a computing device.

As indicated in FIG. 18, at least one embodiment relates to a computer program product 1800 that includes a signal bearing medium 1810 bearing at least one of one or more instructions 1820 for processing a first possible dataset, the first possible dataset including data representative of one or more measurements relating to one or more physical attributes of a first subject; one or more instructions 1830 for comparing a value associated with the first possible dataset with a second dataset including values representative of predictive regimen parameters from a second subject with one or more similar or dissimilar physical attributes; one or more instructions 1840 for determining from the comparison at least one frozen particle composition or therapeutic composition treatment regimen for the first subject, and output information.

Figure 19:
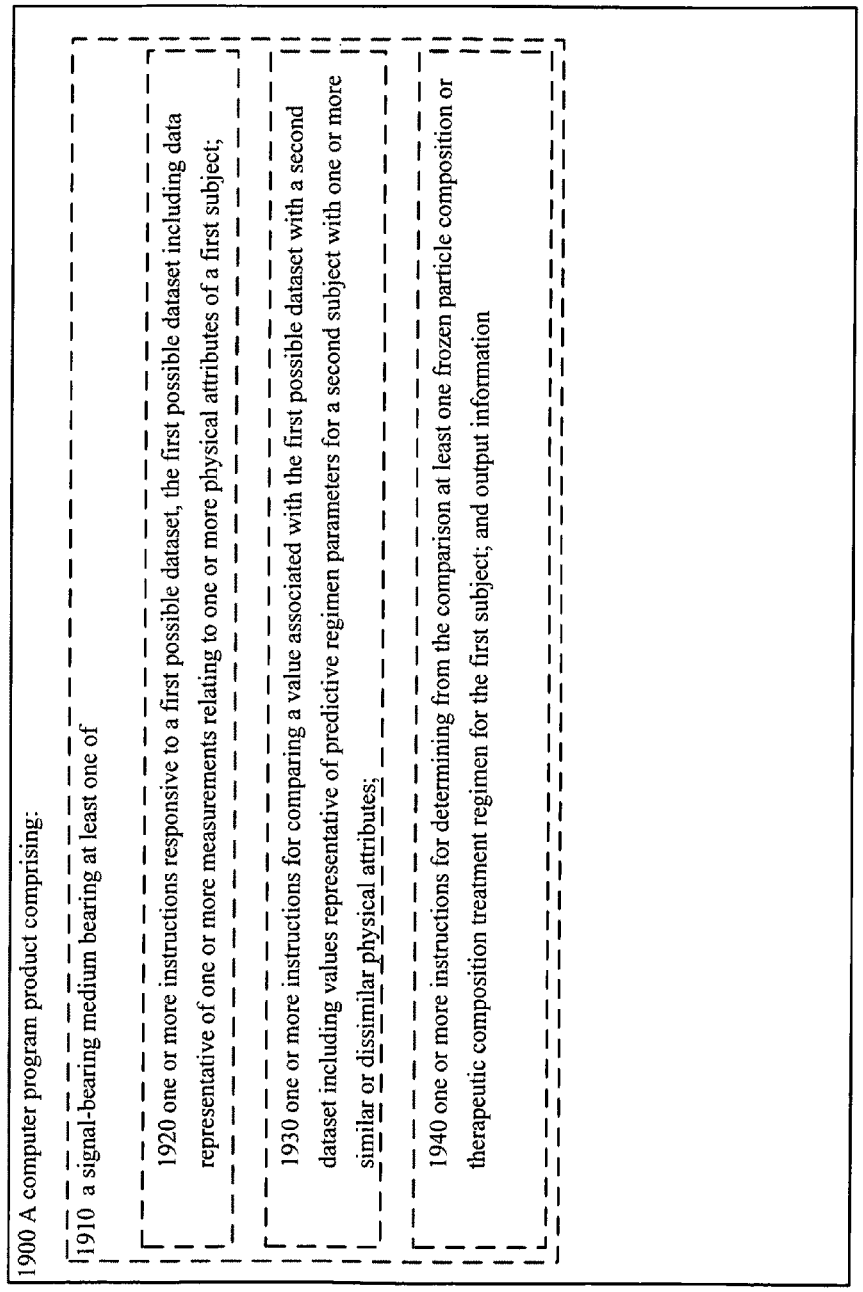
FIG. 19 illustrates a partial view of a computer program product 1900 for executing a computing process on a computing device.

As indicated in FIG. 19, at least one embodiment relates to a computer program product 1900 that includes a signal bearing medium 1910 bearing at least one of one or more instructions 1920 responsive to a first possible dataset, the first possible dataset including data representative of one or more measurements relating to one or more physical attributes of a first subject; one or more instructions 1930 for comparing a value associated with the first possible dataset with a second dataset including values representative of predictive regimen parameters for a second subject with one or more similar or dissimilar physical attributes; one or more instructions 1940 for determining from the comparison at least one frozen particle composition or therapeutic composition treatment regimen for the first subject; and output information optionally based on the determination.

As shown in FIG. 20, at least one embodiment relates to a computer program product 2000 that includes a signal bearing medium 2010 bearing at least one of one or more instructions 2020 for receiving a first input associated with a first possible dataset, the first possible dataset including data representative of one or more measurements relating to one or more physical attributes of a subject; one or more instructions 2030 for comparing a value associated with the first possible dataset with a second dataset including values representative of parameters relating to one or more expected biological changes following administration of one or more frozen particle compositions or therapeutic compositions; one or more instructions 2040 for determining from the comparison at least one biological change following administration of one or more frozen particle compositions or therapeutic compositions to the subject; at least one generated output optionally based on the determination.

In at least one embodiment, the computer program product includes one or more instructions 2050 for accessing the first possible dataset in response to the first input. In at least one embodiment, the computer program product includes one or more instructions 2060 for generating the first possible dataset in response to the first input.

In at least one embodiment, the computer program product includes one or more instructions 2070 for determining a graphical illustration of the first possible dataset. In at least one embodiment, the computer program product includes one or more instructions 2080 for determining a graphical illustration of the second possible dataset. In at least one embodiment, the signal bearing medium includes a computer-readable medium 2090. In at least one embodiment, the signal bearing medium includes a recordable medium 2092. In at least one embodiment, the signal bearing medium includes a communications medium 2094.

As indicated in FIG. 21, at least one embodiment a computer program product 2100 includes a signal bearing medium 2110 bearing at least one of one or more instructions 2120 for processing a first input associated with a first possible dataset, the first possible dataset including data representative of one or more measurements relating to one or more physical attributes of a subject; one or more instructions 2130 for comparing a value associated with the first possible dataset with a second dataset including values representative of parameters relating to one or more expected biological changes following administration of one or more frozen particle compositions or therapeutic compositions; one or more instructions 2140 for determining from the comparison at least one biological change following administration of one or more frozen particle compositions or therapeutic compositions to the subject; at least one generated output optionally based on the determination.

Figure 22:
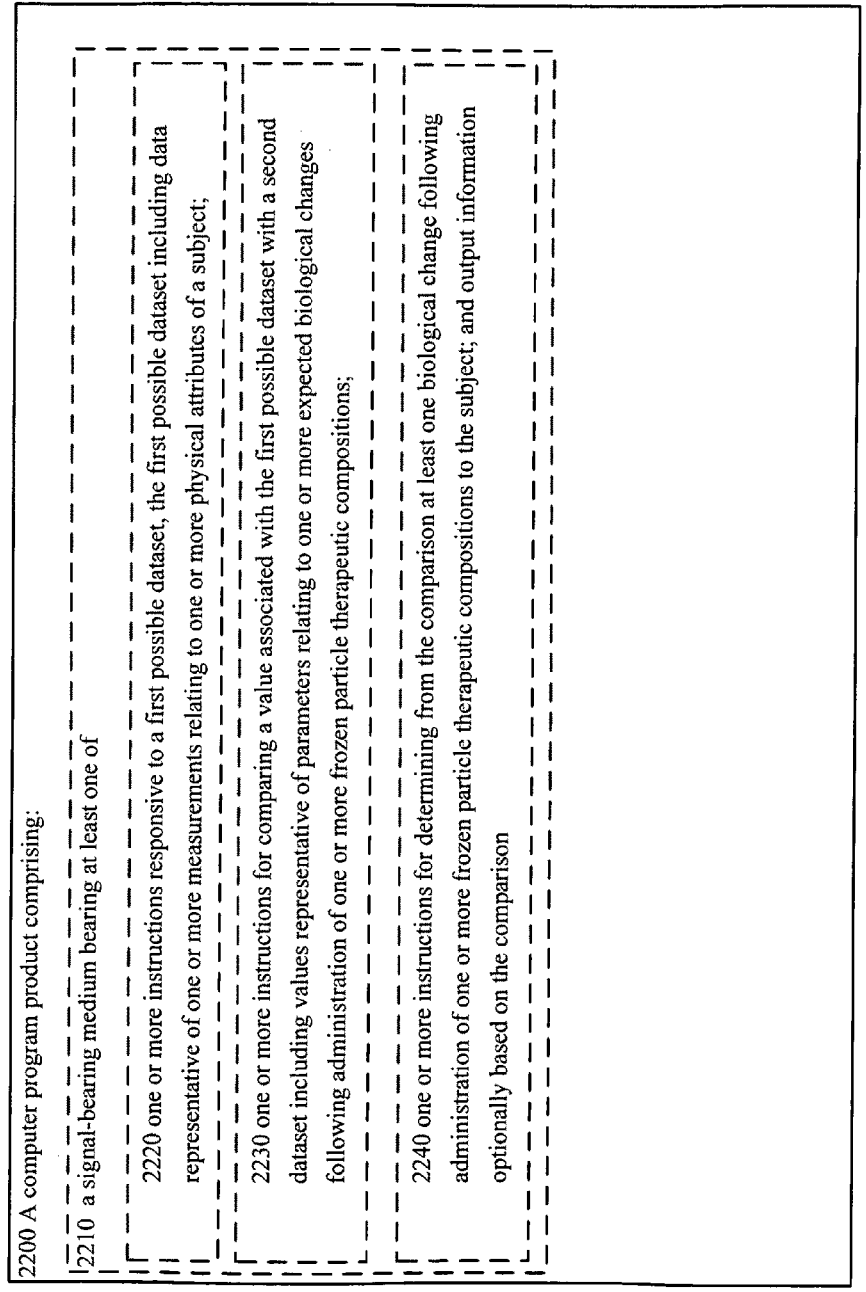
FIG. 22 illustrates a partial view of a computer program product 2200 for executing a computing process on a computing device.

As shown in FIG. 22, at least one embodiment relates to a computer program product 2200 includes a signal bearing medium 2210 bearing at least one of one or more instructions 2220 responsive to a first possible dataset, the first possible dataset including data representative of one or more measurements relating to one or more physical attributes of a subject; one or more instructions 2230 for comparing a value associated with the first possible dataset with a second dataset including values representative of parameters relating to one or more expected biological changes following administration of one or more frozen particle compositions or therapeutic compositions; one or more instructions 2240 for determining from the comparison at least one biological change following administration of one or more frozen particle compositions or therapeutic compositions to the subject; and output information optionally based on the determination.

As indicated in FIGS. 23-25, at least one embodiment, a method 2300 includes comparing 2310 information regarding at least one aspect of cellular or tissue abrasion or ablation of at least one biological tissue of at least one subject and information regarding at least one clinical outcome following receipt by the at least one subject of at least one frozen particle composition or therapeutic composition; and providing output information optionally based on the determination. In at least one embodiment, the method includes determining at least one statistical correlation 2320. In at least one embodiment, the method includes counting the occurrence of at least one clinical outcome 2330. In at least one embodiment, the information regarding at least one aspect of cellular or tissue abrasion or ablation includes information regarding quantity of cells or tissue removed or destroyed 2340. In at least one embodiment, the information regarding at least one aspect of cellular or tissue abrasion or ablation includes information regarding at least one dimension of cellular or tissue removal or destruction, or removal or destruction of other materials, such as plaque, extracellular matrix, collagen, elastin, protein, or other materials 2350. In at least one embodiment, information regarding the at least one dimension of cellular removal or destruction includes information regarding at least one of depth, width, or breadth of cellular removal or destruction 2360.

In at least one embodiment, the information regarding at least one aspect of cellular or tissue abrasion or ablation includes information regarding two or more subjects with one or more common attributes 2370. In at least one embodiment, the one or more common attributes include genetic attributes, mental attributes, or psychological attributes 2380. In at least on embodiment, the one or more common attributes include genotype attributes or phenotype attributes 2390.

In at least one embodiment, the one or more common attributes 2397 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; medical history; partial or whole proteomic sequence; lymph condition, or blood condition.

In at least one embodiment, the output information 2410 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of a delivered or administered frozen particle composition. In at least one embodiment, the at least one aspect of cellular or tissue abrasion or ablation includes information regarding at least one cellular or tissue source 2420. In at least one embodiment, the information regarding at least one tissue source includes information regarding at least one abnormal cellular or tissue source 2430. In at least one embodiment, the information regarding at least one cellular or tissue source includes information regarding at least one type of cell or tissue 2440. In at least one embodiment, the cellular or tissue source includes at least one cell or biological tissue described herein.

In at least one embodiment, the at least one frozen particle composition or therapeutic composition includes at least one of nitrogen, carbon dioxide, hydrogen oxide, helium, neon, xenon, krypton, chlorine, bromine, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 2450.

In at least one embodiment, the at least one frozen particle composition includes at least one major dimension of approximately one decimeter or less, or approximately one centimeter or less, approximately one millimeter or less, approximately one micrometer or less, approximately one nanometer or less, or any value therebetween 2460.

In at least one embodiment, the at least one frozen particle composition includes one or more reinforcement agents 2470. In at least one embodiment, the at least one frozen particle composition includes one or more explosive materials 2480. In at least one embodiment, the receipt by the at least one subject of at least one frozen particle composition is pursuant to at least one clinical trial 2500. In at least one embodiment, the method further comprises determining at least one correlation 2510 before the delivery or administration of the at least one frozen particle composition to at least one subject. The at least one subject includes, but is not limited to at least one subject described herein.

In at least one embodiment, the method includes creating at least one inclusion criterion and at least one exclusion criterion for a clinical trial involving the at least one frozen particle composition or therapeutic composition 2515. In at least one embodiment, the method further comprises suggesting the inclusion of one or more of the at least one subject in at least one clinical trial 2520. In at least one embodiment, the method further comprises suggesting the exclusion of one or more of the at least one subject in at least one clinical trial 2530. In certain instances, multiple subjects from multiple clinical trials are included. In at least one embodiment, the method further includes using one or more of the at least one correlation to predict at least one clinical outcome regarding at least one second subject 2540. In at least one embodiment, the at least one second subject has not received the at least one frozen particle composition or therapeutic composition 2550. In at least one embodiment, the method further comprises predicting at least one clinical outcome involving the at least one second subject, wherein the at least one second subject is a plurality of people; and segregating subject identifiers associated with the plurality of people in reference to the predicted at least one clinical outcome 2560. In at least one embodiment, the at least one second subject is a plurality of people; and the method further comprises determining the eligibility of the at least one second subject for the at least one clinical trial 2570.

Figure 26:
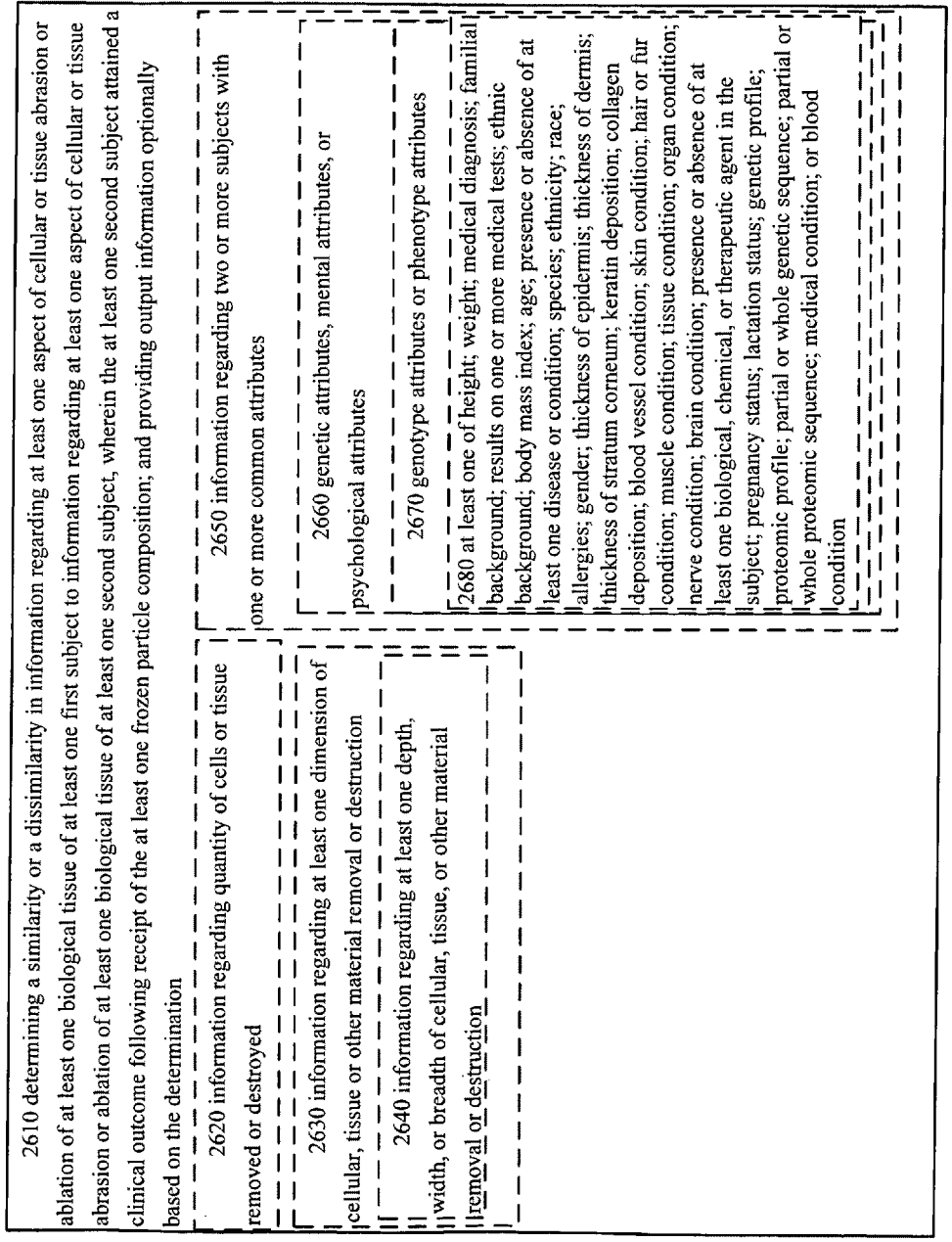
FIG. 26 illustrates a partial view of a method 2600 that includes generating at least one response.
Figure 28:
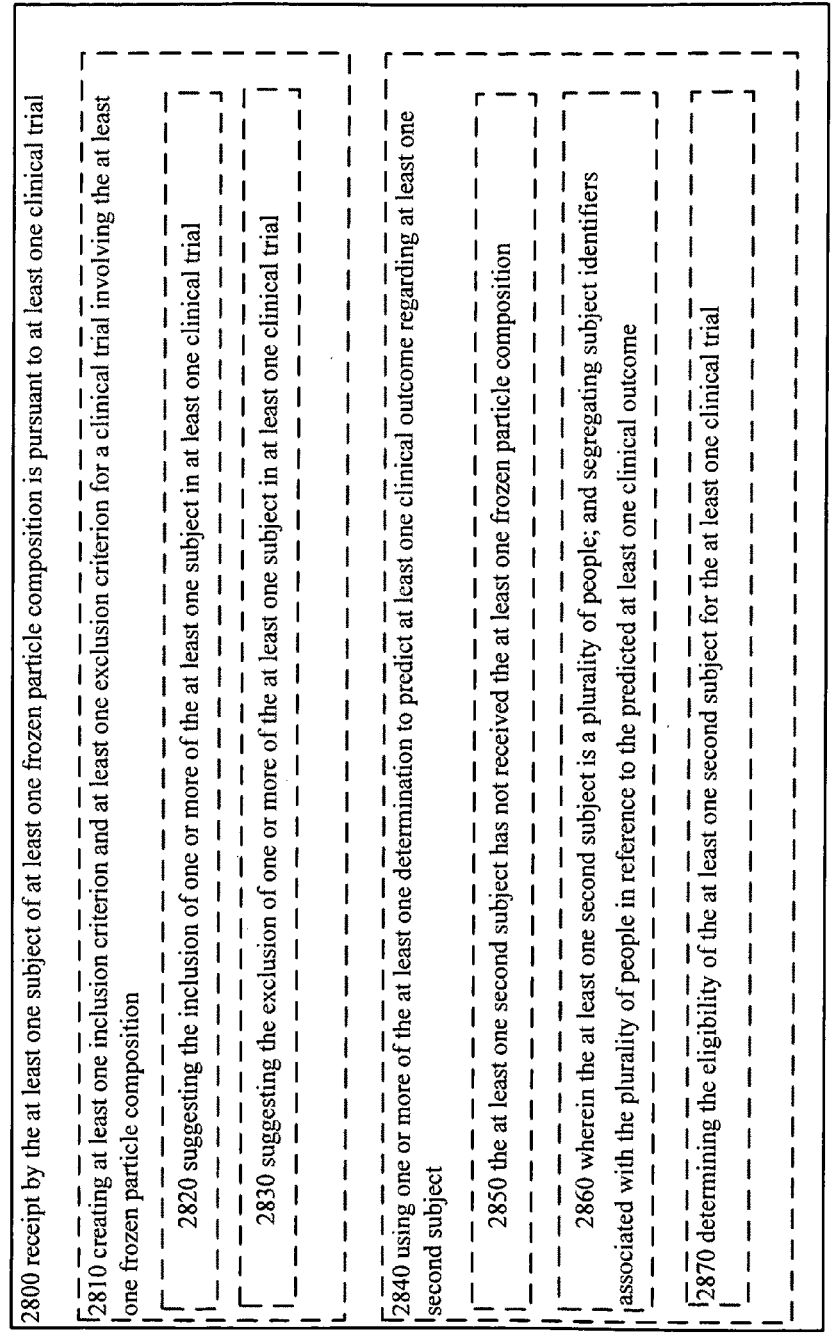
FIG. 28 illustrates a partial view and an embodiment of FIG. 26.

As indicated in FIGS. 26-28, at least one embodiment relates to a method 2600 of predicting a clinical outcome of at least one frozen particle composition treatment for at least one first subject includes determining 2610 a similarity or a dissimilarity in information regarding at least one aspect of cellular or tissue abrasion or ablation of at least one biological tissue of at least one first subject to information regarding at least one aspect of cellular or tissue abrasion or ablation of at least one biological tissue of at least one second subject, wherein the at least one second subject attained a clinical outcome following receipt of the at least one frozen particle composition or therapeutic composition; and providing output information optionally based on the determination.

In at least one embodiment, the information regarding at least one aspect of cellular or tissue abrasion or ablation includes information regarding the quantity of cells or tissue removed or destroyed 2620. In at least one embodiment, the information regarding at least one aspect of cellular or tissue abrasion or ablation includes information regarding at least one dimension of cellular, tissue, or other material removal or destruction 2630. In at least one embodiment, the at least one dimension of cellular removal or destruction includes information regarding at least one of depth, width, or breadth of cellular removal or destruction 2640. In at least one embodiment, the information regarding at least one aspect of cellular or tissue abrasion or ablation includes information regarding two or more subjects with one or more common attributes 2650.

In at least one embodiment, the one or more common attributes include but are not limited to genetic attributes, mental attributes, or psychological attributes 2660. In at least one embodiment, the one or more common attributes include genotype attributes or phenotype attributes 2670.

In at least one embodiment, the one or more common attributes include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; medical history; genetic profile; proteomic profile; partial or whole genetic sequence; partial or whole proteomic sequence; lymph condition, medical history, or blood condition 2680.

In at least one embodiment, the output information includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of a delivered or administered frozen particle composition 2700.

In at least one embodiment, the information regarding at least one aspect of cellular or tissue abrasion or ablation includes information regarding at least one cellular or tissue source 2710. In at least one embodiment, the cellular or tissue source includes but is not limited to at least one biological tissue or cell described herein. In at least one embodiment, the information regarding at least one tissue source includes information regarding at least one abnormal cellular or tissue source 2720. In at least one embodiment, the information regarding at least one cellular or tissue source includes information regarding at least one type of cell or tissue 2730. In at least one embodiment, the information regarding at least one aspect of cellular or tissue abrasion or ablation includes information regarding at least one type of cell or tissue.

In at least one embodiment, the at least one frozen particle composition or therapeutic composition includes at least one of nitrogen, carbon dioxide, hydrogen oxide, helium, neon, xenon, krypton, chlorine, bromine, oxygen, air or argon. In at least one embodiment, the at least one frozen particle composition or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 2740.

In at least one embodiment, the at least one frozen particle composition or therapeutic composition includes at least one major dimension of approximately one decimeter or less, or approximately one centimeter or less, or approximately one millimeter or less, or approximately one micrometer or less, or approximately one nanometer or less, or any value therebetween 2750.

In at least one embodiment, the at least one frozen particle composition or therapeutic composition includes one or more reinforcement agents 2760. In at least one embodiment, the at least one frozen particle composition or therapeutic composition includes one or more explosive materials 2770.

In at least one embodiment, the receipt by the at least one subject of at least one frozen particle composition or therapeutic composition is pursuant to at least one clinical trial 2800. In at least one embodiment, the method includes creating at least one inclusion criterion and at least one exclusion criterion for a clinical trial involving the at least one frozen particle composition or therapeutic composition 2810. In at least one embodiment, the method further comprises suggesting the inclusion of one or more of the at least one subject in at least one clinical trial 2820. In certain instances, multiple subjects from multiple clinical trials are included. In at least one embodiment, the method includes suggesting the exclusion of one or more of the at least one subject in at least one clinical trial 2830.

In at least one embodiment, a method includes using one or more of the at least one determination to predict at least one clinical outcome regarding at least one second subject 2840. In at least one embodiment, the at least one second subject has not received the at least one frozen particle composition or therapeutic composition 2850. In at least one embodiment, the at least one second subject is a plurality of people; and the method further comprises segregating subject identifiers associated with the plurality of people in reference to the predicted at least one clinical outcome 2860.

In at least one embodiment, the using one or more of the at least one comparison, wherein the at least one second subject is a plurality of people; and the method further comprises determining the eligibility of the at least one second subject for the at least one clinical trial 2870.

Figure 29:
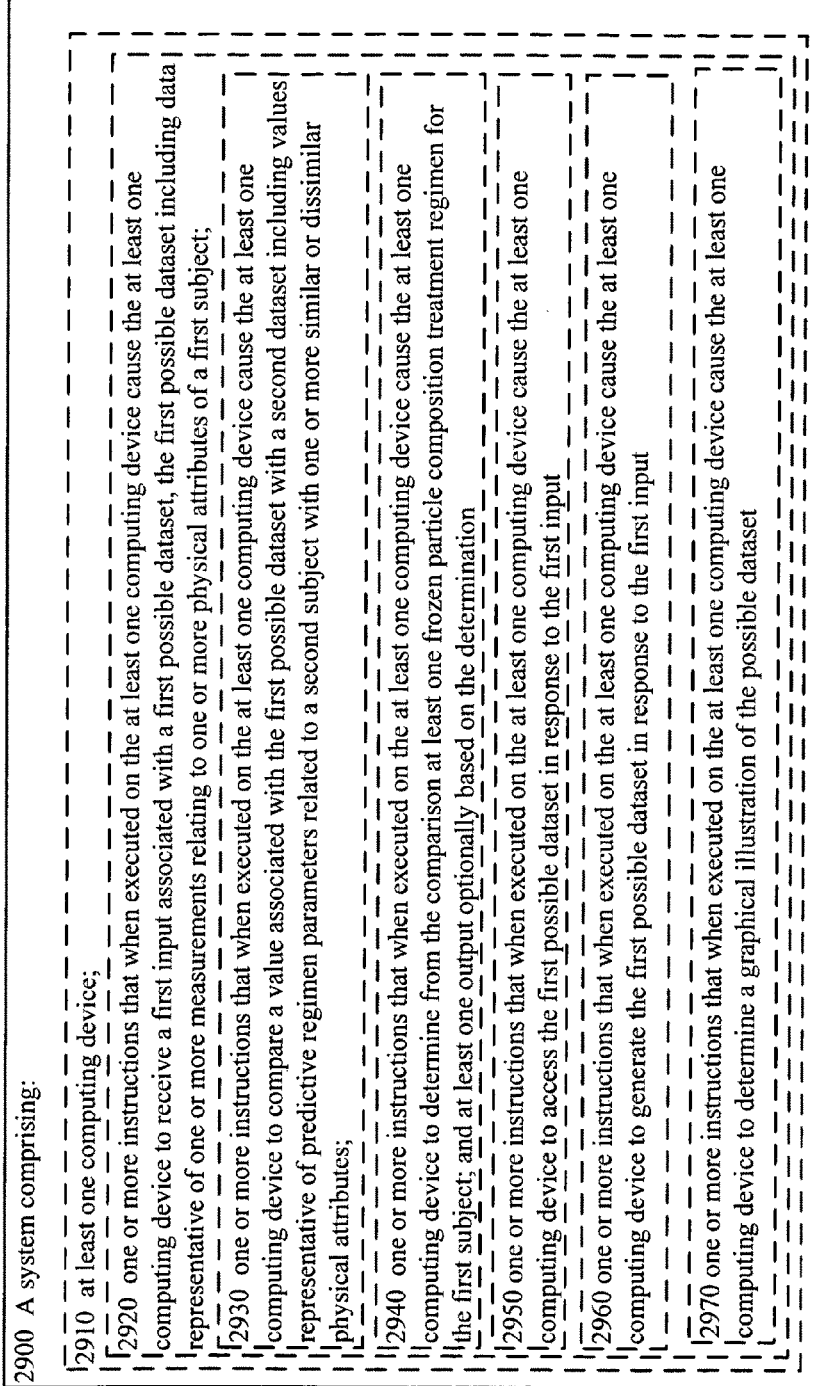
FIG. 29 illustrates a partial view of a system 2900 that includes a computer program for executing a computing process on a computing device.

As indicated in FIGS. 29-30, at least one aspect relates to a system 2900 that includes at least one computing device 2910; one or more instructions 2920 that when executed on the at least one computing device cause the at least one computing device to receive a first input associated with a first possible dataset, the first possible dataset including data representative of one or more measurements relating to one or more physical attributes of a first subject; one or more instructions 2930 that when executed on the at least one computing device cause the at least one computing device to compare a value associated with the first possible dataset with a second dataset including values representative of predictive regimen parameters related to a second subject with one or more similar or dissimilar physical attributes; one or more instructions 2940 that when executed on the at least one computing device cause the at least one computing device to determine from the comparison at least one frozen particle composition treatment regimen for the first subject; and at least one generated output optionally based on the determination; one or more instructions 2950 that when executed on the at least one computing device cause the at least one computing device to access the first possible dataset in response to the first input; one or more instructions 2960 that when executed on the at least one computing device cause the at least one computing device to generate the first possible dataset in response to the first input; one or more instructions 2970 that when executed on the at least one computing device cause the at least one computing device to determine a graphical illustration of the possible dataset; or one or more instructions 3000 that when executed on the at least one computing device cause the at least one computing device to determine a graphical illustration of the second possible dataset. In at least one embodiment, the treatment regimen includes at least one of cellular or tissue removal, cellular or tissue ablation, debridement, delivery of at least one therapeutic agent, cleaning one or more wounds, removing material from at least one biological tissue, or removing material from at least one blood vessel 3005. In at least one nitrogen, carbon dioxide, hydrogen oxide, helium, neon, xenon, krypton, chlorine, bromine, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 3008.

In at least one embodiment, the at least one computing device includes one or more desktop computer, workstation computer, computing system including a cluster of processors, a networked computer, a tablet personal computer, a laptop computer, a mobile device, a mobile telephone, or a personal digital assistant computer 3010. In at least one embodiment, the at least one computing device is configured to communicate with a database to access the first possible dataset 3020. In at least one embodiment, the at least one computing device is configured to communicate with a frozen particle composition selecting apparatus, a frozen particle composition generating apparatus, or both 3030.

Figure 31:
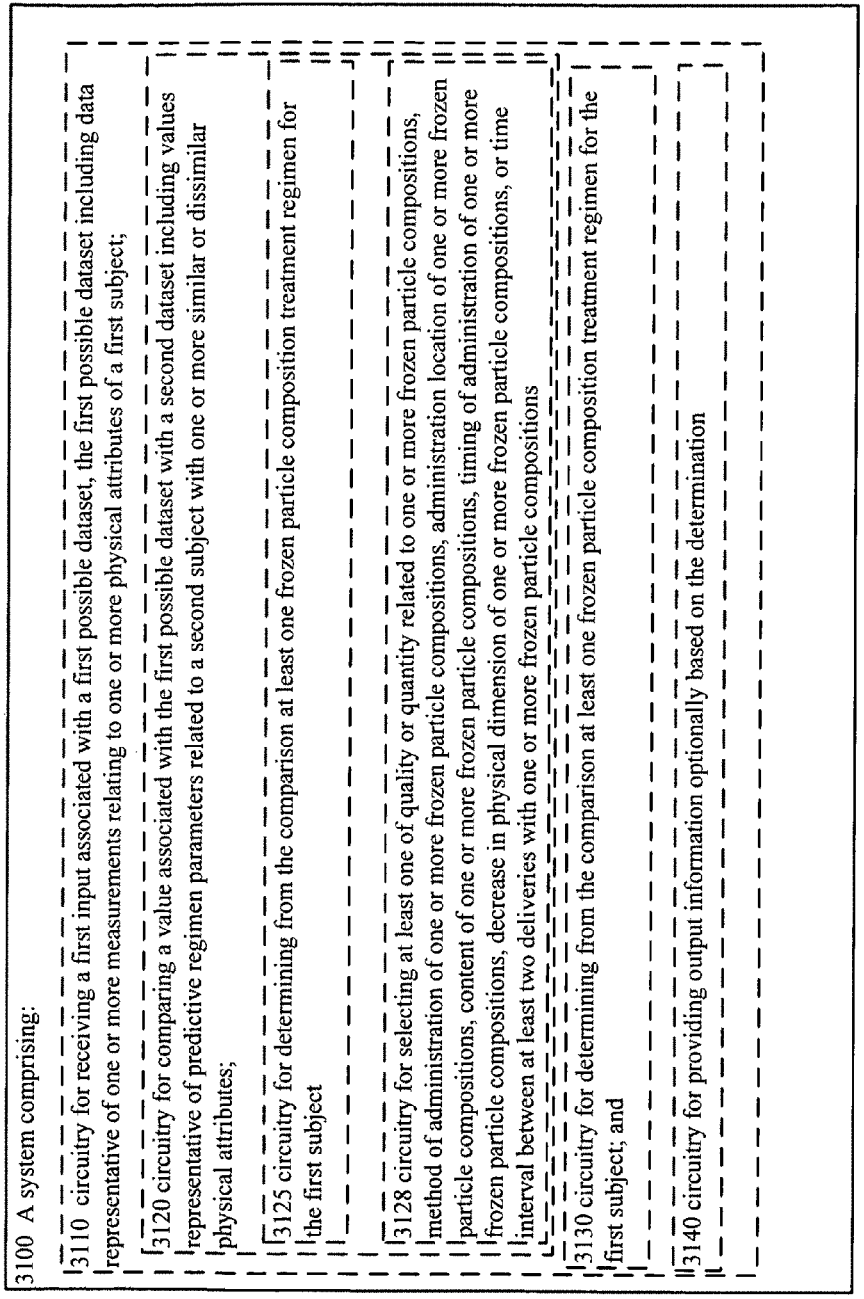
FIG. 31 illustrates a partial view of a system 3100 that includes a computer program for executing a computing process on a computing device.

As shown in FIGS. 31-32, at least one aspect relates to a system 3100 including circuitry 3110 for receiving a first input associated with a first possible dataset, the first possible dataset including data representative of one or more measurements relating to one or more physical attributes of a first subject; circuitry 3120 for comparing a value associated with the first possible dataset with a second dataset including values representative of predictive regimen parameters related to a second subject with one or more similar or dissimilar physical attributes; circuitry 3125 for determining from the comparison at least one frozen particle composition treatment regimen for the first subject; circuitry 3128 for selecting at least one of quality or quantity related to one or more frozen particle compositions, method of administration of one or more frozen particle compositions, administration location of one or more frozen particle compositions, content of one or more frozen particle compositions, timing of administration of one or more frozen particle compositions, decrease in physical dimension of one or more frozen particle compositions or time interval between at least two deliveries with one or more frozen particle compositions.

In at least one embodiment, the system includes circuitry 3130 for determining from the comparison at least one frozen particle composition treatment regimen for the first subject; and circuitry 3140 for providing output information optionally based on the comparison. In at least one embodiment, the circuitry for receiving a first input associated with a first possible dataset includes circuitry 3200 for receiving one or more measurements relating to one or more physical attributes including at least one of height; weight; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; medical history; proteomic profile; partial or whole genetic sequence; partial or whole proteomic sequence; medical history; lymph condition, or blood condition.

In at least one embodiment, the system includes circuitry 3210 for selecting the combination of at least two parameters selected from quality or quantity related to one or more frozen particle compositions, method of administration of one or more frozen particle compositions, administration location of one or more frozen particle compositions, content of one or more frozen particle compositions, timing of administration of one or more frozen particle compositions, decrease in a physical dimension of one or more frozen particle compositions, or time interval between at least two administrations or deliveries with one or more frozen particle compositions.

In at least one embodiment, the system includes circuitry 3220 for selecting the combination of at least two parameters selected from quality or quantity related to one or more frozen particle compositions, method of administration of one or more frozen particle compositions, administration location of one or more frozen particle compositions, content of one or more frozen particle compositions, timing of administration of one or more frozen particle compositions, decrease in a physical dimension of one or more frozen particle compositions, or time interval between at least two administrations with one or more frozen particle compositions.

In at least one embodiment, the system includes circuitry 3230 for selecting at least one of a clinical outcome; secondary effects related to the treatment; disease stage; longevity; or vaccination administration. In at least one embodiment, the clinical outcome 3240 includes a positive clinical outcome or a negative clinical outcome. In at least one embodiment, the clinical outcome includes one or more adverse effect, failure to attain a clinical endpoint of a clinical trial, failing to attain a beneficial effect, or measurement of at least one biochemical, biological or physiological parameter 3250.

Figure 33:
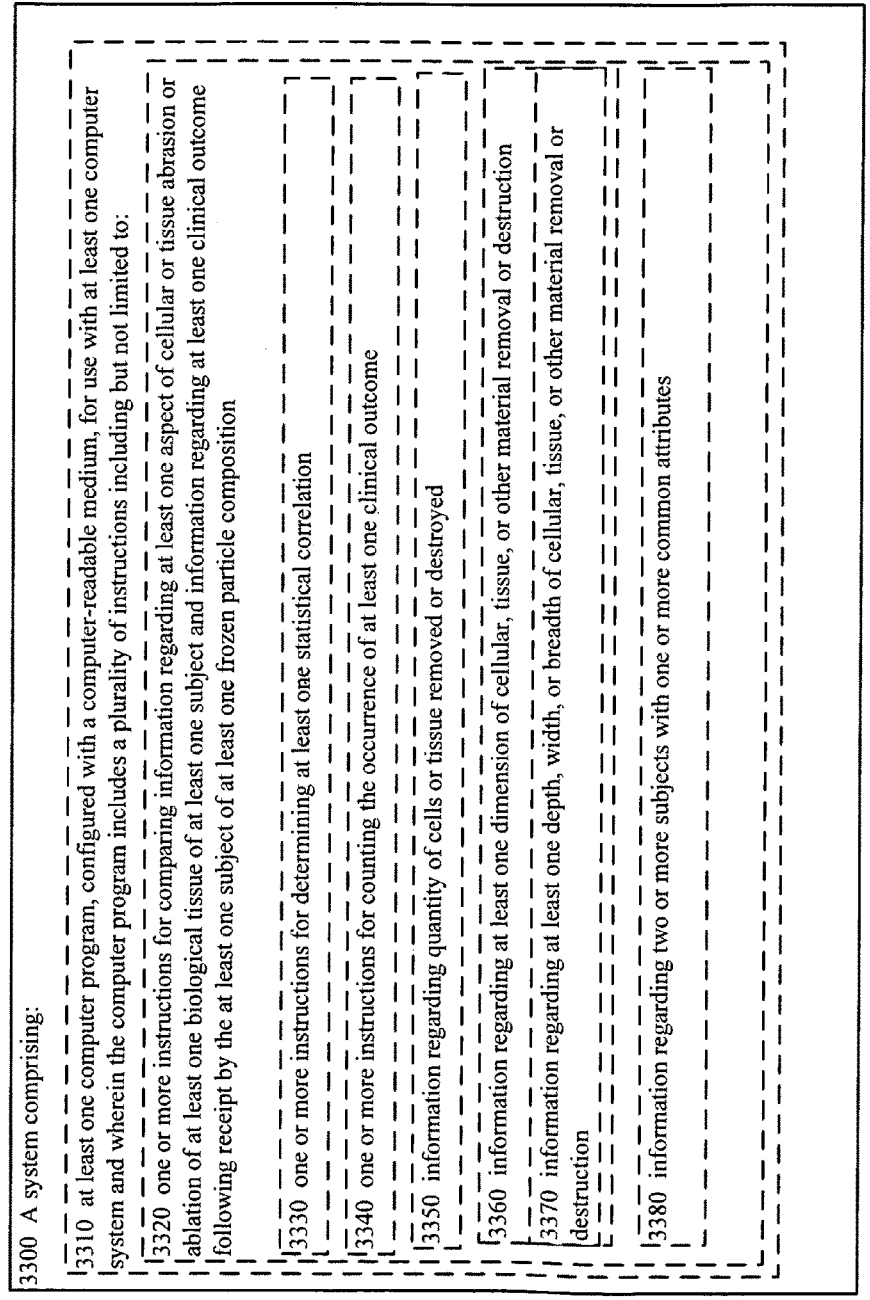
FIG. 33 illustrates a partial view of a system 3300 that includes a computer program for executing a computing process on a computing device.
Figure 34:
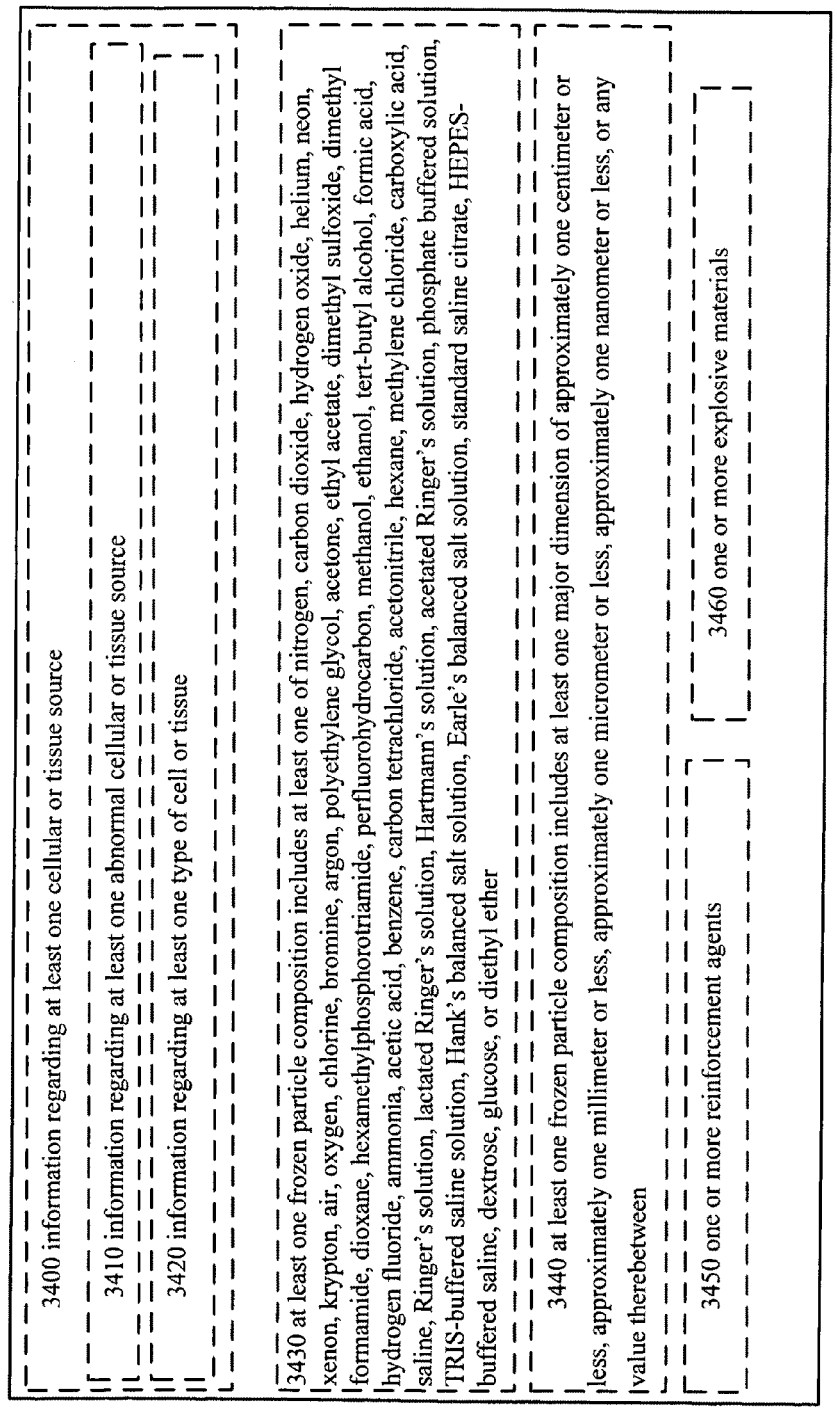
FIG. 34 illustrates a partial view and an embodiment of FIG. 33.

FIGS. 33-35 illustrate a partial view of a system 3300 including at least one computer program 3310 configured with a computer-readable medium, for use with at least one computer system and wherein the computer program includes a plurality of instructions including but not limited to one or more instructions 3320 for determining at least one comparison between information regarding at least one aspect of cellular or tissue abrasion or ablation of at least one biological tissue of at least one subject and information regarding at least one clinical outcome following receipt by the at least one subject of at least one frozen particle composition. In at least one embodiment, the system includes one or more instructions 3330 for determining at least one statistical correlation. In at least one embodiment, the system includes one or more instructions 3340 for counting the occurrence of at least one clinical outcome. In at least one embodiment, information regarding at least one aspect of cellular or tissue abrasion or ablation includes information 3350 regarding quantity of cells or tissue removed or destroyed; information 3360 regarding at least one dimension of cellular, tissue or other material removal or destruction; information 3370 regarding at least one of depth, width, or breadth of cellular removal or destruction; or information 3380 regarding two or more subjects with one or more common attributes. In at least one embodiment, the information regarding at least one aspect of cellular or tissue abrasion or ablation includes information 3400 regarding at least one cellular or tissue source, including information 3410 regarding at least one abnormal cellular or tissue source or information 3420 regarding at least one type of cell or tissue.

In at least one embodiment, the at least one frozen particle composition or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 3430. In at least one embodiment, at least one frozen particle composition includes at least one major dimension of approximately one decimeter or less, approximately one centimeter or less, approximately one millimeter or less, approximately one micrometer or less, approximately one nanometer or less, or any value therebetween 3440. In at least one embodiment, the at least one frozen particle composition includes one or more reinforcement agents 3450. In at least one embodiment, the at least one frozen particle composition includes one or more explosive materials 3460.

In at least one embodiment, the receipt by the at least one subject of at least one frozen particle composition or therapeutic composition is pursuant to at least one clinical trial 3500. In at least one embodiment, the system further comprises one or more instructions for determining at least one comparison before the delivery or administration of the at least one frozen particle composition or therapeutic composition to at least one subject 3510.

In at least one embodiment, the system includes one or more instructions for creating at least one inclusion criterion and at least one exclusion criterion for a clinical trial involving the at least one frozen particle composition or therapeutic composition 3520. In at least one embodiment, the system further comprises one or more instructions for suggesting the inclusion of one or more of the at least one subject in at least one clinical trial 3530. In certain instances, multiple subjects from multiple clinical trials are included.

In at least one embodiment, the system further includes one or more instructions for suggesting the exclusion of one or more of the at least one subject in at least one clinical trial 3540. In at least one embodiment, the system includes one or more instructions for using one or more of the at least one comparison to predict at least one clinical outcome regarding at least one second subject 3550. In at least one embodiment, the at least one second subject has not received the at least one frozen particle composition or therapeutic composition 3560. In at least one embodiment, the system includes predicting at least one clinical outcome involving the at least one second subject, wherein the at least one second subject is a plurality of people; and segregating subject identifiers associated with the plurality of people in reference to the predicted at least one clinical outcome 3570. In at least one embodiment, the at least one second subject is a plurality of people; and the system further comprises determining the eligibility of the at least one second subject for the at least one clinical trial 3580.

Figure 36:
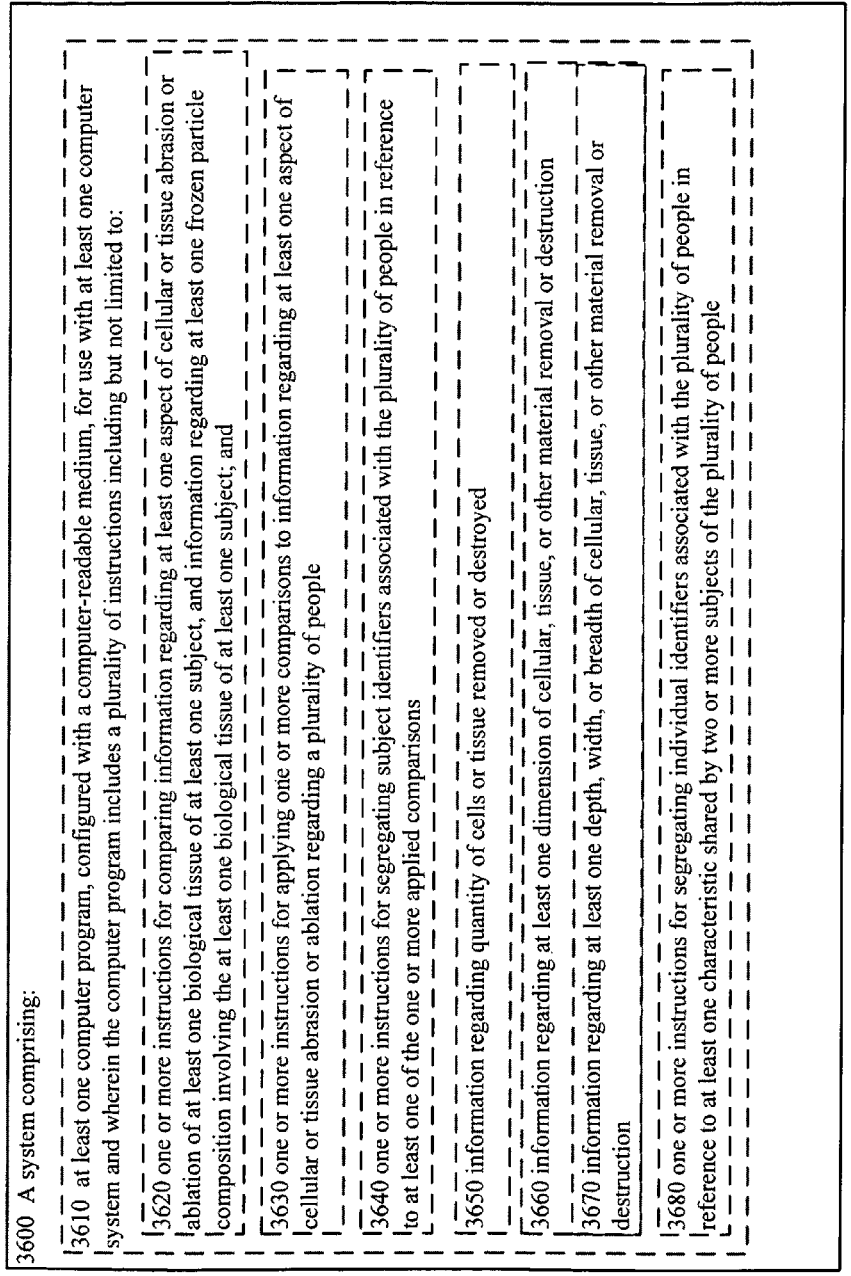
FIG. 36 illustrates a partial view of a system 3600 that includes a computer program for executing a computing process on a computing device.

As indicated in FIG. 36, at least one aspect relates to a system 3600 that includes at least one computer program 3610, configured with a computer-readable medium, for use with at least one computer system and wherein the computer program includes a plurality of instructions including but not limited to one or more instructions 3620 for comparing information regarding at least one aspect of cellular or tissue abrasion or ablation of at least one biological tissue of at least one subject and information regarding at least one frozen particle composition involving the at least one biological tissue of at least one subject; and one or more instructions 3630 for applying one or more comparisons to information regarding at least one aspect of cellular or tissue abrasion or ablation regarding a plurality of people. In at least one embodiment, one or more instructions 3640 for segregating subject identifiers associated with the plurality of people in reference to at least one of the one or more applied comparisons. In at least one embodiment, the information regarding at least one aspect of cellular or tissue abrasion or ablation includes information 3650 regarding quantity of cells or tissue removed or destroyed; information 3660 regarding at least one dimension of cellular, tissue or other material removal or destruction; or information 3670 regarding at least one of depth, width, or breadth of cellular removal or destruction. In at least one embodiment, the system includes one or more instructions 3680 for segregating individual identifiers associated with the plurality of people in reference to at least one characteristic shared by two or more subjects of the plurality of people.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

For any of the various aspects and embodiments disclosed herein, one or more kits may be developed with the components described herein. In at least one embodiment, a kit includes one or more frozen particles as described herein. In at least one embodiment, a kit includes one or more frozen particles and at least one therapeutic agent as disclosed herein. In at least one embodiment, a kit includes one or more frozen particles and one or more reinforcement agents. In at least one embodiment, a kit includes one or more frozen particles and one or more explosive materials.

EXAMPLES

Example 1

Compositions and Methods of Making Frozen Particles

Frozen particles suitable for various embodiments described herein may be produced by controlling the pressure and temperature of hydrogen oxide that is introduced as a liquid, gas or frozen. Frozen particles, including frozen hydrogen oxide ice Ic, are produced by cooling small hydrogen oxide droplets (~6 μm diameter) below −38° C. (See e.g., Murray, et al., Phys. Chem. Chem. Phys. vol. 8, pp. 186-192 (2006), which is incorporated herein by reference). Emulsions of 30-40% by weight of distilled and de-ionized hydrogen oxide in paraffin oil (Fisher Scientific) are agitated to produce hydrogen oxide droplets of mean diameters ranging from 5 to 35 μm as determined by optical microscopy. The droplets are cooled to −110° C. at a rate of 10° C./min by using a cryostat cooled with liquid nitrogen and containing a heater and temperature controller. Freezing liquid droplets with a median diameter of 5.6 μm or smaller can provide approximately 80% frozen ice Ic and approximately 20% frozen ice Ih. Following the procedures of Murray et al, selective production of ice Ic in pellet form produces quantities suitable for use in various embodiments described herein.

Frozen particles generated in this manner are utilized for abrasion of at least one biological tissue, including but not limited to skin. The frozen particle composition is administered to at least one biological tissue by, for example, accelerating, ejecting, or propelling the frozen particles by way of a carrier gas under pressure (e.g., air, carbon dioxide, nitrogen) through a tube, or other device directed toward at least one biological tissue, such as skin. Microdermabrasion, microscissuining, or other surface abrasion techniques are carried out in a similar fashion.

Example 2

Compositions and Methods of Making Frozen Particles

Frozen particles, including frozen hydrogen oxide ice Ic, are produced by depositing hydrogen oxide vapor onto a copper plate held at low temperatures in vacuo. Purified (deionized) hydrogen oxide is added to a vessel at approximately 25° C. and the hydrogen oxide vapor is condensed onto a metal plate held at approximately −196° C. in vacuo. The deposited amorphous ice is heated (at 10° C./min) to approximately −93° C. and is converted to crystalline cubic ice (ice Ic). Ice Ic is stable when stored under liquid nitrogen (See e.g., Johari, et al., J. Phys. Chem., vol. 94, pp. 1212-1214 (1990), which is incorporated herein by reference). An example of an apparatus that is used to produce frozen hydrogen oxide ice Ic is described in Hallbrucker et al (J. Phys. Chem., vol. 93, pp. 4986-4990 (1989), which is incorporated herein by reference).

Example 3

Compositions and Methods of Making Frozen Particles

Frozen hydrogen oxide ice Ic particles are produced from small hydrogen oxide droplets in an example of a "pelletizer" apparatus similar to those described by, for example, U.S. Pat. No. 4,617,064; U.S. Pat. No. 6,306,119, which are incorporated herein by reference. Frozen hydrogen oxide ice Ic particles are formed by spraying hydrogen oxide droplets of the desired size into a cooling chamber filled with a cold inert gas maintained at the desired temperature, for example, nitrogen gas maintained at approximately −100° C. to promote formation of ice Ic. Spray droplet size is maintained by variation of nozzle/orifice size and hydrogen oxide pressure to yield droplet diameters ranging from nanometers to centimeters. Frozen hydrogen oxide ice Ic, ice Ih, amorphous low density ice, amorphous high density ice, and other forms are produced by controlling the temperature and pressure of the cooling chamber. Cubic hydrogen oxide ice Ic particles are formed in a step-wise process, by maintaining the chamber at a very low temperature (approximately −196° C.) with increased pressure, which first promotes formation of amorphous hydrogen oxide ice. Next, the chamber is heated to approximately −93° C., which results in transformation to cubic hydrogen oxide ice (ice Ic) particles.

The hydrogen oxide ice particles are propelled into a delivery system (such as tubing and nozzle) by nitrogen gas under pressure. The delivery system is maintained at the appropriate temperature for preservation of the hydrogen oxide particle structure, (e.g., approximately −93° C. for ice Ic structure).

Example 4

Compositions and Methods of Making Frozen Carbon Dioxide Particles

Carbon dioxide frozen particles are produced from small carbon dioxide droplets in a "pelletizer" similar to those described by, for example, U.S. Pat. No. 4,617,064; and U.S. Pat. No. 6,306,119; each of which is incorporated herein by reference. Carbon dioxide frozen particles are formed by spraying liquid carbon dioxide droplets into a cooling chamber maintained at low temperatures (e.g., approximately −100° C.). Droplet size is regulated by varying nozzle or orifice size, and pressure. Carbon dioxide droplet diameters range, for example, from nanometers to centimeters. The frozen carbon dioxide particles are propelled into a delivery system (e.g., tubing and nozzle) by carrier gas, (e.g., air or nitrogen) under pressure. The carbon dioxide particles are maintained while in the delivery system at the appropriate temperature, (e.g., approximately −100° C.). Frozen carbon dioxide particles sublimate, or transition to a gas phase, at approximately −78.5° C. and 1 atm pressure.

Example 5

Compositions and Methods of Making Frozen DMSO Particles

Dimethyl sulfoxide (DMSO) frozen particles are produced from DMSO droplets, for example, in a "pelletizer" apparatus similar to those described by, for example, U.S. Pat. No. 4,617,064; U.S. Pat. No. 6,306,119, which are incorporated herein by reference. DMSO frozen particles are formed from spraying liquid DMSO droplets of the desired size into a cooling chamber that is maintained at low temperature, for example, less than approximately 18.5° C. Droplet size is regulated by varying nozzle or orifice size, and pressure, with compressed air as a carrier gas. Droplet size can be regulated by varying nozzle or orifice size, and DMSO pressure. DMSO droplet diameters range, for example, from nanometers to centimeters. The DMSO frozen particles are propelled by a carrier gas (e.g., air or nitrogen) under pressure to enter a delivery system (e.g., tubing and nozzle). In order to preserve DMSO particle structure, the delivery system is maintained at low temperature (e.g., less than approximately 18.5° C.).

Example 6

Methods of Assessment or Selection of Frozen Particles

According to various embodiments described herein, at least one frozen particle is made by lowering the temperature of liquid droplets of a selected material. Droplet and particle sizes are measured by imaging a spray or particle stream upon a background screen. The background screen is illuminated with a short pulse of light, for example, from an infrared laser beam (at approximately 805 nm), which is capable of pulsing at frequencies of approximately 1000 Hz.

A digital camera captures high resolution images of the droplets or particles. High-speed, real-time particle sizing software analyses the images to assess the diameter distribution for the particles and to determine the shape. The diameter of each droplet is determined automatically by referencing the number of dark pixels in the droplet image to the pixel area of a calibration circle. Droplet diameters between approximately 100 μm (±3.2%) and approximately 2000 μm (±0.03%) were measured with 95% confidence (See e.g., Ireland et al., 6th ASME-JSME Thermal Engineering Joint Conference (2003), which is incorporated herein by reference). Instruments, computer programs and protocols for measuring particle and droplet size are available, for example, from Oxford Lasers, Shirley, Mass. (e.g., world wide web at oxfordlasers.com, which is incorporated herein by reference).

Example 7

Methods of Assessment or Selection of Frozen Particles

According to various embodiments described herein, at least one frozen particle is made by lowering the temperature of liquid droplets of a selected material. Droplet and particle sizes are measured by laser diffraction. Laser diffraction based particle size analysis relies on particles passing through a laser beam and scattering light at an angle that is directly related to their size. As particle size decreases, the observed scattering angle increases logarithmically. Scattering intensity is also dependent on particle size, and decreases with decreasing particle volume. Thus, large particles scatter light at narrow angles with high intensity whereas small particles scatter at wider angles but with low intensity. Laser diffraction is used for the non-destructive analysis of wet or dry samples, to measure particles in the size range 0.02 to 2000 micrometers (e.g., world wide web at chemie.de/articles/e/61205/, which is incorporated herein by reference). A laser diffraction instrument, protocols and analysis software are available, for example, from Malvern Instruments Ltd. (Malvern, Worcestershire, WR14 1XZ United Kingdom).

Example 8

Compositions and Methods of Making Frozen Particles Including a Reinforcement Agent One or more reinforcement agents are added to the frozen particles during the formation process. Among other things, reinforcement agents can increase the strength of frozen particles (e.g., increase the modulus of rupture of ice) and decrease the deformation of frozen particles (e.g., decrease the beam deflection of ice). As indicated in Table A below, glass fibers present at 9% (wt./vol.), for example, increase the modulus of rupture of ice by approximately 7-fold relative to ice derived from unreinforced hydrogen oxide ice (See e.g., Kingery, Science, vol. 134, pp. 164-168 (1960), which is incorporated herein by reference).

TABLE A

Strength of fresh ice with sawdust and Fiberglass, respectively, added. Additions were % wt./vol. (Kingery, Ibid).

| Addition (%) | Modulus of rupture (kg/cm²) | |
|---|---|---|
| | Sawdust (−17° C.) | Fiberglass (−20° C.) |
| 0 | 22.5 | 24.1 |
| 0.8 | 22.7 | 24.0 |
| 2.5 | 35 | 65.4 |
| 9.0 | 60 | 161 |
| 14.0 | 66.7 | N/A |

As indicated in FIG. 5, the beam deflection is less than 0.005 inches for hydrogen oxide ice that is reinforced with approximately 9.0% glass fibers and increases over time for hydrogen oxide ice that is reinforced with approximately 0.8% glass fibers (Kingery, Ibid). Furthermore, hydrogen oxide ice with approximately 9% (w/v) of glass fibers is not deformed over 23 hours under an applied force of approximately 24.5 in·lbs. As described in Kingery, et al, and as indicated in FIG. 5, beam deflection of hydrogen oxide ice with approximately 0.8% glass fibers is approximately 0.16 inches after 23 hours under 25.3 in·lbs. of force. Likewise, as indicated in FIG. 5, and according to Kingery et al, hydrogen oxide ice without reinforcement agents is deformed approximately 0.05 inches after 4 hours under approximately 26.6 in·lbs. of force. Additionally, aluminum and silica carbonate particles can be mixed at various volume fractions and co-milled under an argon atmosphere to produce nanocrystalline composites as reinforcement agents for frozen particle compositions. (See e.g., Kamrani, et al., Powder Met. vol. 50, pp. 276-282(7) (2007), which is incorporated herein by reference).

Example 9

Compositions and Methods of Making Frozen Particles

Frozen particles (e.g., carbon dioxide, DMSO, gelatin) are reinforced by incorporating one or more reinforcement agents, including but not limited to silica beads, fiberglass, polyethylene glycol, kaolin, or wood fibers.

Silica beads approximately 1 micrometer in diameter are mixed with hydrogen oxide at approximately 0° C. to make volume fractions including the approximate ranges, but not limited to, 0, 0.004, 0.04, 0.15, 0.29, 0.49 and 0.63 volume fraction. The volume fractions, or one or more particular volume fraction, are frozen in, for example, a cylindrical mold, at low temperatures (e.g., approximately −10° C.). Unconfined coaxial compression tests are used to determine the maximum stress (also known as the failure point) of the one or more frozen particles at defined temperatures and strain rates (See e.g., Yasui et al, Geophys. Res. Lett., vol. 35, L12206, (2008), which is incorporated herein by reference).

As indicated in FIG. 6, maximum stress values (MPa) increase for mixtures with an increased volume fraction of silica beads relative to the maximum stress for unreinforced hydrogen oxide ice. (See e.g., Yasui et al, Ibid.) $\phi$=silica volume fraction The strength of specific frozen particles is altered by varying the composition of frozen particle mixtures containing one or more reinforcement agents. For example, Table B indicates the frozen particle strength of frozen particles including hydrogen oxide, DMSO, carbon dioxide, and gelatin, which contain at least one reinforcement agent. As indicated, the reinforced frozen particles exhibited increased strength compared to their unreinforced counterparts. As indicated in Table B, frozen particles containing at least one reinforcement agent at the volume fractions shown in the table displayed maximal strength in compression tests. (See also, FIGS. 5 and 6, as well as Table A herein for hydrogen oxide frozen particle strength).

TABLE B

Frozen particles and reinforcement agents leading to increased particle strength

| Particle Base | Fiber Glass | Saw Dust | Silica Beads | PEG | Kaolin |
|---|---|---|---|---|---|
| Ice | 0.15* | 0.14 | 0.63 | ND | 0.15 |
| DMSO | 0.15 | 0.14 | 0.63 | ND | 0.15 |
| carbon dioxide | 0.15 | 0.14 | 0.63 | ND | 0.15 |
| gelatin | 0.15 | 0.14 | 0.63 | ND | 0.15 |

Volume fraction for reinforcement agents in frozen particle base materials is given.
ND = Not Determined. (Yasui, et al.)

Example 10

Vaccine Compositions and Methods of Making Frozen Particles

As described herein, immunization of a subject with a vaccine is accomplished by way of introduction of the vaccine through, for example, subcutaneous, transcutaneous or intramuscular administration. (See e.g., Berzofsky et al, Nat. Rev. Immunol. vol. 1, pp. 209-219, (2001), which is incorporated herein by reference). Non-limiting examples of frozen particle vaccines are described herein, and include one or more immunogens. The immunogen therapeutic compositions are made, for example, in solution or as a solid in suspension created from buffered solutions (e.g., phosphate, citrate, lactate, pyruvate or an organic acid buffer) that optimize the stability and immunogenicity of the vaccine.

Storage stability of vaccines depends upon many factors, including vaccine formulation and storage temperature. For example, an influenza subunit vaccine formulated with trehalose, and Hepes buffered saline, is stable at room temperature for approximately 26 weeks (See e.g., Amorij et al, Pharm. Res. vol. 25, pp. 1256-1273 (2008), which is incorporated herein by reference).

Vaccines with adjuvants such as: N-acetyl muramyl-1-alanyl-d-isoglutamine, also called muramyl dipeptide (MDP) or monophosphoryl lipid A (MPL) elicit enhanced cellular and humoral immunity (See e.g., Aguilar et al Vaccine vol. 25, pp. 3752-62 (2007), which is incorporated herein by reference).

One or more hydrogen oxide frozen particle vaccine compositions, including, for example, one or more buffers, one or more immunogens (e.g., viral protein subunits) and one or more adjuvants, as a solution or suspension, are made by spraying the compositions through an orifice or nozzle. Each vaccine composition is propelled by a pressurized gas (e.g., compressed air) into a cooling chamber maintained at, for example, approximately −40° C.

The vaccine composition is delivered to at least one biological tissue of a subject, for example, by propelling the particles via a carrier gas under pressure (e.g., air, carbon dioxide, nitrogen) through a tube directed toward at least one biological tissue (including but not limited to vascular, lymphatic, lymph node, epidermal, subcutaneous, intramuscular, oral, nasal, pulmonary, intraperitoneal or rectal tissue).

Alternatively, the vaccine composition is delivered to at least one biological tissue of a subject, for example, by first forming the frozen particle vaccine compositions through spraying composition droplets into a cryogen bath (e.g., liquid nitrogen). The frozen particle compositions are subsequently delivered to at least one biological tissue by flash boiling liquid nitrogen, and propelling the frozen particle compositions through a tube or barrel, for example, to at least one biological tissue of a subject.

Frozen particle vaccine compositions containing one or more reinforcement agents (e.g., silica beads) and of the appropriate size and shape (e.g., bullet, spheroid, high aspect ratio shape) penetrate the at least one biological tissue when propelled to high velocity by a carrier gas. In one non-limiting example, a vaccine composition approximately 20-70 µm in size penetrates the epidermis when the composition is accelerated to high speed with a powder jet injector (PowerJect, PowerJect Pharmaceuticals) (Amorij et al, Ibid.).

Example 11

Vaccine Compositions and Methods of Making Frozen Particles

Frozen particle vaccine compositions containing multiple immunogens, for example, toxoids (chemically modified toxins) from bacteria such as *Clostridium tetani, Cornybacterium diphtheriae* or *Bordetella pertussis*, stimulate immunity to multiple bacteria or toxins in a single vaccine composition.

Alternatively, multiple distinct immunogens, proteins, or peptides that are derived from a single pathogen are combined in a single frozen particle vaccine composition that immunizes a subject against a pathogenic virus or bacteria that mutates frequently. For example, multiple hemagglutinin or neuraminidase proteins, (e.g., H1N1, H3N2) from different viral strains (e.g., A/New Calcdonia/H1N1, or A/Wellington/H3N2) or viral species of influenza (e.g., influenza A or influenza B) are combined in a single frozen particle vaccine composition and provides immunity to multiple strains or species. (See e.g., Kamps et al, Influenza Report, pp. 127-149 (2006); world wide web at influenzareport.com/ir/vaccines; each of which is incorporated herein by reference).

Alternatively, frozen particle vaccine compositions including one or more immunogens, antigens or proteins (e.g., influenza A/New Calcdonia/(H1N1)) are combined with one or more frozen particle vaccine compositions containing one or more different antigens (e.g., influenza B/Shanghai or influenza A/Wellington/(H3N2)). Such a frozen particle vaccine composition combination provides immunity against seasonal variants of viral pathogens.

In one non-limiting example, combinations of frozen particle vaccine compositions including specific antigens from selected influenza variants or strains target a seasonal flu epidemic. (Kamps et al, Ibid.) Combination of frozen particle compositions are made containing one or more different antigens or epitopes, wherein the one or more different antigens or epitopes are derived from mutant or variant HIV proteins that evolve during HIV infection (See e.g., Berzofsky et al, J. Clin. Inv. vol. 114, pp. 450-462 (2004)). Such combination compositions immunize a subject against existing HIV mutants and anticipate the emergence of new HIV mutants or variants.

Alternatively, one or more frozen particle vaccine compositions are delivered to one or more mucosal tissues (e.g., nasal, oral, rectal, pulmonary) via propulsion using a "pellet gun," via inhalation, or ingestion by a subject. For example, an influenza vaccine lyophilized and delivered nasally as spherical particles, approximately 26.9 µm (mean diameter), induces mucosal (e.g., nasal IgA response) and systemic immunity (e.g., serum antibody response) to influenza virus (See e.g., Garmise et al, AAPS PharmSciTech. vol. 8:E81 (2007); Huang et al, Vaccine. vol. 23(6), pp. 794-801 (2004); each of which is incorporated herein by reference).

Alternatively, the one or more frozen particle vaccine compositions are delivered to one or more pulmonary surfaces of the subject via propulsion by way of a "pellet gun," by using flash boiled liquid nitrogen as a propellant, or by inhalation. Frozen particle influenza vaccine compositions administered to one or more pulmonary surfaces of a subject elicit mucosal and systemic humoral, as well as cell-mediated immune responses to influenza (See e.g., Amorij et al Vaccine. vol. 25, pp. 8707-8717 (2007), which is incorporated herein by reference).

Example 12

Compositions and Methods of Making Frozen Particles

Frozen particle compositions of the appropriate size and shape, including botulinum toxin, an optimal buffer (e.g., Hepes buffer), one or more stabilizing agents, and one or more reinforcement agents are administered through the skin of a subject to neuromuscular junctions. Botulinum toxin inhibits acetylcholine release, which blocks synapse formation, and temporarily paralyzes the corresponding musculature.

Frozen particle compositions containing a recommended dose of botulinum toxin (See e.g., Borodic, U.S. Pat. No. 5,183,462, which is incorporated herein by reference), and at least one reinforcement agent (e.g., polymer) are administered to skeletal muscles using a delivery system derived from inkjet printer technology (See e.g., world wide web at en.wikipedia.org/wiki/Inkjet Printer) that sprays picoliter quantities of the frozen particle compositions at high velocity (e.g., 50 m/sec) toward the skin of the subject. Botulinum toxin is typically administered by subcutaneous injection (generally with a 26 gauge hypodermic needle). Botulinum toxin is approved by the FDA for therapy of strabismus (crossed-eyes), blepharospasm (uncontrolled blinking), and other facial nerve disorders including hemifacial spasm. It is also approved for treatment of cervical dystonia and glabellar (frown) lines (See e.g., Jankovic, J. Neurol. Neurosurg. Psychiatry vol. 75, pp. 951-957 (2004), which is incorporated herein by reference).

In addition, botulinum toxin is included in the treatment of focal or segmental dystonia (e.g., oromandibular-facial-lingual dystonia, laryngeal dystonia, limb dystonia). Dystonias are neurological disorders with repetitive and patterned contractions of muscles that cause abnormal movements and postures. For example, cervical dystonia subjects are injected with, for example, approximately 100 I.U of botulinum toxin, distributed over 3-5 injection sites, spaced 5-15 mm apart, across the length of the stemomastoid muscle. (Borodic, Ibid.)

Frozen particle vaccine compositions containing botulinum toxin are administered to facial muscles that underlie frown lines, wrinkles, and "crow's feet." For example, botulinum toxin is targeted to: 1) the corrugator and procerus muscles to treat vertical glabellar eyebrow furrows; 2) to multiple sites in the frontalis muscle to eliminate horizontal lines in the forehead; or 3) to the lateral orbicularis oculi to treat crow's feet.

Frozen particle compositions containing an optimal dose of botulinum toxin (e.g., 0.2-0.4 I.U./kg) are administered over the length of a specific facial muscle (e.g., orbicularis oculi) by use of a delivery system with an inkjet nozzle. As described herein, picoliter volumes of one or more frozen particle compositions are sprayed at a velocity that achieves a desired or predetermined depth (for example, 5-8 mm; Borodic, Ibid.). The velocity is also altered according to the size, shape, and constituents of the frozen particle composition.

Example 13

Methods of Administering Frozen Particle Therapeutic Compositions

Frozen hydrogen oxide particles of ice Ic form and at least one therapeutic agent or at least one diagnostic agent are formulated for treatment of hematological cancers (e.g., leukemia or lymphoma) or solid tumors (e.g., carcinoma, sarcoma). For example, at least one of neo-adjuvant therapy, adjuvant therapy, chemotherapy, antibody therapy, or immunotherapy are employed In one non-limiting embodiment, frozen hydrogen oxide particles are used for adjuvant therapy of cancers treated with surgery such as colon cancer, lung cancer, and breast cancer. At least one frozen particle hydrogen oxide therapeutic composition containing one or more reinforcement agents (e.g., silica beads, Kevlar®), one or more buffers, one or more stabilizing agents (e.g., one or more saccharides), and one or more cancer therapeutic agents (such as one or more chemotherapy drugs, antibodies, biological agents (e.g., antibodies, cytokines or peptides), or one or more chemotherapeutic agents) are administered to an area proximal to a region of at least one biological tissue where a tumor is present or believed to be present. Optionally, resection of at least a part of a tumor may be performed, with or without additional administration of the at least one frozen particle therapeutic composition.

The at least one frozen particle therapeutic composition is administered in such a manner as described herein, that allows for desired depth of penetration of the at least one biological tissue. In one embodiment, the at least one frozen particle therapeutic composition is administered to a depth that allows for at least one of intracellular or intercellular delivery. For example, the at least one frozen particle therapeutic composition is administered to a depth that allows for delivery to at least one of epithelium, endothelium, vasculature, lymphatic vessels, lymph nodes or mucosa.

Specifically, if metastasis is present or believed to be present in the subject, administration of the at least one frozen particle therapeutic composition is delivered to such region of metastases or micro-metastases are believed to be present.

Frozen particle hydrogen oxide therapeutic compositions provide as an adjuvant therapy are administered by spraying at least one composition under pressure with a carrier gas through a nozzle designed to uniformly distribute particles over at least one biological tissue at sufficient velocity to penetrate the tissue exposed during tumor resection.

Advanced colon cancer (e.g., stage II, III) is treated surgically by removal of sections of colon containing tumor with margins of "normal" colon tissue and often includes removal of associated lymph nodes and mesentery (colectomy). Standard adjuvant therapy following surgery is systemic administration of a combination of chemotherapy drugs (e.g., 5-fluorouracil, leucovorin or oxaliplatin (FOLFOX)), (See e.g., Wolpin et al, CA Cancer J. Clin. vol. 57, pp. 168-185 (2007)). Systemic FOLFOX adjuvant therapy is associated with significant toxicities including gastrointestinal toxicity, neutropenia and neurotoxicity (Wolpin et al, Ibid.). Localized in situ delivery of FOLFOX by administration of frozen particle therapeutic compositions permits delivery of a lower dose.

Administration of at least one frozen particle hydrogen oxide therapeutic composition containing at least one therapeutic antibody includes, for example, bevacizumab (an anti-vascular endothelial growth factor) or cetuximab (an anti-epidermal growth factor receptor). Bevacizumab and cetuximab both target the tumor-associated vasculature and tumor cells in the remaining colon sections and the surrounding tissues, mesentery and lymph nodes. Localized administration of therapeutic antibodies provides sustained protection from recurrence of colon tumors at the site of tumor resection and in the surrounding tissues. (Wolpin et al, Ibid.). Following surgery and adjuvant therapy with one or more frozen particle hydrogen oxide therapeutic compositions, including at least one of one or more chemotherapy drugs, or one or more antibodies, the remaining colon sections are spliced together (i.e. anastomosis) or an artificial orifice (i.e. stoma) is inserted to restore a functional colon.

Example 14

Methods of Administering Frozen Particle Therapeutic Compositions

Frozen particle hydrogen oxide therapeutic compositions including one or more cancer therapeutics or one or more cancer diagnostics are used to treat cancers in distal locations from the primary tumor or initial tumor site treated with surgery or radiation. For example, colon cancer cells often metastasize to the liver ((Wolpin et al, Ibid.). At the time of surgical resection of colon cancer tumors, one or more frozen particle hydrogen oxide therapeutic compositions including at least one cancer therapeutic, such as one or more cytotoxic drugs (e.g., fluouracil), antibodies (e.g., cetuximab), radioisotopes conjugated to antibodies (e.g., $^{131}$I-cetuximab), or one or more mixtures of at least one cytotoxic drug and at least one biological-based therapeutic agent are administered to the liver and surrounding tissues.

Administration of the at least one frozen particle hydrogen oxide therapeutic composition is accomplished by traditional surgery or laparoscopic surgery that allows access to the liver (or other organs to be treated). Administration of at least one frozen particle hydrogen oxide therapeutic composition directly to the liver and the surrounding vasculature allows for intracellular or intercellular penetration and release of at least one anti-cancer therapeutic for treatment of any existing or suspected colon cancer mestastases or micro-metastases.

As described herein, the at least one frozen particle hydrogen oxide therapeutic composition including one or more cancer therapeutics are administered by way of a spraying device. Such a spraying device includes an insulated tube and nozzle, as well as a valve that controls the flow of particles. In the case of traditional surgery for tumor or tissue resection, the at least one frozen particle hydrogen oxide therapeutic composition is sprayed directly onto the target tissue or tissues. Whereas in the case of laparoscopic surgery for tumor or tissue resection, the at least one frozen particle hydrogen oxide therapeutic composition is sprayed through a trocar (a hollow tube approximately 10 millimeters in diameter).

In certain spraying devices, the at least one frozen particle hydrogen oxide therapeutic composition is administered by way of a carrier gas. The depth of penetration by the at least one therapeutic composition is controlled by regulating the carrier gas pressure as well as the consequent particle velocity. The at least one therapeutic composition optionally includes one or more tracer agents or is delivered simultaneously with one or more tracer agents. Some non-limiting examples of tracer agents include dyes, stains or fluorescent compounds that mark the tissue area sprayed. The one or more tracer agents can optionally monitor or provide feedback as to the quantity or quality (in the case of multiple therapeutic compositions administered simultaneously or over time) of the at least one therapeutic composition administered to a specific site.

In at least one embodiment, the at least one frozen particle hydrogen oxide therapeutic composition including at least one cancer therapeutic further includes hematoxylin and eosin stains mixed at a known ratio (e.g., 1:10). Alternatively, a batch of the at least one frozen particle hydrogen oxide therapeutic composition is administered in a mixture or in separate applications frozen particles including hematoxylin and eosin stains. Staining of tissues is visualized by inspection with a low power microscope (e.g., dissection microscope) or with a laparoscope, which allows for assessment of the relative quantity or quality of the at least one therapeutic composition administered to the tissue. Staining of the tissues further provides a guide as to the region that received the at least one therapeutic composition.

Example 15

Methods of Administering Frozen Particle Therapeutic Compositions

Frozen particle hydrogen oxide therapeutic compositions including carbon dioxide and at least one cancer therapeutic are administered to at least one tumor or tissue suspected of being cancerous. Upon administration, the frozen particle hydrogen oxide therapeutic compositions penetrate one or more tumor cells, warm to ambient temperature, and undergo rapid sublimation and gaseous expansion of the carbon dioxide. This rapid reaction produces a small explosion that destroys at least one tumor cell as well as one or more adjacent cells. In addition, administration of the frozen particle therapeutic compositions at low temperatures (e.g., lower than approximately $-78.5°$ C., which is the approximate sublimation temperature for carbon dioxide at 1 atm pressure), freezes cells and tissues, causing tumor cell death (See e.g., Vergnon et al, Eur. Respir. J. vol. 28 pp. 200-218 (2006); incorporated herein by reference).

Alternatively, carbon dioxide gas is entrapped in frozen particles by placing the liquid phase (e.g., hydrogen oxide) under high pressure in the presence of carbon dioxide gas. (See e.g., U.S. Pat. Nos. 4,289,794; 4,289,790; 4,262,029; 5,439,698, each of which is incorporated herein by reference). Administration of the at least one therapeutic composition is conducted as described herein. In at least one embodiment, the use of a tube and nozzle is used that sprays the frozen particle therapeutic compositions under pressure in a carrier gas (e.g., carbon dioxide, nitrogen). Administration of the at least one therapeutic composition is carried out as an adjuvant therapy in conjunction with tumor resection, or as an alternative when tumor resection is not favored. For example lung cancer tumors are generally inoperable when such tumors are adjacent to airways, or infiltrate central airways including the trachea, main stem bronchi or multiple lung lobes. Additionally, subjects with compromised respiration (e.g., those with lung disease, heart disease or advanced age) are generally not candidates for surgery (See e.g., Spiro et al, Amer. J. Respir. Crit. Care Med., vol. 172, pp. 523-529 (2005); which is incorporated herein by reference).

Carbon dioxide frozen particle therapeutic compositions including one or more chemotherapeutic drugs (e.g., cisplatin, docetaxel, vinorelbine), targeted drugs (e.g., gefitnib, erlotnib), or biological-based agents (e.g., cetuximab, panitumumab, bevacizumab) are administered directly onto lung cancer tumors. Administration is conducted via endoluminal bronchoscopy or by video-assisted thoracoscopy by means of an insulated tube and nozzle integral to the endoscopic device. Frozen particle composition velocities and spray rate are controlled by a valve between the spray head and the cooling chamber of the "pelletizer." (See e.g., U.S. Pat. No. 6,306,119, or 6,764,493, each of which is incorporated herein by reference). Precise localization and administration of the frozen particle therapeutic compositions are accomplished by bronchoscopy and endoscopy with fluoroscopy used to mark the field(s) of interest.

Methods for endoscopic targeting of tumors are described, for example, in Huber et al (Chest vol. 107, pp. 463-470 (1995); which is incorporated herein by reference). Moreover, computed tomography, magnetic resonance imaging, positron emission tomography or other techniques are used to locate lung cancer tumors.

Frozen particle therapeutic composition administration by using endoscopic procedures or as an adjuvant therapy in conjunction with traditional surgery is used for various regions of existing or potential carcinogenesis, including mediastinal lymph nodes, vasculature, chest wall and other thoracic sites.

Alternatively, frozen particle therapeutic compositions are delivered during traditional surgery for lung cancer and used to treat inoperable tumors remaining following lobectomy, wedge resection, and pneumonectomy, as well as to treat margins of lobe, wedge or lung excisions to reduce recurrence of lung cancer (See e.g., the worldwideweb at en.wikipedia.org/wiki/Lung_cancer#Surgery; which is incorporated herein by reference). Without wishing to be bound by any particular theory, frozen particle carbon dioxide therapeutic compositions maintained at approximately $-80°$ C. while administered to tumors rapidly freeze the tumor cells leading to formation of ice crystals in tumor cells that destroy cell organelles (e.g., mitochondria) leading to death of the tumor cells. (Vergnon et al, Ibid.)

Similarly, frozen particle therapeutic compositions containing at least one radioactive element deliver radiation to lung cancer tumor cells. One non-limiting example utilizes frozen particle therapeutic compositions including $^{192}$Iridium for irradiating lung tumors that obstruct major airways. Administration of the frozen particle therapeutic compositions is conducted using an endoscope and a wire to place the radioactive compositions in at least one lung tumor. Without wishing to be bound to any theory, tumor cell irradiation results in single-stranded DNA breaks that induce apoptosis and reduce rates of cell division (Vergnon et, Ibid.).

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including"

should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

All publications and patent applications cited in this specification are incorporated herein by reference to the extent not inconsistent with the description herein and for all purposes as if each individual publication or patent application were specifically and individually indicated to be incorporated by reference for all purposes.

What is claimed is:

1. A therapeutic composition, comprising:
one or more frozen hydrogen oxide particles less than 200 micrometers in size and coated with a specific cell receptor; the one or more frozen hydrogen oxide particles each further defining at least two cavities, the first cavity containing at least one anti-tumor agent, including at least one of an alkylating agent, antimetabolite, anthracycline, plant alkaloid, topoisomerase inhibitor, monoclonal antibody, or tyrosine kinase inhibitor;

and the second cavity containing one or more of a cytokine, chemokine, anti-angiogenic factor, anti-inflammatory agent, vaccine, hormone, or radioactive agent.

2. The therapeutic composition of claim 1, wherein the one or more frozen hydrogen oxide particles are in phase ice Ic.

3. The therapeutic composition of claim 1, wherein the composition has a density greater than approximately 0.92 $g/cm^3$.

4. The therapeutic composition of claim 1, wherein the one or more frozen hydrogen oxide particles exist at about −20° C., about −30° C., about −40° C., about −50° C., about −60° C., about −70° C., about −75° C., about −80° C., about −85° C., about −90° C., about −95° C., about −100° C., about −120° C., about −150° C., about −180° C., about −200° C., about −220° C., about −250° C., or any value less than or therebetween.

5. The therapeutic composition of claim 1, wherein the at least one major dimension includes at least one of the radius, diameter, length, width, height, or perimeter.

6. The therapeutic composition of claim 1, wherein the at least one plant alkaloid includes paclitaxel.

7. The therapeutic composition of claim 1, further including one or more of nitrogen, oxygen, air, helium, neon, argon, xenon, chlorine, bromine, or carbon dioxide, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether.

8. The therapeutic composition of claim 1, wherein the one or more frozen hydrogen oxide particles approximate the shape of at least one of a sphere, bullet, flechette, cone, needle, arrow, spear, diamond, pyramid, cylinder, minie ball, shuttlecock, spiral, bell, pear, crystal, cube, spheroid, tetrahedron, or crescent.

9. The therapeutic composition of claim 1, wherein the one or more frozen particles include a plurality of frozen particles that are approximately uniform in size, shape, weight, or density.

10. The therapeutic composition of claim 1, wherein the therapeutic composition includes one or more of a suspension, mixture, solution, sol, clathrate, colloid, emulsion, microemulsion, aerosol, ointment, capsule, powder, tablet, suppository, cream, device, paste, liniment, lotion, ampule, elixir, spray, suspension, syrup, tincture, detection material, polymer, biopolymer, buffer, adjuvant, diluent, lubricant, disintegration agent, suspending agent, solvent, light-emitting agent, colorimetric agent, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, or gel.

11. The therapeutic composition of claim 1, further including one or more reinforcement agents.

12. The therapeutic composition of claim 11, wherein the one or more reinforcement agents include at least one of a natural, artificial, or synthetic agent.

13. The therapeutic composition of claim 11, wherein the one or more reinforcement agents include at least one of a plate, fiber, or spheroid.

14. The therapeutic composition of claim 11, wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, plant matter, animal matter, or mineral matter.

15. The therapeutic composition of claim 11, wherein the one or more reinforcement agents are located at least on the surface or beneath the surface of the particle.

16. The therapeutic composition of claim 11, wherein the one or more reinforcement agents are located within the particle.

17. The therapeutic composition of claim 1, further including at least one of a polymer, biopolymer, nanoparticle, or detection material.

18. The therapeutic composition of claim 17, wherein the detection material includes at least one electronic identification device.

19. The therapeutic composition of claim 18, wherein the at least one electronic identification device includes at least one radio frequency identification device.

20. The therapeutic composition of claim 17, wherein the detection material includes at least one radioactive element.

21. The therapeutic composition of claim 20, wherein the at least one radioactive element includes one or more of $^{32}P$, $^{35}S$, $^{13}C$, $^{131}I$, $^{191}Ir$, $^{192}Ir$, $^{193}Ir$, $^{201}Tl$, or $^{3}H$.

22. The therapeutic composition of claim 17, wherein the detection material includes at least one colorimetric substance.

23. The therapeutic composition of claim 22, wherein the at least one colorimetric substance includes one or more of an inorganic, organic, biological, natural, artificial, or synthetic substance.

24. The therapeutic composition of claim 22, wherein the at least one colorimetric substance includes one or more of a dye, pigment, or light-emitting substance.

25. The therapeutic composition of claim 24, wherein the light-emitting substance includes at least one of a fluorescent substance, phosphorescent substance, or quantum dot.

26. The therapeutic composition of claim 22, wherein the at least one colorimetric substance is biocompatible.

27. The therapeutic composition of claim 17, wherein the detection material includes at least one of a diamagnetic particle, ferromagnetic particle, paramagnetic particle, super paramagnetic contrast agent, or other magnetic particle.

28. The therapeutic composition of claim 1, formulated to be administered by one or more of topical delivery, oral delivery, enteral delivery, mucosal delivery, percutaneous delivery, or parenteral delivery.

29. The therapeutic composition of claim 28, wherein parenteral delivery includes at least one of intravenous delivery, intra-arterial delivery, intracardiac delivery, subcutaneous delivery, intraperitoneal delivery, or intramuscular delivery.

30. The therapeutic composition of claim 1, formulated to be administered by high velocity impact.

31. The therapeutic composition of claim 1, formulated to be administered by one or more devices.

32. The therapeutic composition of claim 1, further including at least one pharmaceutically-acceptable carrier or excipient.

33. The therapeutic composition of claim 1, further including one or more explosive materials.

* * * * *